United States Patent
Tsai et al.

(10) Patent No.: US 10,322,165 B2
(45) Date of Patent: Jun. 18, 2019

(54) TIFA ANTAGONISTS AND THEIR USE FOR TREATING DISEASES

(71) Applicant: ACADEMIA SINICA, Taipei (TW)

(72) Inventors: Ming-Daw Tsai, Taipei (TW);
Tong-You Wade Wei, Taipei (TW);
Pei-Yu Wu, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 15/660,116

(22) Filed: Jul. 26, 2017

(65) Prior Publication Data

US 2019/0030120 A1 Jan. 31, 2019

(51) Int. Cl.
| | |
|---|---|
| *A61K 38/00* | (2006.01) |
| *A61K 38/17* | (2006.01) |
| *C07K 14/47* | (2006.01) |
| *A61K 45/06* | (2006.01) |
| *C12N 15/113* | (2010.01) |

(52) U.S. Cl.
CPC .......... *A61K 38/1709* (2013.01); *A61K 45/06* (2013.01); *C07K 14/47* (2013.01); *C12N 15/113* (2013.01); *C12N 2310/14* (2013.01)

(58) Field of Classification Search
None
See application file for complete search history.

(56) References Cited

U.S. PATENT DOCUMENTS

2017/0204190 A1* 7/2017 Sprecher ................ C07K 14/52

OTHER PUBLICATIONS

Recombinant Human TIFA Protein (H00092610-P01): Novus Biologicals, https://www.novusbio.com/products/tifa-recombinant-protein_h00092610-p01; last visited Jul. 31, 2018.*

Huang et al., "Intermolecular Binding between TIFA-FHA and TIFA-pT Mediates Tumor Necrosis Factor Alpha Stimulation and NF-κB Activation," Molecular and Cellular Biology, vol. 32, No. 14, Jul. 2012 (published ahead of print on May 7, 2012), pp. 2664-2673.

Wei et al., "Aurora A and NF-ζB Survival Pathway Drive Chemoresistance in Acute Myeloid Leukemia via the TRAF-Interacting Protein TIFA," Cancer Research, vol. 77, No. 2, Jan. 15, 2017, pp. 494-508.

Weng et al., "Uncovering the Mechanism of Forkhead-Associated Domain-Mediated TIFA Oligomerization That Plays a Central Role in Immune Responses," Biochemistry, vol. 54, Sep. 21, 2015, pp. 6219-6229.

* cited by examiner

*Primary Examiner* — Jeanette M Lieb
(74) *Attorney, Agent, or Firm* — Birch, Stewart, Kolasch & Birch, LLP

(57) ABSTRACT

The present invention relates to use of TRAF-interacting protein with an FHA domain (TIFA) antagonists for treating diseases. Particularly, the present invention relates to an isolated peptide fragment from TIFA which acts as a dominant negative inhibitor of TIFA and is effective in treating cancer or an inflammatory disorder. The present invention also relates to a method for predicting cancer prognosis based on the TIFA expression level in a subject in need. The present invention further relates to a method for treating a disease via TIFA silencing.

30 Claims, 20 Drawing Sheets

Specification includes a Sequence Listing.

TIFA ANTAGONISTS AND THEIR USE FOR TREATING DISEASES

TECHNOLOGY FIELD

The present invention relates to use of TRAF-interacting protein with an FHA domain (TIFA) antagonists for treating diseases. Particularly, the present invention relates to an isolated peptide fragment from TIFA which acts as a dominant negative inhibitor of TIFA and is effective in treating cancer or an inflammatory disorder. The present invention also relates to a method for predicting cancer prognosis based on the TIFA expression level in a subject in need. The present invention further relates to a method for treating a disease via TIFA silencing.

BACKGROUND OF THE INVENTION

Cancer is among the leading causes of death worldwide. Resistance to chemotherapy and molecularly targeted therapies is a major problem facing current cancer research and treatment. As an example, acute myeloid leukemia (AML) is a clonal hematologic malignancy with great variability in the clinical features, pathogenesis and treatment outcomes. This malignant disorder is caused by abnormal differentiation of hematopoietic precursor cells forfeiting their ability to respond to regulators of proliferation. The standard therapeutic approach for AML patients is initial chemotherapy induction followed by post-remission treatment, with additional chemotherapy cycles or allogeneic stem cell transplantation for relapse prevention (1). Although significant progress has been achieved, current treatments for AML may only offer limited survival benefits rather than provide fully satisfactory responses, presumably due to chemoresistance and disease relapse (1,2). To reduce recurrence rate and promote therapeutic efficacy, it is urgent to identify new targets (3,4).

Nuclear factor-κB (NF-κB) controls various aspects of immune responses and superiorly regulates cell survival, proliferation, and differentiation (5). Recent evidences attribute a growing number of malignancies to aberrant activation of NF-κB that cross-talks with other signaling molecules and pathways (6), thus it is considered a risk factor for poor prognosis in several types of cancer including leukemia (7). In agreement, constitutively activated NF-κB was shown to protect tumor cells from apoptotic stimuli and promote their resistance to chemotherapies and ionizing radiation (8), presumably through transcriptional activation of anti-apoptotic/pro-survival factors Bcl-2 and Bcl-$X_L$ (9). In line with this notion, the role of NF-κB in leukemogenesis has also been addressed for AML (10), and the inhibition of NF-κB re-attains chemosensitivity in this hematopoietic malignancy presumably due to attenuated pro-survival responses and activated pro-apoptotic signals (11). These observations collectively point to the NF-κB signaling axis as a promising therapeutic target (12).

The Aurora family of serine/threonine kinases promotes tumor proliferation through regulation of chromosome alignment, segregation, and cytokinesis during mitosis (13), and has been suggested as anti-cancer target (14). Upregulation of Aurora A has been reported for bone marrow (BM) mononuclear cells in AML patients (15), and shown to be associated with unfavorable-risk cytogenetics and higher white blood cell (WBC) counts (16). In addition, Aurora A has been shown to promote in vitro and in vivo chemoresistance of cancer cells by reducing chemotherapy-induced apoptosis through activation of NF-κB signaling pathways (17). In support, an increasing ratio of Bax/Bcl-2, as suggestive of promoted apoptosis, has been reported upon treatment with Aurora A inhibitor VX680 (18), a drug that showed clinical effectiveness to chronic myeloid leukemia (CML) (19).

TIFA, a TRAF-interacting protein, is a relatively new player in the NF-κB signaling pathway. Our previous study uncovered that overexpression of TIFA is able to promotes NF-κB activity in a TNF-α dependent manner, and that silencing of TIFA attenuates this TNF-α-stimulatedd NF-κB signaling (20). Mechanistically, this signal axis is initiated by a TNF-α-dependent phosphorylation of TIFA at threonine 9 (pThr9) that interacts with the forkhead-associated (FHA) domain of TIFA to facilitate oligomerization of TIFA dimer (20,21). TIFA oligomerization in turn supports the high-ordered architecture of TRAF family components, such as TNF receptor associated factor 2 (TRAF2) or TRAF6, and modulates ubiquitination of TRAF6 to activate IκB kinase (IκK) complex, through which IκB is subsequently phosphorylated and undergoes ubiquitination-dependent degradation allowing nuclear translocation of NF-κB to transactivate downstream factors (22). In addition to TNF-α stimulation, it was shown that such phosphorylation-dependent oligomerization of TIFA is also triggered by a Gram-negative bacteria derived monosaccharide heptose-1,7-bis-phosphate (HBP) to activate innate immunity (23), and that TIFA mediates innate immune response through assembly of NLRP3 inflammasome upon endothelial sheer stress (24), suggesting an essential role of TIFA in modulation of innate immune responses and inflammation.

The FHA domain is composed of around 80-120 amino acids and known to recognize phosphothreonine (pThr) specifically to exert signaling function. The sequence homology among different FHA-containing proteins is relatively low, however the overall structural architecture of FHA domains is well conserved, in which two β-stranded β-sheets forms a β-sandwich. The β-strands are connected by loops which, though varying greatly in length, are responsible for recognition of the specific pThr-ligand. The FHA-pThr binding has been shown to regulate diverse biological functions, ranging from DNA damage repair, cell cycle checkpoints, to signal transduction. The specificity, biological function, structure, and mechanism of FHA domains have been summarized in recent review (25).

SUMMARY OF THE INVENTION

In this invention, it is unexpectedly found that a TIFA peptide fragment as provided herein can act as a TIFA dominant negative inhibitor to block or attenuate cytokine-stimulated NF-κB activation. In particular, the TIFA peptide fragment contains a dimerization-core segment linked to either the N-terminal Thr9 segment or the C-terminal TRAF6/TRAF 2 interacting segment, which is effective in treating cancer or an inflammatory disorder, by blocking or attenuating cytokine-stimulated NF-κB activation via targeting TIFA. Specifically, it is found that expression of the TIFA peptide fragment antagonizes cancer cell growth stimulated by secretion of inflammatory cytokines and enhances chemotoxicity/lowers chemoresistance, leading to a promoted therapeutic efficacy. The present invention also provides treatment of diseases/conditions via TIFA silencing and a method for predicting cancer prognosis based on the TIFA expression level in a subject in need.

Therefore, in one aspect, the present invention provides a TIFA inhibitor which is an isolated TIFA peptide fragment comprising a dimerization-core peptide segment in combination with a Thr9 peptide segment in the N-terminal or in combination with a TRAF6/TRAF2 interacting peptide segment in the C-terminal, wherein (i) the Thr9 peptide segment comprises a N-terminal phosphorylation/oligomerization motif of $MX_1X_2FEDX_3DTX_4EX_5X_6T$ as set forth in SEQ ID NO: 13, wherein $X_1$ is serine (S) or threonine (T), $X_2$ is serine (S), threonine (T), asparagine (N), $X_3$ is alanine (A) or valine (V), $X_4$ is glutamate (E) or glutamine (Q), $X_5$ is threonine (T) or methionine (M), and $X_6$ is valine (V) or leucine (L);

(ii) the dimerization-core peptide segment comprises six β strands, which includes
 (a) a β3 strand having a β3 motif of VKFG;
 (b) a β4 strand having a β4 motif of $YX_1F$, wherein $X_1$ is threonine (T) or isoleucine (I);
 (c) a β5 strand having a β5 motif of $QFX_1LX_2X_3F$, wherein $X_1$ is serine (S), valine (V) or alanine (A), $X_2$ is glutamine (Q) or histidine (H), and $X_3$ is leucine (L), proline (P) or valine (V);
 (d) a β6 strand having a β6 motif of SFEIKN;
 (e) a β7 strand having air motif of LIV; and
 (f) a β8 strand having a β8 motif of $X_1X_2L$, wherein $X_1$ is arginine (R), glutamine (Q) or lysine (K), and $X_2$ is glutamate (E) or threonine (T);
 wherein each of the β3 to β8 strands is connected to the next in sequence from N-terminal to C-terminal by a plurality of internal loop sequences; and (iii) the TRAF6/TRAF2 interacting peptide segment comprises four β strands, which includes
 (a) a β9 strand having a β9 motif of $LX_1KX_2D$, wherein $X_1$ is Asparagine (N) or histidine (H), and $X_2$ is methionine (M), leucine (L), valine (V) or isoleucine (I);
 (b) a β10 strand having a β10 motif of $X_1CX_2 X_3RF$, wherein $X_1$ is arginine (R) or lysine (K), $X_2$ is methionine (M) or leucine (L), and $X_3$ is valine (V), leucine (L) or ioleucine (I);
 (c) a β11 strand having a β11 motif of $YQX_1LX_2 X_3 X_4E$, wherein $X_1$ is phenylalanine (F) or isoleucine (I), $X_2$ is methionine (M), leucine (L), valine (V) or isoleucine (I), $X_3$ is glutamate (E) or glutamine (Q), and $X_4$ is lysine (K) or arginine (R); and
 (d) a β12 strand having a β12 motif of $X_1FX_2X_3X_4 FX_5X_6$, wherein $X_1$ is phenylananine (F) or serine (S), $X_2$ is glutamate (E) or glutamine (Q), $X_3$ is threonine (T) or isoleucine (I), $X_4$ is glutamine (Q), histidine (H) or glutamate (E), $X_5$ is isoleucine (I), valine (V), serine (S) or phenylalanine (F), and $X_7$ is leucine (L), methionine (M) or phenylananine (F);
 wherein each of the β9 to β12 strands is connected to the next in sequence from N-terminal to C-terminal by a plurality of internal loop sequences; and
 a C-terminal loop sequence connected to the C-terminal of the β12 strand;

wherein the isolated TIFA peptide fragment does not contain both of the Thr9 peptide segment and the TRAF6/TRAF2 interacting peptide segment.

In one embodiment, the N-terminal Thr9-phorsphorylation motif is located at positions corresponding to positions 1-14 of SEQ ID NO: 1.

In one embodiment, the β3 motif is located at positions corresponding to positions 47-50 of SEQ ID NO: 1.

In one embodiment, the β4 motif is located at positions corresponding to positions 58-60 of SEQ ID NO: 1.

In one embodiment, the β5 motif is located at positions corresponding to positions 69-75 of SEQ ID NO: 1.

In one embodiment, the β6 motif is located at positions corresponding to positions 84-89 of SEQ ID NO: 1.

In one embodiment, the β7 motif is located at positions corresponding to positions 96-98 of SEQ ID NO: 1.

In one embodiment, the β8 motif is located at positions corresponding to positions 101-103 of SEQ ID NO: 1.

In one embodiment, the β9 motif is located at positions corresponding to positions 106-110 of SEQ ID NO: 1.

In one embodiment, the β10 motif is located at positions corresponding to positions 114-119 of SEQ ID NO: 1

In one embodiment, the β11 motif is located at positions corresponding to positions 122-129 of SEQ ID NO: 1.

In one embodiment, the β12 motif is located at positions corresponding to positions β6-143 of SEQ ID NO: 1.

In some embodiments, the Thr9 peptide segment further comprises two β strands, which includes
 (a) a β1 strand having a β1 motif of $X_1LX_2X_3T X_4 Y$, wherein $X_1$ is cysteine (C) or serine (S), $X_2$ is glutamine (Q) or histidine (H), $X_3$ is methionine (M), isoleucine (I), leucine (L) or valine (V), and $X_4$ is valine (V), isoleucine (I) or leucine (L), and
 (b) a β2 strand having a β2 motif of at positions $X_1X_2X_3P$, wherein $X_1$ is glutamate (E) or aspirate (D), $X_2$ is lysine (K) or threonine (T), and $X_3$ is leucine (L) or phenylalanine (F).
 wherein the β1 strand is connected to the β2 strand in sequence from N-terminal to C-terminal by an internal loop sequence.

In one embodiment, the β1 motif is located at positions corresponding to positions 15-21 of SEQ ID NO: 1.

In one embodiment, the β2 motif is located at positions corresponding to positions 39-42 of SEQ ID NO: 1.

In some embodiments, the C-terminal loop sequence in the TRAF6/TRAF2 interacting peptide segment is located at positions corresponding to positions 144-184 of SEQ ID NO: 1.

In some embodiments, the Thr9 peptide segment comprises an amino acid sequence corresponding to positions 1-45 of SEQ ID NO: 1 or an amino acid sequence having at least 70% identity to said sequence. In some examples, the Thr9 peptide segment comprises an amino acid sequence selected from the group consisting of SEQ ID NOs: 23-34.

In some embodiments, the dimerization-core peptide segment comprises an amino acid sequence corresponding to positions 46-103 of SEQ ID NO: 1 or an amino acid sequence having at least 70% identity to said sequence. In some examples, the dimerization-core peptide segment comprises an amino acid sequence selected from the group consisting of SEQ ID NOs: 35-46.

In some embodiments, the TRAF6/TRAF2 interacting peptide segment comprises an amino acid sequence corresponding to positions 104-184 of SEQ ID NO: 1 or an amino acid sequence having at least 70% identity to said sequence. In some examples, the TRAF6/TRAF2 interacting peptide segment comprises an amino acid sequence selected from the group consisting of SEQ ID NOs: 47-58.

In some embodiments, the C-terminal loop sequence in the TRAF6/TRAF2 interacting peptide segment comprises an amino acid sequence corresponding to positions 144-184 of SEQ ID NO: 1 or an amino acid sequence having at least 70% identity to said sequence. In some examples, the C-terminal loop sequence in the TRAF6/TRAF2 interacting peptide segment comprises an amino acid sequence selected from the group consisting of SEQ ID NOs: 59-70.

In one embodiment, the TIFA peptide fragment of the present invention is a F1-F2 peptide fragment comprising the Thr9 peptide segment and the dimerization-core peptide segment, wherein the C-terminus of the Thr9 peptide segment is linked to the N-terminal of the dimerization-core peptide segment, lacking the TRAF 6 interacting peptide segment. In some examples, the F1-F2 peptide fragment comprises an amino acid sequence selected from the group consisting of SEQ ID NO:71-82.

In one embodiment, the TIFA peptide fragment of the present invention is a F2-F3 peptide fragment comprising the dimerization-core peptide segment and the TRAF 6 interacting peptide segment, wherein the C-terminus of the dimerization-core peptide segment is linked to the N-terminal of the TRAF 6 interacting peptide segment, lacking the Thr9 peptide segment. In some examples, the F2-F3 peptide fragment comprises an amino acid sequence selected from the group consisting of SEQ ID NO: 83-94.

In another aspect, the present disclosure provides a recombinant nucleic acid comprising a nucleotide sequence encoding any of the peptides as described herein. Such a nucleic acid may be a vector comprising the coding sequence noted herein. In some examples, the vector is a viral vector.

Any of the peptides or nucleic acids may be formulated to form a composition, for example, a pharmaceutical composition, which further comprises a physiologically acceptable carrier.

Also provided herein is a method for treating a disease or condition associated with TIFA activation, comprising administering to the subject an effective amount of any of the peptides or any of the nucleic acids encoding such as described herein, or a composition comprising such. The disease or condition associated with TIFA activation can be a cancer or an inflammatory disorder associated with TIFA activation, or a cancer or an inflammatory disorder associated cytokine-stimulated NF-κB activation. In some embodiments, the subject is afflicted with cancer and the peptide fragment, the encoding nucleic acid and the composition comprising the peptide or the encoding nucleic acid is administered in combination with an anti-cancer treatment. In particular, the peptide fragment, the encoding nucleic acid and the composition is administered in an amount effective in enhancing cytotoxocity of the anti-cancer treatment. In some embodiments, the anti-cancer treatment involves administration of an anti-cancer agent or irradiation. An anti-cancer agent includes, but is not limited to a chemotherapeutic agent and a molecularly targeted drug. Examples of an anti-cancer agent are etoposide, idarubicin, cytarabine, sorafenib, regorafenib, bleomycin, bortezomib, busulfan, and obatoclax.

It is also found in this invention that the TIFA protein expression level is correlated with prognosis of leukemia. In particular, the present invention provides a method for predicting the prognosis of leukemia comprising collecting a blood sample obtained from a leukemia patient, measuring the expression level of TRAP-interacting protein with an FHA domain (TIFA) in the blood sample, and determining the prognosis of leukemia in the patient based on the expression level of TIFA in the blood sample, wherein an elevated level of TIFA in the blood sample indicates poor prognosis.

Further provided is a method for inhibiting cytokine-stimulated NF-κB activation in a subject, comprising administering to the subject an effective amount of a TIFA antagonist. Examples of a TIFA antagonist includes an interfering nucleic acid targeting TIFA or a TIFA dominant negative inhibitor e.g. a TIFA peptide fragment as described herein. In some examples, the subject to be treated may be a human patient having a disease or condition associated with cytokine-stimulated NF-κB activation. Such a disease or condition may be a caner or an inflammatory disorder due to cytokine-stimulated NF-κB activation.

Specifically, the cancer to be treated in the present invention is associated with chronic inflammation or inflammatory diseases. Particular examples of cancer to be treated in the present invention include but are not limited to a hematologic cancer (e.g. leukemia or lymphoma), liver cancer, gastric intestinal cancer (e.g. stomach cancer or colorectal cancer), lung cancer, prostate cancer, pancreas cancer, ovarian and breast cancer. In some embodiments, a TIFA antagonist as described herein can be administrated with an anti-cancer agent which provides a synergistic effect in treating cancer as compared to treatment with the anti-cancer agent alone or in combination with an anti-inflammation agent e.g. entanercept, anti-survival targeted drug e.g. ABT-263, and anti-NF-κB agent e.g. bortezomib.

In some embodiments, the inflammatory disorder is hepatitis, atherosclerosis, pulmonary arterial hypertension, cardiomyopathy, rheumatoid arthritis, inflammatory bowel disease and Fabry disease.

Also within the scope of the present disclosure are pharmaceutical compositions for use in treating a disease related to cytokine-stimulated NF-κB activation, the composition comprising any of the peptides described herein or nucleic acids encoding such, and a pharmaceutically acceptable carrier. Further described herein are uses of a peptide described herein or a nucleic acid encoding such for manufacturing a medicament for use in the method as described herein e.g. for treating a disease related to cytokine-stimulated NF-κB activation.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

(FIG. 1A) In vitro kinase assay for TIFA phosphorylation. Top panel, western blot analysis of lysates from 293T cells transfected with Flag-tagged Aurora A (Flag-Aurora A) or Aurora A siRNA (siAurora A), or treated with Aurora A inhibitors (VX-680 and MK-5108). Aurora A pT288 represents the activated kinase (18). Left panel, in vitro kinase assay using recombinant TIFA wild-type (WT) and the unphosphorylatable T9A mutant proteins incubated with lysates from 293T cells treated with Aurora A inhibitors and TNF-α in the presence of [γ-$^{32}$P]ATP. WCE, whole cell extract; Si, Aurora A siRNA; VX, VX680; MK, MK5108; PPTase, alkaline phosphatase. Right panel, quantification and statistical analysis of three independent experiments. (FIG. 1B) Upper panel, immunoprecipitation of Aurora A from 293T cell lysates transfected with HA-tagged TIFA under different time courses of TNF-α stimulation. Lower panel, western blot analysis of total lysates used in upper panel. S, supernatant; P, precipitate. (FIG. 1C) Left panel, western blot analyzsis of lysates from 293T cells transfected with Flag-tagged Aurora A and TIFA siRNA. Right panel, the same as left panel except that U937 cells transfected with TIFA siRNA and treated with 10 ng/mL TNF-α for 30 min were examined. (FIG. 1D) The same as (FIG. 1C), except that the treated cells were additionally transfected with pNF-κB-Luc plasmid and analyzed by luciferase reporter assay for NF-κB activity. Plots represent relative luminance unit (RLU) normalized to non transfection or non TNF-α-stimulated controls.

(FIG. 3A) Time courses of cell viabilities upon TIFA silencing for four AML lines were examined by the WST-1 assay. Plots represent relative cell viabilities normalized to day zero from three independent experiments. (FIG. 3B) Plots represent relative cell viabilities normalized to mock controls at the 4$^{th}$ day from experiments in (FIG. 3A) and the corresponding experiments with VX680 treatment. (FIG. 3C) AML lines used in (FIG. 3A) and (FIG. 3B) were analyzed by WST-1 assay for cell viabilities under chemo drugs treatment. Plots represent calculated IC50 of chemo drugs. siCon, control siRNA; siTIFA, TIFA siRNA.

(FIG. 4A) Time courses of cell viabilities upon TIFA silencing for 8 AML PBMCs were examined by the WST-1 assay. Plots represent relative cell viabilities normalized to day zero. (FIG. 4B) Plots represent relative cell viabilities normalized to mock controls at the 4$^{th}$ day from the experiments in (FIG. 4A) and the corresponding experiments for normal PBMCs and with VX680 treatment (n=8 in each group). (FIG. 4C) Western blot analysis for the levels of pro-survival factors in 8 AML PBMCs upon TIFA silencing and 8 normal PBMCs. (FIG. 4D) AML PBMCs used in (FIG. 4A) and (FIG. 4B) were analyzed by WST-1 assay for cell viabilities under chemo drug treatments. Plots represent calculated IC50 of chemo drugs. (FIG. 4E) Four AML PBMCs (AML #9, 10, 13, and 15) were treated with 10 μM etoposide, 10 nM idarubicin, or 10 μM cytarabine upon TIFA silencing or VX680 treatment, and analyzed by flow cytometry. Plots represent percentages of cells with annexin V and propidium iodide positive staining. Horizontal bars, medium value, siCon, control siRNA; siTIFA, TIFA siRNA.

(FIG. 5A) Plots represent calculated IC50 of chemo drugs for AML lines under TIFA silencing and over-expression of siRNA-resistant (siR) TIFA wild-type (WT) or T9A mutant. (FIG. 5B) Schematic representation of dominant-negative constructs of TIFA. AML lines were respectively infected with pseudotyped retroviruses carrying these constructs to generate stable cells. 2Myc, 2 consecutive Myc-tags. (FIG. 5C) Lysates from U937 cells stably expressing TIFA fragments shown in (FIG. 5B) were immunoprecipitated using anti-Myc immunobeads and analyzed by western blot. (FIG. 5D) Cells used in (FIG. 5C) were additionally transfected with pNF-κB-Luc plasmid, treated with 10 ng/mL TNF-α for 30 min, and analyzed by luciferase reporter assay for NF-κB activity. Luciferase activities were normalized to non TNF-α-stimulated control. Plots represent relative luminance unit (RLU) acquired from three independent experiments. (FIG. 5E) Lysates in (FIG. 5D) were analyzed by western blot analysis for levels of NF-κB signaling factors. (FIG. 5F) AML lines stably expressing TIFA fragments described in (FIG. 5B) were treated with chemo drugs in dose-dependent manners and analyzed by WST-1 assay for cell viabilities. Plots represent calculated IC50 values of chemo drugs acquired from three independent experiments. siCon, control siRNA; siTIFA, TIFA siRNA.

(FIG. 6A) Conditioned media collected from 10 μM cytarabine treated U937 stable cells used in FIG. 5F were analyzed by cytokine-antibody array for cytokine secretion profile. Boxed cytokines were quantified and shown in the right panel. (FIG. 6B) Secretion of leukemic cytokines from cells used in (FIG. 6A) was quntitatively analyzed by ELISA. Amounts of cytokines in condition medium were normalized to PBS control, and plots represent relative secretion of cytokines acquired from three independent experiments. siTIFA, TIFA siRNA transfection. (FIG. 6C) U937 cells used in (FIG. 6A) were analyzed by WST-1 assay for cell viabilities in the presence of 10 ng/mL TNF-α and 10 μM cytarabine. Results were normalized to day zero, and plots represent time course of relative cell viabilities. (FIG. 6D) U937 cells used in (FIG. 6A) were analyzed by WST-1 assay for cell viabilities in the presence 5 μg/mL etanercept, 50 nM bortezomib, or 1 μM ABT-263 together with 10 μM cytarabine. Results were normalized to day zero, and plots represent time course of relative cell viabilities acquired from three independent experiments. (FIG. 6E) Upper panel, experimental procedure for growth of myeloid sarcoma in nude mice. Mice were subcutaneously injected with retrovirally transduced U937 cells used in (FIG. 6A) and treated with cytarabine. Time course of tumor volumes. FIG. 6 (F) Upper panel, experimental procedure for growth of myeloid sarcoma in nude mice. Mice were subcutaneously injected with retrovirally transduced U937 cells used in (FIG. 6A), and intraperitoneally treated with 5 mg/kg etanercept, 0.5 mg/kg bortezomib, or 50 mg/kg ABT-263 in combination with 50 mg/kg cytarabine. Time course of tumor volumes (n=4 in each group). (FIG. 6G) The same as (FIG. 6E), except that U937 stable cells were injected via IVC, and that BM engraftment was analyzed. Left panel, BM cells from treated mice were assessed by flow cytometry using anti-human CD45 and CD33 antibodies. Right panel, plots of percentages of human CD45$^+$CD33$^+$ cells analyzed in left panel (n=7 in each group). Horizontal bars, medium value. SC, subcutaneous injection; IP, intraperitoneal injection; IVC, injection of cells via inferior vena cava.

Figure 8:
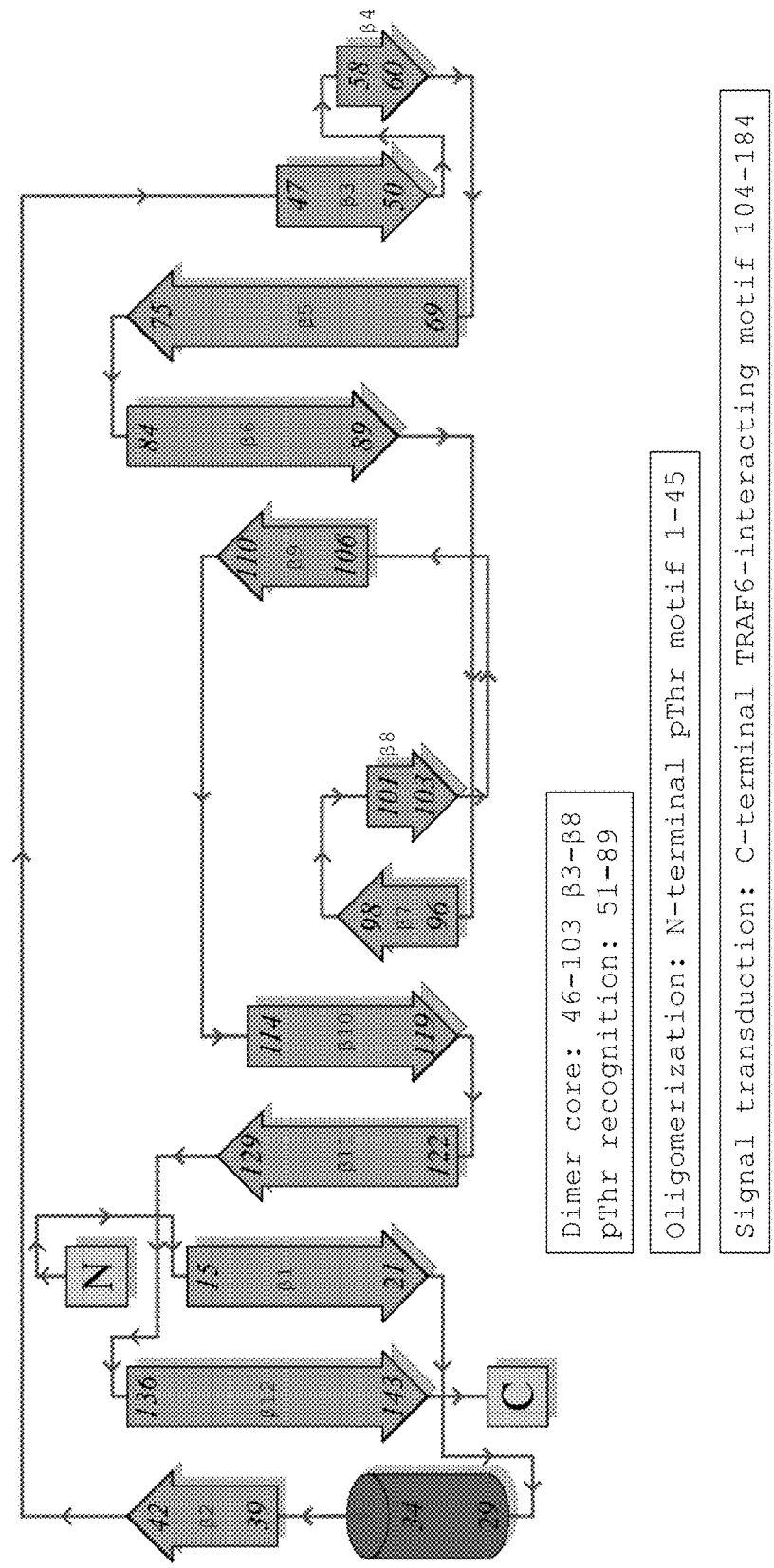

FIG. 8 shows the topological representation of β-sandwich architecture of TIFA formed by twelve-stranded β-sheets.

DETAILED DESCRIPTION OF THE INVENTION

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a component" includes a plurality of such components and equivalents thereof known to those skilled in the art.

The term "comprise" or "comprising" is generally used in the sense of include/including which means permitting the presence of one or more features, ingredients or components. The term "comprise" or "comprising" encompasses the term "consists" or "consisting of."

As used herein, the term "polypeptide" refers to a polymer composed of amino acid residues linked via peptide bonds. The term "peptide" refers to a relatively short polypeptide composed of linked amino acids e.g., 200 amino acids or less, 175 amino acids or less, 150 amino acids or less e.g. 140 or less, β0 or less, 120 or less, 110 or less, 100 or less, 90 or less, 80 or less, 70 or less, 60 or less, 50 or less or 40 or less amino acids in length.

As used herein, the term "about" or "approximately" refers to a degree of acceptable deviation that will be understood by persons of ordinary skill in the art, which may vary to some extent depending on the context in which it is used. In general, "about" or "approximately" may mean a numeric value having a range of ±10% around the cited value.

As used herein, "corresponding to," refers to a residue at the enumerated position in a protein or peptide, or a residue that is analogous, homologous, or equivalent to an enumerated residue in a protein or peptide.

As used herein, the term "substantially identical" refers to two sequences having more than 70%, preferably 75%, more preferably 80%, even more preferably 85%, still even more preferably 90%, and most preferably 95% or 100% homology.

1. TIFA Protein

Figure 7:
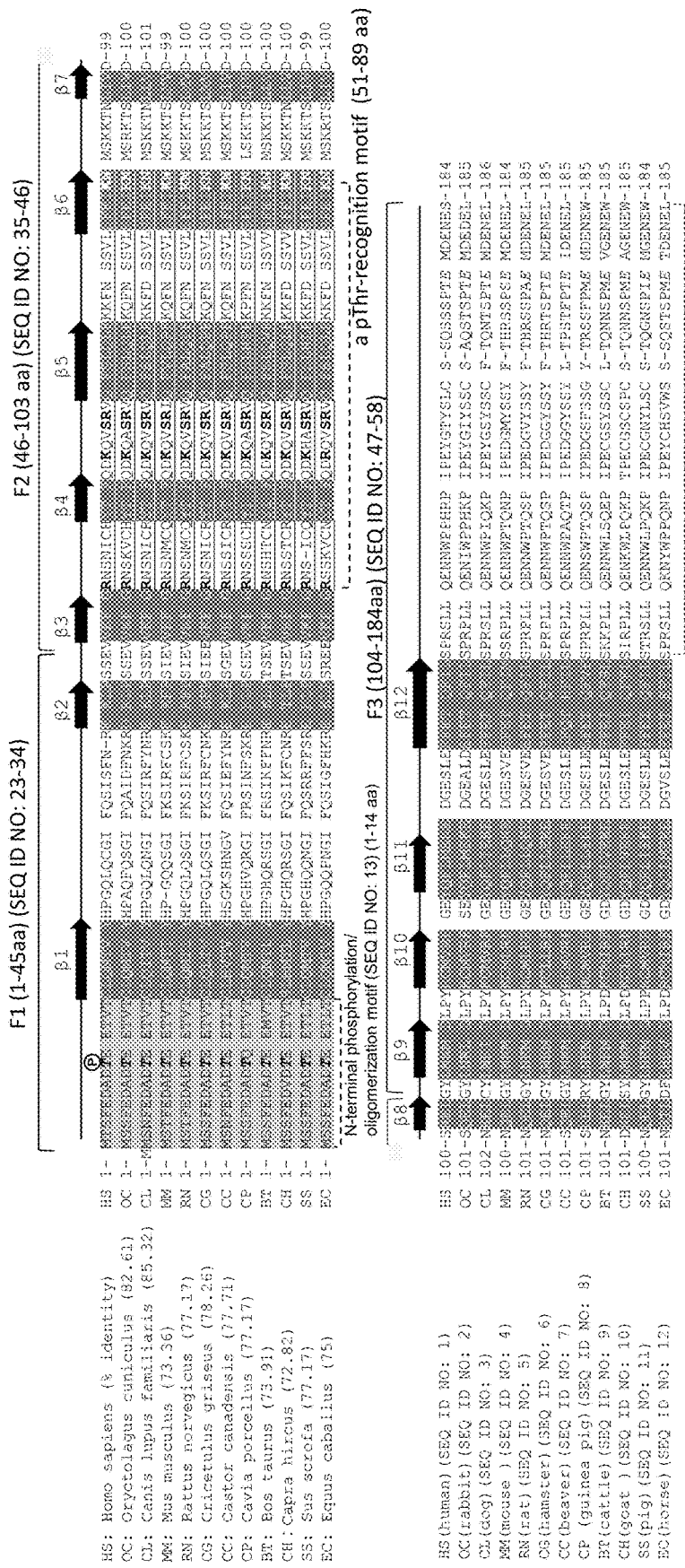
FIG. 7 shows the alignment of the amino acid sequences of TIFA from different species, including SEQ ID NO: 1 from *Homo sapiens*, SEQ ID NO: 2 from *Oryctolagus cuniculus*, SEQ ID NO: 3 from *Canis lupus familiaris*, SEQ ID NO: 4 from *Mus musculus*, SEQ ID NO: 5 from *Rattus norvegicus*, SEQ ID NO: 6 from *Cricetulus griseus*, SEQ ID NO: 7 from *Castor Canadensis*, SEQ ID NO: 8 from *Cavia porcellus*, SEQ ID NO: 9 from *Bos Taurus*, SQE ID NO: 10 from *Capra hircus*, SQE ID NO: 11 from *Sus scrofa*, and SEQ ID NO: 12 from *Equus caballus*, indicating the F1 fragment (positions 1-45, comprising the N-terminal phosphorylation/oligomerization motif and β1-β1 strands), F2 fragment (positions 46-103, comprising β3-β8 strands) and F3 fragment (positions 104-184, comprising β9-β12 strands), as well as a pThr-recognition motif located in F2 domain (e.g. at about positions 51-89 of SEQ ID NO: 1, underlined residues) and a C-terminal loop sequence in F3 domain (e.g. at about positions 144-184 of SEQ ID NO: 1) in certain embodiments.

The terms "TRAF-interacting forkhead-associated (FHA) protein A", "TRAF-interacting protein with an FHA domain", "TIFA", "TIFA protein" and "TIFA polypeptide" as used herein are interchangeable. A TIFA protein as described herein can include the amino acid sequence set forth in SQE ID NO: 1 (human TIFA), and also can include those comprising an amino acid sequence which (i) are substantially identical to the amino acid sequences constituting any TIFA protein as described herein; and (ii) are encoded by a nucleic acid sequence capable of hybridizing under at least moderately stringent conditions to any nucleic acid sequence encoding any TIFA protein set forth herein or capable of hybridizing under at least moderately stringent conditions to any nucleic acid sequence encoding any TIFA protein set forth herein, but for the use of synonymous codons (e.g. a codon which does not have the identical nucleotide sequence, but which encodes the identical amino acid). A TIFA protein as described herein includes human TIFA and its homologues from vertebrates, and particularly those homologues from mammals. Specifically, a TIFA protein as described herein includes the TIFA amino acid sequences from human (SEQ ID NO: 1), the TIFA amino acid sequences from other mammals (SEQ ID NOs: 2 to 12) that has at least 70%, at least 75% or at least 80% identity to SEQ ID NO: 1 (see FIG. 7). A TIFA protein as described herein further includes any recombinantly (engineered)-derived TIFA polypeptides encoded by cDNA copies of the natural polynucleotide sequence encoding TIFA.

In structure, it is disclosed herein that a TIFA protein as used herein includes, from N-terminal to C-terminal, (i) a F1 domain, i.e. a Thr9 peptide segment, comprising a N-terminal phosphorylation/oligomerization motif, and optional β1-β2 strands; (ii) a F2 domain, i.e. a dimerization-core peptide segment, comprising six β strands that includes β3-β8 strands; and (iii) a F3 domain, i.e. a TRAF6/TRAF2 interacting peptide fragment, comprising four β strands that includes β9-β12 strands and a C-terminal loop sequence. Table 1 describes the F1, F2 and F3 domains and their features in structure.

TABLE 1

| Domains | Features |
|---------|----------|
| F1 | a N-terminal phosphorylation/oligomerization motif<br>$MX_1X_2FEDX_3DTX_4EX_5X_6T$ (SEQ ID NO: 13)<br>    $X_1$ S or T<br>    $X_2$ S, T or N<br>    $X_3$ A or V<br>    $X_4$ E or Q<br>    $X_5$ T or M<br>    $X_6$ V or L |
| β1 strand (optional) | β1 motif $X_1LX_2X_3TX_4Y$ (SEQ ID NO: 14)<br>    $X_1$ C or S<br>    $X_2$ Q or H<br>    $X_3$ M, I, L or V<br>    $X_4$ V, I or L |
| β2 strand (optional) | β2 motif $X_1X_2X_3P$ (SEQ ID NO: 15)<br>    $X_1$ E or D<br>    $X_2$ K or T<br>    $X_3$ L or F |

TABLE 1-continued

| Domains | Features | |
|---|---|---|
| F2 | β3 strand | β3 motif VKFG (SEQ ID NO: 16) |
| | β4 strand | β4 motif YX₁F |
| | | X₁ T or I |
| | β5 strand | β5 motif QFX₁LX₂X₃F (SEQ ID NO: 17) |
| | | X₁ S, V or A |
| | | X₂ Q or H |
| | | X₃ L, P or V |
| | β6 strand | β6 motif SFEIKN (SEQ ID NO: 18) |
| | β7 strand | β7 motif LIV |
| | β8 strand | β8 motif X₁X₂L |
| | | X₁ R, Q, or K |
| | | X₂ E or T |
| F3 | β9 strand | β9 motif LX₁KX₂D (SEQ ID NO: 19) |
| | | X₁ N or H |
| | | X₂ M, L, V or I |
| | β10 strand | β10 motif X₁CX₂X₃RF (SEQ ID NO: 20) |
| | | X₁ R or K |
| | | X₂ M or L |
| | | X₃ V, L or I |
| | β11 strand | β11 motif YQX₁LX₂X₃X₄E (SEQ ID NO: 21) |
| | | X₁ F or I |
| | | X₂ M, L, V, or I |
| | | X₃ E or Q |
| | | X₄ K or R |
| | β12 strand | β12 motif X₁FX₂X₃X₄FX₅X₆ (SEQ ID NO: 22) |
| | | X₁ F, or S |
| | | X₂ E or Q |
| | | X₃ T or I |
| | | X₄ Q, H, or E |
| | | X₅ I, V, S, or F |
| | | X₆ L, M, or F |

Each of the β strands can be connected to the next in sequence from N-terminal to C-terminal by loop sequences that may vary in length and have a relatively low level of sequence homology. Specifically, each of the above-mentioned motifs in a TIFA protein can be approximately located at positions as follows: the N-terminal Thr9-phorsphorylation motif is located at positions corresponding to positions 1-14 of SEQ ID NO: 1; the β1 motif is located at positions corresponding to positions 15-21 of SEQ ID NO: 1; the β2 motif is located at positions corresponding to positions 39-42 of SEQ ID NO: 1; the β3 motif is located at positions corresponding to positions 47-50 of SEQ ID NO: 1; the β4 motif is located at positions corresponding to positions 58-60 of SEQ ID NO: 1; the β5 motif is located at positions corresponding to positions 69-75 of SEQ ID NO: 1; the β6 motif is located at positions corresponding to positions 84-89 of SEQ ID NO: 1; the β7 motif is located at positions corresponding to positions 96-98 of SEQ ID NO: 1; the β8 motif is located at positions corresponding to positions 101-103 of SEQ ID NO: 1; the β9 motif is located at positions corresponding to positions 106-110 of SEQ ID NO: 1; the β10 motif is located at positions corresponding to positions 114-119 of SEQ ID NO: 1; the β11 motif is located at positions corresponding to positions 122-129 of SEQ ID NO: 1; and/or the β12 motif is located at positions corresponding to positions 136-143 of SEQ ID NO: 1. In some embodiments, the C-terminal loop sequence in the TRAF6/TRAF2 interacting peptide segment is located at positions corresponding to positions 144-184 of SEQ ID NO: 1. In addition, each of the F1, F2 and F3 domains can be approximately located at positions as follows: F1 domain corresponds to positions 1-45 of SEQ ID NO: 1; F2 domain corresponds to positions 46-103 of SEQ ID NO: 1; and/or F3 domain corresponds to positions 104-184 of SEQ ID NO: 1.

In function, a TIFA protein can be activated by phosphorylation upon stimulation by cytokine, bacterial-derived sugar (23,26), or inflammation condition (24), e.g. TNF-α and thus triggers TIFA oligomerization which leads to interaction with TRAF6 or TRAF2 and then incudes NF-κB activation. Specifically, it is disclosed herein that the dimerization-core segment (F2 domain) enables formation of an intrinsic dimer between two TIFA monomers. In addition, the Thr9 peptide segment (H domain) can be phosphorylated at the Thr9 residue in the N-terminal phosphorylation/oligomerization motif (SEQ ID NO: 13) by kinase e.g. Aurora A kinase, and once the phosphorylation occurs, the phosphorylated Thr9 residue in the N-terminal phosphorylation/oligomerization motif in F1 domain can be recognized by a pThr-recognition motif located in F2 domain (e.g. at about positions 51-89 of SEQ ID NO: 1, see FIG. 7-8), thus triggering TIFA's oligomerization (e.g. one TIFA dimer is associated with additional one or more TIFA dimers, via intermolecular interaction between the N-terminal phosphorylation/oligomerization motif in F1 domain and the pThr-recognition motif in F2 domain). The resultant TIFA oligomer, formed by at least two TIFA dimers or more, can subsequently interact with tumor necrosis factor receptor-associated factor 6 (TRAF6) or TRAF2 via the TRAF6/TRAF2 interacting peptide fragment (F3 domain) in each of the TIFA monomer of the TIFA oligomer, thereby promoting oligomerization of TRAF2/TRAF6. The functional characteristics of each of F1, F2 and F3 domains can be assayed via a method known in the art. For example, phosphorylation at Thr9 can be analyzed by in vitro kinase assay (20), dimerization of TIFA monomers via F2 domain can be determined via native PAGE (20,23,24), and interaction of TIFA oligomers with TRAF6 or TRAF2 via the F3 domain can be confirmed by immunoprecipitation.

In some embodiments, the Thr9 peptide segment (F1 domain) comprises an amino acid sequence corresponding to positions 1-45 of SEQ ID NO: 1 (i.e. SEQ ID NO: 23) or an amino acid sequence having at least 70%, 80% or 90% identity to said sequence. In some examples, the Thr9 peptide segment comprises an amino acid sequence selected from the group consisting of SEQ ID NOs: 23-34.

In some embodiments, the dimerization-core peptide segment comprises an amino acid sequence corresponding to positions 46-103 of SEQ ID NO: 1 (i.e. SEQ ID NO: 35) or an amino acid sequence having at least 70%, 80% or 90% identity to said sequence. In some examples, the dimerization-core peptide segment comprises an amino acid sequence selected from the group consisting of SEQ ID NOs: 35-46.

In some embodiments, the TRAF6/TRAF2 interacting peptide segment comprises an amino acid sequence corresponding to positions 104-184 of SEQ ID NO: 1 (i.e. SEQ ID NO: 47) or an amino acid sequence having at least 70%, 80% or 90% identity to said sequence. In some examples, the TRAF6/TRAF2 interacting peptide segment comprises an amino acid sequence selected from the group consisting of SEQ ID NOs: 47-58.

In some embodiments, the C-terminal loop sequence in the TRAF6/TRAF2 interacting peptide segment comprises an amino acid sequence corresponding to positions 144-184 of SEQ ID NO: 1 or an amino acid sequence having at least 70% identity to said sequence. In some examples, the C-terminal loop sequence in the TRAF6/TRAF2 interacting peptide segment comprises an amino acid sequence selected from the group consisting of SEQ ID NOs: 59-70.

2. TIFA Peptide Fragments and Compositions Comprising Such

TIFA peptide fragments (or interchangeably called TIFA fragments) refer to non-naturally occurring truncated fragments derived from TIFA, or functional variants thereof. Such peptides are different from a naturally occurring full-length TIFA protein at least in that such peptide fragments act as a dominant negative peptide of the full-length active TIFA protein, competing with the active TIFA protein and thus reducing the effect of the active TIFA protein. In particular, the TIFA peptide fragments can exhibit inhibitory effects on cytokine-induced NF-κB activation. Therefore, the TIFA peptide fragments can be deemed as TIFA antagonists useful in suppressing TIFA-mediated signaling pathway and thus benefit in treatment of disease and disorder associated with abnormal activation of TIFA.

According to the present invention, a TIFA peptide fragment acting as a dominant negative peptide of the full-length active TIFA protein must include a dimerization-core peptide segment (F2 domain), which can either be connected with a Thr9 peptide segment (F1 domain) at the N-terminal or a TRAF6/TRAF2 interacting peptide segment (F3 domain) at the C-terminal. In one embodiment, a TIFA peptide fragment of the present invention includes a Thr9 peptide segment (F1 domain) and a dimerization-core peptide segment (F2 domain), wherein the C-terminus of the Thr9 peptide segment is linked to the N-terminal of the dimerization-core peptide segment, lacking the TRAF6/TRAF2 interacting peptide segment (F3 domain). In some examples, the TIFA peptide fragment of the present invention is selected from the group consisting of SEQ ID NO: 71-82.

In another embodiment, a TIFA peptide fragment of the present invention includes a dimerization-core peptide segment (F2 domain) and a TRAF6/TRAF2 interacting peptide segment (F3 domain), wherein the C-terminus of the dimerization-core peptide segment is linked to the N-terminal of the TRAF6/TRAF2 interacting peptide segment, lacking the Thr9 peptide segment (F1 domain). In some examples, the TIFA peptide fragment of the present invention is selected from the group consisting of SEQ ID NO: 83-94.

In additional embodiments, the TIFA fragment as described herein may be a variant of a TIFA fragment with one or more mutations. It is understandable that a polypeptide may have a limited number of changes or modifications that may be made within a certain portion of the polypeptide irrelevant to its activity or function and still result in a variant with an acceptable level of equivalent or similar biological activity or function. In particular, the TIFA fragment of the present invention exhibits the activities to reduce TIFA activation and the subsequent NF-κB activation. Therefore, it is possible to identify the amino acid positions that are essential or non-essential to the activities of the TIFA fragment of the present invention to reduce TIFA activation/NF-κB activation. Analysis of TIFA activation can be performed by for example in vitro kinase assay, native PAGE, immunoprecipitation or luciferase reporter assay. Cells stimulated by inflammatory cytokines or pathological stresses lead to NF-κB activation which can be measured by luciferase levels using a NF-κB reporter system, for example. A test TIFA fragment can be determined to be effective in reducing TIFA activation/NF-κB activation if the level of the TIFA activation/NF-κB activation decreases under overexpression of a test TIFA fragment as compared with that without overexpression of the test TIFA fragment. In some examples, the amino acid residue mutations are conservative amino acid substitution, which refers to the amino acid residue of a similar chemical structure to another amino acid residue and the polypeptide function, activity or other biological effect on the properties smaller or substantially no effect. Variants can be prepared according to methods for altering polypeptide sequence known to one of ordinary skills in the art such as those found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989. For example, conservative substitutions of amino acids include substitutions made amongst amino acids within the following groups: (i) A, G; (ii) S, T; (iii) Q, N; (iv) E, D; (v) M, I, L, V; (vi) F, Y, W; and (vii) K, R, H.

The TIFA fragment of the present invention may be produced by chemical synthesis using techniques well known in the chemistry of proteins such as solid phase synthesis or synthesis in homogenous solution.

As an alternative, the TIFA fragment of the present invention can be prepared using recombinant techniques. In this regard, a recombinant nucleic acid comprising a nucleotide sequence encoding a TIFA fragment of the present invention and host cells comprising such recombinant nucleic acid are provided. The host cells may be cultured under suitable conditions for expression of the polypeptide of interest. Expression of the polypeptides may be constitutive such that they are continually produced or inducible, requiring a stimulus to initiate expression. In the case of inducible expression, protein production can be initiated when desired by, for example, addition of an inducer substance to the culture medium, for example, isopropyl β-D-1-thiogalactopyranoside (IPTG) or methanol. Polypeptide can be recovered and purified from host cells by a number of techniques known in the art, for example, chromatography e.g., FPLC or affinity columns.

The term "polynucleotide" or "nucleic acid" can refer to a polymer composed of nucleotide units. Polynucleotides include naturally occurring nucleic acids, such as deoxyribonucleic acid ("DNA") and ribonucleic acid ("RNA") as well as nucleic acid analogs including those which have non-naturally occurring nucleotides. Polynucleotides can be synthesized, for example, using an automated DNA synthesizer. The term "nucleic acid" typically refers to large polynucleotides. It will be understood that when a nucleotide sequence is represented by a DNA sequence (i.e., A, T, G, C), this also includes an RNA sequence (i.e., A, U, G, C) in which "U" replaces "T." The term "cDNA" refers to a DNA that is complementary or identical to an mRNA, in either single stranded or double stranded form.

The term "complementary" refers to the topological compatibility or matching together of interacting surfaces of two polynucleotides. Thus, the two molecules can be described as complementary, and furthermore the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'."

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "recombinant nucleic acid" refers to a polynucleotide or nucleic acid having sequences that are not naturally joined together. A recombinant nucleic acid may be present in the form of a vector. "Vectors" may contain a given nucleotide sequence of interest and a regulatory sequence. Vectors may be used for expressing the given nucleotide sequence (expression vector) or maintaining the given nucleotide sequence for replicating it, manipulating it or transferring it between different locations (e.g., between different organisms). Vectors can be introduced into a suitable host cell for the above-mentioned purposes. A "recombinant cell" refers to a host cell that has had introduced into it a recombinant nucleic acid. "Transformation" refers to a genetic change in a cell following incorporation of new DNA (i.e., DNA exogenous to the cell). "Transfection" means the process of a cell being transferred with exogenous DNA. "Transduction" can specifically mean the process whereby exogenous DNA is introduced into a cell via a viral vector. "A transformed cell" mean a cell into which has been introduced, by means of recombinant DNA techniques, a DNA molecule encoding a protein of interest.

Vectors may be of various types, including plasmids, cosmids, fosmids, episomes, artificial chromosomes, phages, viral vectors, etc. Typically, in vectors, the given nucleotide sequence is operatively linked to the regulatory sequence such that when the vectors are introduced into a host cell, the given nucleotide sequence can be expressed in the host cell under the control of the regulatory sequence. The regulatory sequence may comprise, for example and without limitation, a promoter sequence (e.g., the cytomegalovirus (CMV) promoter, simian virus 40 (SV40) early promoter, T7 promoter, and alcohol oxidase gene (AOX1) promoter), a start codon, a replication origin, enhancers, an operator sequence, a secretion signal sequence (e.g., α-mating factor signal) and other control sequence (e.g., Shine-Dalgarno sequences and termination sequences). Preferably, vectors may further contain a marker sequence (e.g., antibiotic resistant marker sequence) for the subsequent screening procedure. For purpose of protein production, in vectors, the given nucleotide sequence of interest may be connected to another nucleotide sequence other than the above-mentioned regulatory sequence such that a fused polypeptide is produced and beneficial to the subsequent purification procedure. Said fused polypeptide includes a tag for purpose of purification, which can be bound to an end of the polypeptide and preferably is small in size that does not affect the desired activity of the polypeptide. Specifically, the tag is of about 30 amino acid residues or less, particularly about 20 amino acid residues or less, more particularly about 10 amino acid residues or less in length; or has a molecular weight of about 10 kDa or less, particularly about 5 kDa or less, more particularly about 2.5 kDa or less. Examples of such tag include, but is not limited to a six (6) to fourteen (14) His-tag or a one (1) to two (2) Myc-tag. The tag may be connected to an N-terminus or a C-terminus of the polypeptide. In some embodiments, the tag may be cleavable in vitro or in vivo. The in vitro or in vivo cleaving may be processed by a protease.

In some embodiments, the peptide of the present invention can be said to be "isolated" or "purified" if it is substantially free of cellular material or chemical precursors or other chemicals that may be involved in the process of peptide preparation. It is understood that the term "isolated" or "purified" does not necessarily reflect the extent to which the peptide has been "absolutely" isolated or purified e.g. by removing all other substances (e.g., impurities or cellular components). In some cases, for example, an isolated or purified peptide includes a preparation containing the peptide having less than 50%, 40%, 30%, 20% or 10% (by weight) of other proteins (e.g. cellular proteins), having less than 50%, 40%, 30%, 20% or 10% (by volume) of culture medium, or having less than 50%, 40%, 30%, 20% or 10% (by weight) of chemical precursors or other chemicals involved in synthesis procedures. The term "isolated" or "purified" can also apply in the nucleic acid of the present invention.

According to the present invention, an effective amount of the active ingredient (TIFA fragment) may be formulated with a physiologically acceptable carrier into a composition of an appropriate form for the purpose of delivery and absorption. The composition of the present invention particularly comprises about 0.1% by weight to about 100% by weight of the active ingredient, wherein the percentage by weight is calculated based on the weight of the whole composition. In some embodiments, the composition of the present invention can be a pharmaceutical composition or medicament for treatment.

As used herein, "physiologically acceptable" means that the carrier is compatible with the active ingredient in the composition, and preferably can stabilize said active ingredient and is safe to the receiving individual. Said carrier may be a diluent, vehicle, excipient, or matrix to the active ingredient. Some examples of appropriate excipients include lactose, sucrose, dextrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of the composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (e.g. with a pH value of 3 to 9) as needed. Preparation of an appropriate parenteral composition under sterile conditions may be accomplished with standard pharmacological techniques well known to persons skilled in the art.

In some particular embodiments, a viral vector carrying a nucleic acid encoding the peptide of the present invention is administered to a subject in need. Numerous viral vectors are well known in the art, including, for example, retrovirus, lentivirus, adenovirus, adeno-associated virus, herpes simplex virus (HSV), cytomegalovirus (CMV), vaccinia and poliovirus vectors. Preferably, a replication-deficient virus is used as the viral vector, such that transformation of the recombinant cell line with the recombinant viral vector will not result in production of replication-competent viruses, e.g., by homologous recombination of the viral sequences of the recombinant cell line into the introduced viral vector. A DNA of the present invention may also be administered using a non-viral vector, for instance, as a DNA- or RNA-liposome complex formulation. Such complexes comprise a mixture of lipids which bind to nucleic acids (DNA or RNA), providing a hydrophobic coat which allows the genetic material to be delivered into cells.

3. Therapeutic uses of TIFA Peptide Fragments as TIFA Antagonists for Treating TIFA-Associated Diseases TIFA is involved in NF-κB activation by various stimulation such as inflammatory cytokines or lipopolysaccharide (LPS). Unexpectedly, it is found in this invention that the TIFA fragments described herein are capable of inhibiting TIFA activation and the resultant NF-κB activation (TIFA activation/NF-κB activation). Therefore, any of the TIFA fragments described herein, which possess inhibitory activity against TIFA activation and the resultant NF-κB activation may be used for inhibiting TIFA activation and resultant NF-κB activation in a subject in need of such treatment, thereby benefiting treatment of a disease or disorder associated with abnormal TIFA activation and/or NF-κB activation.

According to the present invention, a TIFA peptide fragment must include a dimerization-core peptide segment (F2 domain), which can either be connected with a Thr9 peptide segment (F1 domain) at the N-terminal or a TRAF6/TRAF2 interacting peptide segment (F3 domain) at the C-terminal. In one embodiment, a TIFA peptide fragment of the present invention includes a F1/F2 fragment where a Thr9 peptide segment (F1 domain) is connected with a dimerization-core peptide segment (F2 domain), from N-terminal to C-terminal, lacking a TRAF6/TRAF2 interacting peptide segment (F3 domain). In another embodiment, a TIFA peptide fragment of the present invention includes a F2/F3 fragment where a dimerization-core peptide segment (F2 domain) is connected with a TRAF6/TRAF2 interacting peptide segment (F3 domain), from N-terminal to C-terminal, lacking a Thr9 peptide segment (F1 domain). It is firstly demonstrated in the present invention that such TIFA peptide fragment can acts as a dominant negative inhibitor of TIFA, which is effective in interfering with self-association of endogenous TIFA so that TIFA activation and the resultant NF-κB activation, particularly cytokine-induced NF-κB activation, can be attenuated and a disease or disorder associated with abnormal TIFA activation and/or NF-κB activation can thus be treated.

To practice the method disclosed herein, an effective amount of a composition such as a pharmaceutical composition described herein, comprising a TIFA fragment or a nucleic acid encoding the same, can be administered to a subject (e.g., a human) in need of the treatment via a suitable route. The term "effective amount" used herein refers to the amount of an active ingredient to confer a desired biological effect in a treated subject or cell. The effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder, such as cancer or inflammatory diseases. A subject suspected of having any of such target disease/disorder might show one or more symptoms of the disease/disorder. A subject at risk for the disease/disorder can be a subject having one or more of the risk factors for that disease/disorder.

Abnormal TIFA activation is associated with various diseases and disorders. In some particular embodiments, the disease or condition associated with TIFA activation is an inflammatory disorder due to TIFA activation e.g. cytokine-stimulated NF-κB activation. Examples of such diseases or disorders include, but are not limited to, hepatitis, atherosclerosis pulmonary arterial hypertension, cardiomyopathy, rheumatoid arthritis, inflammatory bowel disease and Fabry disease. In other embodiments, the disease or condition associated with TIFA activation is cancer, particularly cancer associated with chronic inflammation or inflammatory condition. One example of cancer to be treated in the present invention is a hematologic cancer, selected from the group consisting of a lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, and mast cell leukemia), myeloid neoplasms, and mast cell neoplasms. Other example of cancer to be treated in the present invention is a cancer associated with chronic inflammation or inflammatory condition, including colorectal, lung, gastric intestinal, prostate, pancreas, lymphoma, ovarian, and breast cancer.

In one certain embodiment, the individual or subject can be a mammal afflicted with or at risk of leukemia.

The term "treating" as used herein refers to the application or administration of a composition including one or more active agents to a subject afflicted with a disorder (e.g. diabetes, atherosclerosis and other inflammatory diseases), a symptom or conditions of the disorder, or a progression or predisposition of the disorder, with the purpose to cure, heal, alleviate, relieve, alter, remedy, ameliorate, improve, or affect the disorder, the symptoms or conditions of the disorder, the disabilities induced by the disorder, or the progression or predisposition of the disorder. Therefore, the term "treating" can also include, depending on the condition of the subject to be treated, preventing the disorder, including preventing onset of the disorder or of any symptoms associated therewith as well as reducing or alleviating the severity of the disorder or any of its symptoms prior to onset.

As used herein, the term "anti-cancer treatment" can refer to administration of an anti-cancer agent or irradiation to a subject having a tumor or cancer, providing the effect of inhibiting the growth or proliferation, or inducing the killing, of a tumor or cancer cell, for example. As used herein, the term "anti-cancer agent" can include a chemotherapeutic agent or a molecularly targeted agent. The term "chemoresistant" can mean that a tumor or cancer cell that shows little or no significant detectable therapeutic response to a chemotherapeutic agent used in chemotherapy. Some chemotherapeutic agent induces chemoresistant which may result in the survival of a population of tumor cells that subsequently leads to recurrence following treatment. A "standard dose" as used herein can refer to an effective dose of a therapeutic agent that is recommended by authoritative sources in the pharmaceutical community including the Food and Drug Administration and often used in routine practice. A "reduced dose" as used herein can refer to a dose that is lower than a standard dose but still retains substantially the same therapeutic effects of the same therapeutic agent. Specifically, according to the invention, a reduced dose of a chemotherapeutic agent is about 90% or less, 80% or less, 70% or less, 60% or less, 50% or less, of standard therapeutic dose of the same agent.

Some cancer patients may have a poor response to an anti-cancer agent and may need a high dose to achieve the required therapeutic effect. It is surprisingly found in the present invention that inhibition of TIFA activation can enhance chemotoxicity/lower chemoresistance of an anti-cancer agent, which lead to a promoted therapeutic efficacy. Specifically, when TIFA activation is inhibited (e.g. by using TIFA fragments as TIFA dominant negative inhibitors) in cancer cells, the dose of an anti-cancer agent required to inhibit the cell proliferation of the cancer cells is reduced as compared to that when TIFA activation is not inhibited; and a combination of an anti-cancer agent with an TIFA antagonist (e.g. TIFA fragments as used herein) provides a synergistically enhanced anti-cancer effect e.g. in reduction of tumor volume, as compared to treatment with the anti-cancer drug alone.

As used herein, the term "TIFA antagonist" refers to a substance or an agent which can substantially reduce, inhibit, block and/or mitigate activation of TIFA, including but not limited to, phosphorylation and oligomerization and the subsequent NF-κB activation particularly caused by stimulation of inflammatory cytokine or pathological stresses. In addition to TIFA fragments as TIFA dominant negative inhibitors as above described, TIFA antagonists may include an anti-sense nucleic acid molecule directed to a TIFA gene or a small interfering RNA (siRNA) directed toward a TIFA nucleic acid, which can be used in the present invention.

In some embodiments, the TIFA antagonist comprises at least one antisense nucleic acid molecule capable of blocking or decreasing the expression of a functional TIFA. Nucleotide sequences of TIFA are known and are readily available from publicly available databases. It is routine to prepare antisense oligonucleotide molecules that will specifically bind a target mRNA without cross-reacting with other polynucleotides. Exemplary sites of targeting include, but are not limited to, the initiation codon, the 5' regulatory regions, the coding sequence and the 3' untranslated region. In one certain embodiment, the exemplary site of targeting is in the coding sequence of TIFA. In some embodiments, the oligonucleotides are about 10 to 100 nucleotides in length, about 15 to 50 nucleotides in length, about 18 to 25 nucleotides in length, or more. The oligonucleotides can comprise backbone modifications such as, for example, phosphorothioate linkages, and 2'-0 sugar modifications well known in the art.

4. TIFA as a Marker of Poor Prognosis of AML

The present invention is also based on identification of TIFA as a marker of poor prognosis of AML. As demonstrated in the examples below, AML patients with higher TIFA protein level seemed to have higher white blood cell (WBC) and blast counts than those with lower TIFA level. In addition, higher TIFA expression in AML patients is associated with an inferior response rate and after following-up, patients with higher TIFA expression exhibits significantly shorter overall survival (OS) and disease-free survival (DFS) than those with lower TIFA expression.

Therefore, the present invention provides a method for predicting prognosis of leukemia based on the TIFA's protein level. In particular, the method of the present invention comprises measuring an expression level of TIFA in a sample obtained from a leukemia patient and determining the prognosis of leukemia in the patient based on the expression level of TIFA in the sample, wherein an elevated level of TIFA in the sample indicates poor prognosis.

As used herein, an elevated level means a level that is increased compared with the level in a subject free from the cancer or inflammatory disorder in question or a reference or control level. For example, an elevated level can be higher than a reference or control level by more than 10%, 20%, 30%, 40%, 50%, 60%, 70%, 80%, 90% or 100%. A reference or control level can refer to the level measured in normal individuals or sample types such as tissues or cells that are not diseased.

As used herein, a biological sample to be analyzed by any of the methods described herein can be of any type of samples obtained from a subject to be diagnosed, preferably a blood sample. Typically, a blood sample can be whole blood or a faction thereof e.g. peripheral mononuclear cells, or plasma, heparinized or EDTA treated to avoid blood clotting (serum). Alternatively, the biological sample can be a tissue sample or a biopsy sample.

In particular, the method of the present invention for predicting prognosis of a leukemia patient comprises
   (a) measuring a level of TIFA in a first biological sample obtained from the patient at a first time-point;
   (b) measuring a level of TIFA in a second biological sample obtained from the patient at a second time-point; and
   (c) determining leukemia progression in the patient based on the levels in the first and second biological samples wherein an elevated level of TIFA in the second biological sample as compared to that in the first biological sample is indicative of leukemia progression.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLES 1.1 Cell Culture, Isolation of Human Peripheral Blood Mononuclear Cells (PBMCs), and TNF-α Stimulation Hela, 293T, and HL-60 cell lines were obtained from Dr. Li-Jung Juan of Academia Sinica (Taipei, Taiwan, 2014), KG-1 cell line was obtained from Prof. Shih-Lan Hsu of Taichung Veterans General Hospital (Taichung, Taiwan, 2015), and the rest of cell lines were obtained from Dr. Shui-Tein Chen of Academia Sinica (Taipei, Taiwan, 2015). All cell lines were expanded and stored in liquid nitrogen when received. Original vials were thawed for these experiments and authenticated simultaneously by STR DNA fingerprinting using the Promega GenePrint® 10 System and analyzed by ABI PRISM 3730 GENETIC ANALYZER and GeneMapper® software. All resulting SI R profiles were matched with known ATCC fingerprints (ATCC.org). Maintenance of respective cell lines followed our previous protocols (20,27,28). 293T and HeLa cells were maintained in Dulbecco's modified Eagle's medium (DMEM, Gibco). Primary PBMCs, HL-60, KG-1, THP-1, U937, Jurkat, and K562 cells were maintained in Roswell Park Memorial Institute medium (RPMI-1640, Invitrogen). All media were supplemented with 10% decomplemented fetal bovine serum (FBS, Gibco), 200 mM L-glutamine (Gibco), 100 U/mL penicillin (Gibco) and 100 μg/mL streptomycin (Gibco). All cells were incubated in a humidified atmosphere at 37° C. with 5% $CO_2$. To isolate human PBMCs, freshly acquired whole bloods were layered over Ficoll (GE healthcare) as previously described (28). Isolated primary cells were maintained according to a previously described protocol (29) and subjected to experimental analyses within two weeks. When necessary, cells were starved in serum-free condition for 8 h prior to addition of 10 ng/mL of TNF-α (R&D Systems) for 30 min or at indicated time points.

1.2 Plasmids and Synthesis of siRNA

The pCDNA3.1 vector was used to carry full-length TIFA wild-type following a synthesized HA-tag, and full-length Aurora A was constructed in the same vector except that the Flag-tag was used. For retroviral transduction, full-length (wild-type or T9A mutant with TIFA siRNA-resistant silent mutation) and fragments of TIFA were amplified by polymerase chain reaction (PCR) and carried by the pLNCX vector (Clontech) followed by two consecutive Myc-tags as previously described (27). The pNF-κB-Luc plasmid was a gift of Dr. L.-P. Ting (National Yang-Ming University, Taiwan). All constructs were confirmed by sequencing prior to experimental applications. Double-stranded siRNA oligomer corresponding to sequence 5'-UCA GGA CAA ACA GGU UUC CCG AGU U-3' (SEQ ID NO: 95) for targeting TIFA (20) was synthesized by GeneScript, Aurora A targeting siRNA was from Cell Signaling (#8883), and scramble control oligomers from GeneScript.

1.3 Reverse Transcription Quantitative PCR (RT-qPCR)

Transcriptional levels of specific genes were examined by the real-time quantitative PCR as previously described with minor modifications (27). At day 3 post-transfection of siRNAs, total RNAs were extracted from harvested cells with TRIzol reagent following the manufacturer's instruction (Invitrogen), and first strand cDNAs were synthesized from DNase I (Invitrogen) treated total RNAs in the presence of oligo-dT (Invitrogen) using SuperScript® III kit (Invitrogen) according to the manufacturer's protocol. RT-qPCR was conducted using gene specific primers supplemented with SYBR Green (Roche) and analyzed by Light-Cycler® 480 (Roche).

1.4 Transient Transfection of Plasmid and siRNA

For transient transfection of 293T cells, $6 \times 10^5$ cells were transfected with 2 μg of indicated plasmid DNA using Jet-PEI (Polyplus Transfection) for 48 h (pCDNA3.1 vector, HA-tagged TIFA, and pNF-κB-Luc) or 24 h (Flag-tagged Aurora A) according to the manufacturer's instruction. For transient transfection of U937 cells, $10^6$ suspension cells were transfected with 3 μg of the pNF-κB-Luc plasmid DNA using Lipofectamine 2000 (Invitrogen) for 48 h according to the manufacturer's instruction. To silence specific genes, $6 \times 10^5$ 293T cells or $10^6$ suspension cells were transfected with 30 pmol (293T cells) or 50 pmol (suspension cells) of indicated siRNA supplemented with 9 or 15 μL of Lipofectamine RNAiMAX (Invitrogen) in the presence of Opti-MEM (Invitrogen) according to the manufacturer's instruction. Six hours after primary transfection, cells were incubated with the regular medium for 24 h, and the secondary siRNA transfection was performed with the same protocol. Cells or conditional media were collected after 72 h of incubation.

1.5 Preparation of Retrovirus Based Stable Lines

To perform retroviral transduction, pseudotyped viruses were packaged by the pantropic retroviral expression system in the presence of VSV-G according to the manufacturer's instruction (Clontech) and subjected to infection of indicated cells as previously described (27). After 400 μg/mL G418 selection for weeks, the expressions of ectopic proteins in stable cells were confirmed by western blot analysis before experimental analysis or siRNA transfection for phenotypic rescue experiments.

1.6 Treatments of Cells

All chemotherapy drugs used in this study were obtained as follows: etoposide (VP-16) was from Sigma; idarubicin and cytarabine (Ara-C) were from Phizer; cisplatin was from The European Directorate for the Quality of Medicines & HealthCare (EDQM); sorafenib (Raft) was from Santa Cruz Biotechnology; etanercept (Enbrel, TNF-α inhibitor) was from Wyeth, bortezomib (Velcade, NF-κB inhibitor) was from Janssen Pharmaceutica; ABT-263 (Navitoclax, BCL-2 inhibitor) was from AdooQ Bioscience. For cell treatment with X-ray irradiation, irradiation was carried out in a Faxitron RX-650 irradiator (Faxitron X-ray Corporation) at a dose rate of 0.46 Gy/min. When necessary, cells were starved in serum-free condition for 8 h prior to the addition of 10 ng/mL of TNF-α (R&D Systems) for 30 min or at indicated time points.

The kinase inhibitors and conditions used in the treatment of 293T cells were as follows: 100 nM Casein Kinase II Inhibitor III TBCA (CK2i), 500 nM 4-amino-5-(bromomethyl)-2-methylpyrimidine dihydrobromide (GRKi), and 25 nM sorafenib (Raft) were from Santa Cruz Biotechnology; 200 nM necrostatin-1 (RIPK1i) and 10 nM GÖ 6976 (PKCi) were from Tocris Bioscience; 50 nM Akt inhibitor VI (Akti), 300 nM 1RAK-¼ inhibitor (IRAK¼i), and 10 nM (5Z)-7-oxozeaenol (TAK1i) were from Merck Millipore; 500 nM caffeic acid phenethyl ester (CAPE, NF-κBi) was from Sigma; 10 nM VX680 (Aurora Ai) was from Selleck Chemicals; 50 nM MK-5108 (Aurora Ai) was from AdooQ Bioscience.

1.7 Antibodies

TIFA-specific monoclonal antibody was raised as previously described (20). Anti-Aurora A, anti-phospho-Aurora A (Thr288), anti-Bcl-2, and anti-Bcl-$X_L$ were from Cell Signaling. Anti-His-tag was from SignalChem. Anti-Myc, anti-Flag, and anti-HA were from Sigma. Anti-IκK alpha (phospho T23), anti-IκB alpha (phospho S32+S36), anti-human CD45 PerCP/Cy5.5, anti-human CD33 FITC, anti-β-actin, and anti-Bax were from Abcam. Anti-NF-κB active p65 subunit (clone 12H11) and horseradish peroxidase (HRP)-conjugated anti-mouse or anti-rabbit IgG were from Millipore.

1.8 In Vitro Kinase Assay

Experiments followed protocols we previously established (20). 293T cells under indicated treatment were lysed with CHAPS lysis buffer (20 mM PIPES, 1 mM $Na_3VO_4$, 1 mM EGTA, 50 mM Tris-HCl, 150 mM NaCl, 50 mM NaF, 1% CHAPS, and 10% glycerol) supplemented with protease inhibitor cocktail (Roche) and phosphatase inhibitor (Sigma). The cell extracts were incubated with the recombinant His-tagged wild-type or T9A mutant TIFA in the reaction buffer (40 mM HEPES pH 7.5, 20 mM $MgCl_2$, and 100 μM ATP) in the presence of 1 mCi/mL [γ-$^{32}$P]ATP (Perkin-Elmer) at 37° C. for 30-90 min. His-tagged proteins were then pulled down with M-280 Dynabeads coated with anti-His mAb. The reaction was terminated by addition of SDS sample buffer and heating at 95° C. for 10 min prior to SDS-PAGE. The level of phosphorylation on recombinant proteins was revealed through autoradiography.

1.9 Immunoprecipitation

Immunoprecipitation experiment was conducted as previously described (28). Sub-confluent 293T cells in a p100 petri dish were transfected with 5 μg of the vectors or HA-TIFA using Jet-PEI (Polyplus Transfection). After 48 h, cells were treated with or without 10 ng/mL TNF-α (R&D Systems) for 30 min, washed by PBS, and lysed with CHAPS lysis buffer (20 mM PIPES, 1 mM $Na_3VO_4$, 1 mM EGTA, 50 mM Tris-HCl, 150 mM NaCl, 50 mM NaF, 1% CHAPS, and 10% glycerol) supplemented with protease inhibitor cocktail (Roche), phosphatase inhibitor cocktail 3 (Sigma). Three μg of indicated antibody was pre-coated with 100 μL M-280 Dynabeads (Invitrogen) overnight at 4° C. The 500 μg cell extracts were incubated with 15 μL antibody-coated Dynabeads at 4° C. overnight. The protein-bead complex was then washed with Tris-buffered saline Tween 20 (TBST) buffer and subjected to Western blot analysis.

1.10 Western Blot

To obtain whole cell extracts, 6×10$^5$ 293T cells or 10$^6$ suspension cells were washed with ice-cold PBS, lysed in RIPA lysis buffer (50 mM Tris pH 7.4, 150 mM NaCl, 1% NP-40, 0.5% sodium deoxycholate, and 0.1% SDS) supplemented with protease inhibitor cocktail (Roche) and phosphatase inhibitor cocktail (Sigma). After 5 repeated freeze-thaw cycles, cell extracts were cleared by centrifugation at 4° C. Cell extracts were quantified using Bradford assay, and equal amounts of soluble proteins were mixed with SDS sample buffer, boiled, separated by SDS-PAGE, and blotted onto PVDF membranes (Millipore). Membranes were then blocked for 1 h with 5% dry milk in PBST (PBS supplemented with 0.1% Tween-20) buffer and incubated for overnight at 4° C. with primary antibody diluted in PBST containing 1% bovine serum albumin (Sigma). After three washes with PBST, membranes were incubated with HRP-conjugated anti-mouse or anti-rabbit IgG. Membranes were washed five times with PBST and the blotted protein bands were revealed by the ECL system (Millipore). All western blot analyses were performed independently at least three times except that of primary PBMCs.

1.11 Luciferase Reporter Assay

Luciferase-based NF-κB reporter assay was conducted as previously described (20). A total of 6×10$^5$ 293T or 10$^6$ suspension U937 Cells in one well of 6-well plates with indicated conditions were transiently transfected with 2 μg of pNF-κB-Luc reporter plasmid for 48 h before harvest. Cells were treated with 10 ng/mL TNF-α (R&D Systems) for 30 min and lysed with 1× passive lysis buffer (Promega). 100 μg of cell lysates was dispensed into a well of 96-well plate, followed by addition of 100 μL of luciferase assay buffer LARII (Promega) and 100 μL of Stop & Glo reagent (Promega). The triplicated chemiluminescence were measured by SpectraMax Paradigm Multi-Mode Plate Reader (Molecular Devices) and normalized to corresponding β-actin level from a parallel western blot analysis of cell lysates. Results were represented as relative luminescence units (RLU) from three independent experiments.

1.12 WST-1 Cell Viability Assay

A total of 10$^5$ suspension cells under indicated condition were seeded per well in 96-well plates and cell viability was analyzed at the indicated time point post treatment. The WST-1 reagent (Roche) was mixed with cells in 10-fold dilution according to the manufacturer's instructions, and absorbances of triplicated results were read by SpectraMax Paradigm Plate Reader (Molecular Devices) and normalized to day zero or mock control.

1.13 Patient Samples

Sixteen patients who were diagnosed as de novo AML at the Taichung Veterans General Hospital, Taiwan (VGHTC; AML#1-9) and National Taiwan University Hospital (NTUH; AML#10-16) from December 2007 to March 2014 were enrolled for the analyses of western blot, WST-1 cell viability, and apoptosis assay. The average of blasts in these patients were more than 60%±18 with 4 exceptions (patient #2, 9, 12, and 16) whose blood samples were taken after chemotherapy to suppress acute condition. For analysis of immunocytochemical staining, 85 adult AML patients who received standard chemotherapy and had available cryopreserved BM cells at the NTUH from March 2009 to January 2012 were enrolled (30,31). Written informed consent was obtained from all participants in accordance with the Declaration of Helsinki, and all experimental studies followed the institutional protocols (CE11166-2, VGHTC, No. 201408027RIND, NTUH, and AS-IRB02-103189 and AS-IRB02-104147, Academia Sinica, Taiwan).

1.14 Immunocytochemical Staining

Immunocytochemical staining was performed as previously described with minor modifications (32). Cytospin smears of BM leukemia cells from 85 patients were fixed for 3 min in formalin acetone (3%). The specimen was then incubated with peroxidase blocking enzyme (10 min), followed by TIFA monoclonal antibody (1:200 in blocking solution, overnight at 4° C.) (20). Biotinylated donkey anti-mouse IgG (1 µg/mL, diluted in blocking solution, 30 min; DAKO) was used as secondary antibody and the protein was detected using the streptavidin-peroxidase complex (DAKO). The specimens were counter-stained with hematoxylin. A score of 0 to 4 was calculated for each specimen, according to the addition of the score of staining intensity (0=none, 1=weak, 2=strong) and the score of percentage of myeloid cells positively stained (0=0-25%, 1=26-50%, 2=51-00%).

1.15 Analyses of Apoptosis and Flow Cytometry

At the $2^{nd}$ day post-transfection of siRNAs, $10^6$ PBMCs were seeded per well in 6-well plates and then treated with different chemotherapy drugs. After 48 h, cells were washed with ice-cold PBS and subjected to apoptosis detection using FITC annexin V apoptosis detection kit according to the manufacturer's instruction (BD Biosciences). Cells were then gated for myeloid lineage by light-scattering following a previously described protocol (33), and apoptosis rate, as suggested by double staining of propidium iodide and FITC annexin V, was analyzed by BD FACSCalibur Flow Cytometer (BD FACSCalibur) as previously described (27). For analysis of U937 cells in the xenograft model, BM cells or mouse PBMCs were sequentially stained with anti-human CD33 FITC and CD45 PerCP/Cy5.5 respectively for 1 h on ice. Cells were washed with ice-cold PBS and subjected to flow cytometry as abovementioned.

1.16 Assessment of Cytokine and Chemokine Secretion (Cytokine Array and ELISA)

Condition media from equal numbers of cultured U937 cells were collected at 72 h post indicated treatments and assessed by the Human Cytokine Array C1 according to the manufacturer's instruction (AAH-CYT-1, RayBiotech). Data were acquired using the ImageJ software and normalized to the positive controls. When indicated, the amounts of secreted cytokines and chemokines in the conditional mediums were determined by the enzyme-linked immunosorbent assay (ELISA) test kit following the manufacturer's instructions (R&D Systems). The absorbances of triplicated samples were read by SpectraMax Paradigm Plate Reader (Molecular Devices). All raw data were normalized to PBS control, and results were represented as relative secretion of cytokines from three independent experiments.

1.17 Xenotransplantation of Human Leukemic Cells and In Vivo Chemo Drug Treatment Six to eight week-old athymic nude mice from the National Laboratory Animal Center (Taiwan) were housed in the pathogen-free facility of Chang Gung Memorial Hospital (Protocol No. 2014092305). For the myeloid sarcoma model, mice were inoculated subcutaneously with $5 \times 10^6$ U937 stable cells in 50% matrigel (Corning) per animal, followed by intraperitoneal administration of PBS or cytarabine (Ara-C, 50 mg/kg) at day 6, 8, 11 post inoculation. Tumor sizes were documented twice per week by the formula, width$^2$×length×0.52 (34). For the orthotopic leukemic model, mice were injected with $1.5 \times 10^5$ U937 stable cells per animal via inferior vena cava (IVC) through surgical operation, followed by five daily administrations of the same treatment at the $5^{th}$ day post transplantation. Mice were humanely killed at the $60^{th}$ day, and BM cells in femurs were subjected to flow cytometry.

1.18 Statistical Analysis

All data are represented by the means±standard deviation from three independent experiments. Statistical significance determined by the independent samples t-test were represented as *P<0.05, P<0.01, and *P<0.001 except otherwise specified. For immunocytochemical staining, correlations between variables were assessed by the Spearman rank correlation. Mann-Whitney U test was used to analyze the difference in the expression of TIFA in AML patients. Overall survival (OS) was measured from the date of first diagnosis to death from any cause, and disease-free survival (DFS) was calculated from the time of complete remission (CR) until relapse, death from any cause, or end of study. Kaplan-Meier estimation was used to plot survival curves, and log-rank tests were used to test the difference between groups. Hazard ratio and 95% confidence interval (CI) was estimated by Cox proportional hazards regression models to determine independent risk factors associated with OS and DFS in multivariate analyses. Two-sided P values <0.05 were considered statistically significant.

2. Results 2.1 TIFA is Involved in Aurora A Kinase-Dependent NF-κB Signaling

Figure 1A:
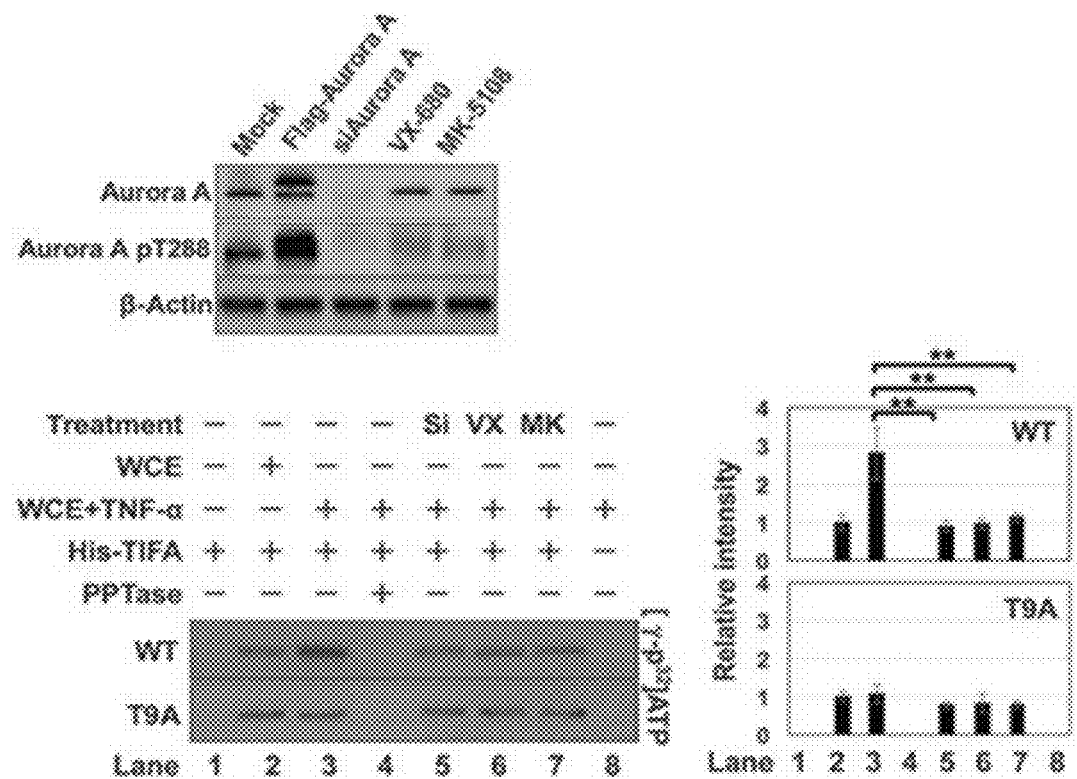
FIGS. 1A, 1B, 1C and 1D include charts showing that TIFA is required for Aurora A-dependent NF-κB signaling.
Figure 1B:
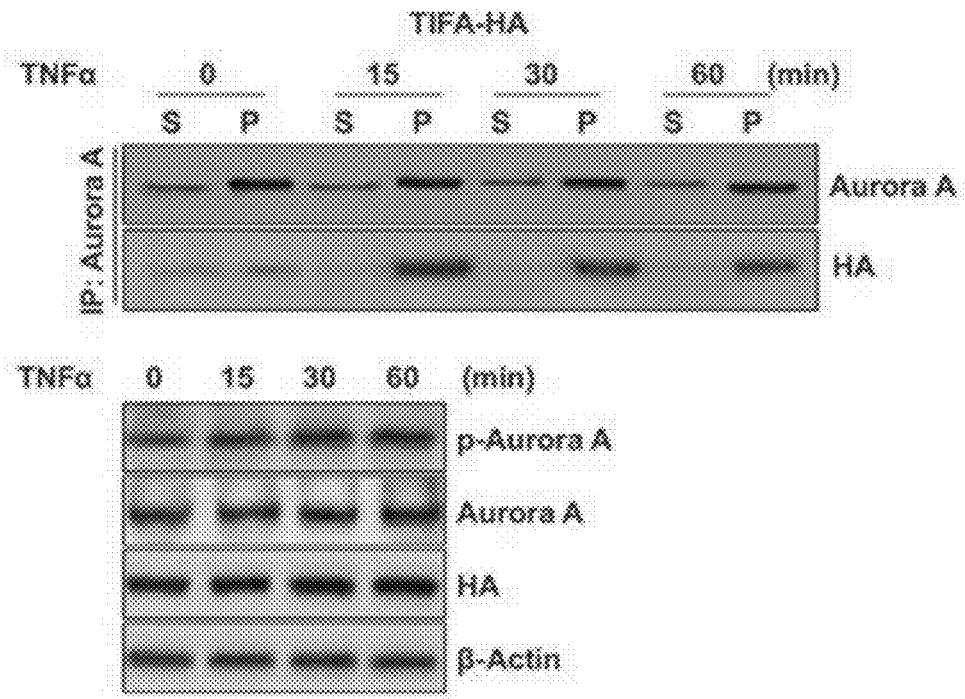

We previously suggested that phosphorylation of TIFA at threonine 9 could involve Ser/Thr kinases in the PI3K/AKT signaling pathway (20). To pinpoint the most direct kinase responsible for Thr9 phosphorylation of TIFA, we screened kinase inhibitors through a protocol we established previously (20,23), and found that the Aurora A inhibitor was most effective against in vitro phosphorylation by TNF-α treated 293T cell lysates. We further validated that Aurora A is required for the Thr9 phosphorylation of TIFA based on three experiments: First, lysates of cells treated with Aurora A-specific siRNA and two different Aurora A inhibitors all showed attenuated abilities in TIFA Thr9 phosphorylation, similar to the result of the unphosphorylatable T9A mutant (FIG. 1A, lanes 5-7). Second, immunofluorescence staining showed colocalization of endogenous TIFA speckles (20) and activated Aurora A (phospho-Thr288) upon TNF-α treatment (data not shown). Third, immunoprecipitation experiments revealed direct interaction between Aurora A and TIFA, which was reinforced upon TNF-α stimulation (FIG. 1B).

Figure 1C:
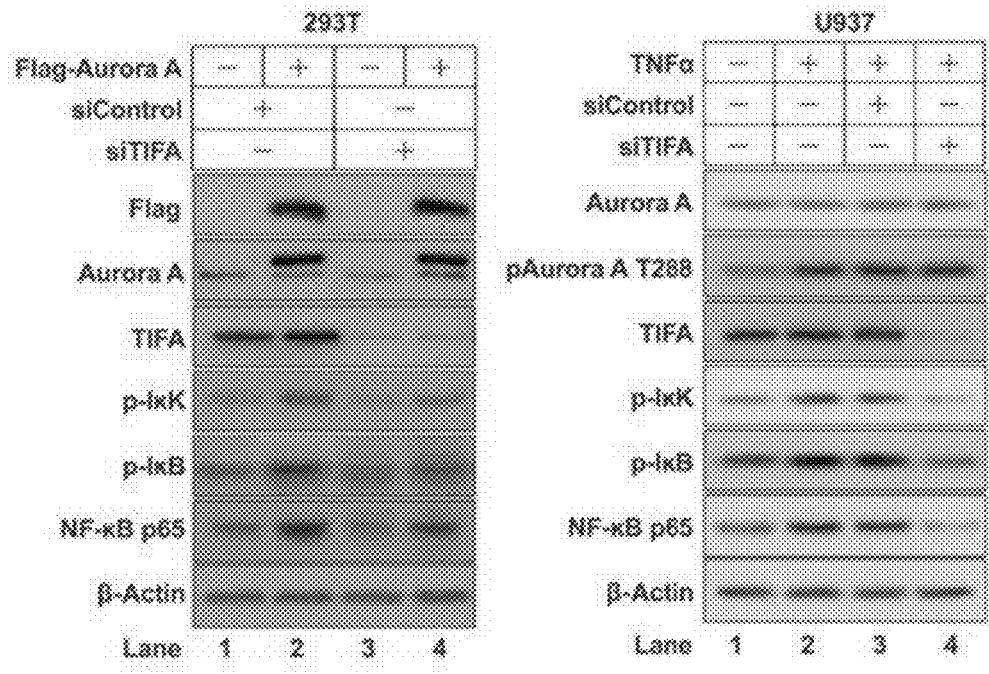
Figure 1D:
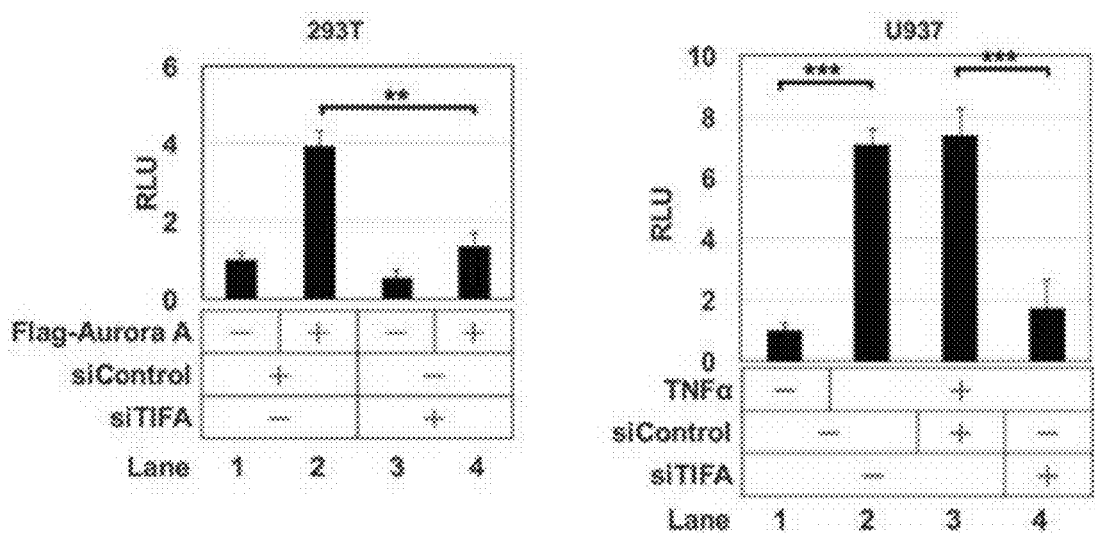

It has been reported that Aurora A regulates NF-κB signaling (17), and elevated expression of Aurora A coincides with promoted levels of TNF-α, NF-κB, and chronic inflammation in gastric neoplasia (35). We also observed a marked elevation in the levels of activated NF-κB, phosphorylated IκK and IκB, and NF-κB-driven luciferase activity in response to overexpression of Aurora A or TNF-α treatment (FIG. 1C-D, lane 2), and in addition showed that such elevation was negated upon silencing of TIFA (lane 4). The results collectively suggest that the proposed role of Aurora A in the regulation of NF-κB signaling requires TIFA.

Figure 2:
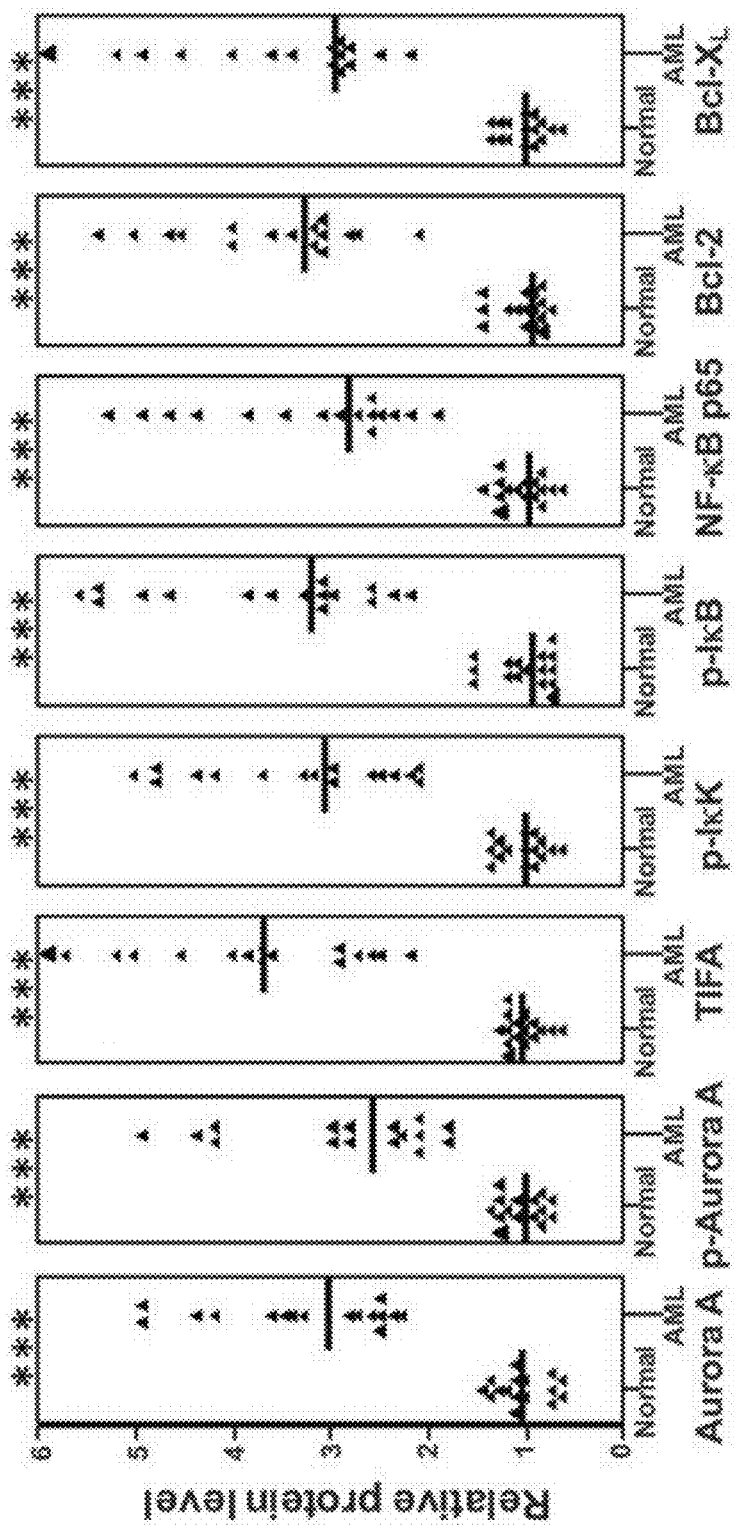
FIG. 2 shows that overexpression of the TIFA protein is associated with pro-survival factors and poor prognosis in AML patients. Representative protein expressions of TIFA and pro-survival factors in normal and AML PBMCs (n=16 in each group). Results of western blot analyses (FIG. 4C) were quantified and normalized to corresponding β-actin levels, and relative intensities of each signal factors normalized to medium value in the normal counterparts were plotted. Horizontal bars, medium value.

2.2 TIFA is Correlated with Aurora A, Pro-Survival Factors, and Poor Prognosis of AML Aurora A was found to be highly expressed in AML (18). Since we have shown that TIFA is required for the activation of NF-κB in AML lines U937 and THP-1 (FIG. 1C-D), we further asked whether the TIFA protein level is associated with Aurora A and NF-κB signal factors during leukemogenesis. Because of the cytogenetic clonal heterogeneity in AML (36) and limited volumes of patient blood samples, we chose to perform western blot analysis with a TIFA-specific monoclonal antibody (20) to compare freshly isolated PBMCs from 16 de novo AML patients and 16 normal individuals. We found that the TIFA protein level is significantly elevated in all of the AML-derived PBMCs but remains unchanged in those of normal donors. In addition, the elevation of TIFA is concomitant with upregulation of the levels of Aurora A protein, activated Aurora A, phosphorylated IκK/IκB, activated NF-κB, and pro-survival factors Bcl2/Bcl-X$_L$ (FIG. 2A). In support, pairwise comparisons among the levels of all tested proteins in all PBMCs reveal strong correlations, suggesting that these factors are functionally related in AML (Pearson's correlation coefficient=0.862-0.991).

The prognostic implication of the TIFA protein level observed from non-fractionized PBMCs was further strengthened by the immunocytochemical staining of the cryopreserved BM leukemia cells derived from 85 de novo AML patients. Patients who received conventional intensive-induction chemotherapy (31) were divided into low (score 0-2, n=40) and high (score 3-4, n=45) expression groups, based on immunocytochemistry results. AML patients with higher TIFA protein level seemed to have higher WBCs and blast counts than those with lower TIFA level. In addition, higher TIFA protein expression was closely associated with the FAB M4 subtype (P=0.0315), but negatively associated with CD7 expression (P=0.0454) in leukemia cells.

Of all AML patients examined, 54 (63.5%) achieved a CR. Higher TIFA expression was associated with an inferior response rate (CR rate, 51.1% vs. 77.5%, P=0.0139). After following-up for a medium of 57.8 months (range, 0.3 to 79.1 months), patients with higher TIFA expression showed significantly shorter OS and DFS than those with lower TIFA expression. The differences remained significant in the subgroups of patients with non-M3 subtypes, intermediate-risk cytogenetics, and normal karyotype, though to a lesser extent for DFS. In multivariate analysis, higher TIFA expression was an independent factor for poor prognosis on OS irrespective of age, WBC counts at diagnosis, cytogenetics, and NPM1/FLT3-ITD (Table 2).

Figure 3A:
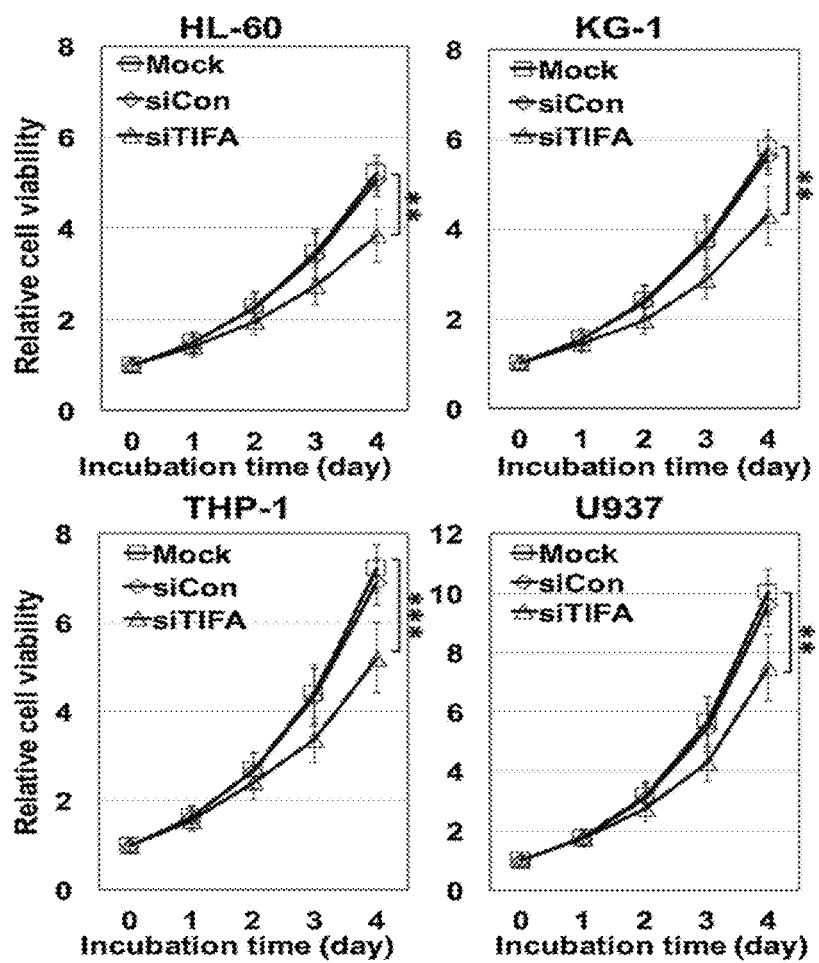
FIGS. 3A, 3B and 3C include charts showing that TIFA silencing enhances chemotoxicities to AML lines.
Figure 3B:
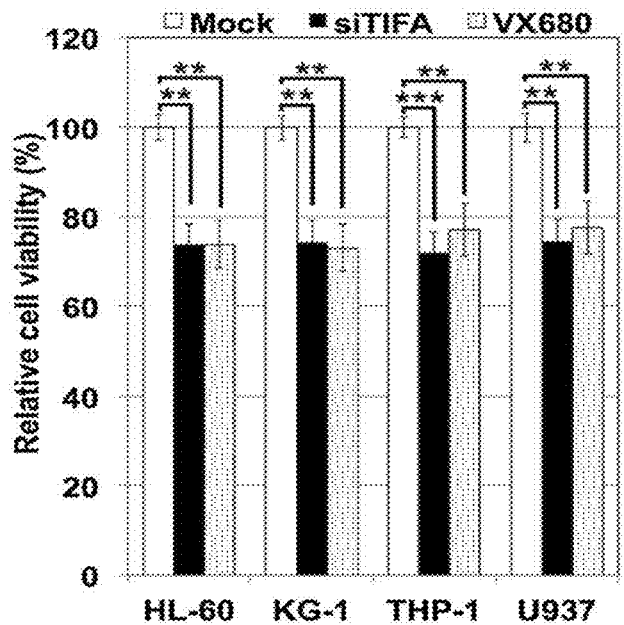

THP-1, and U937 (FIG. 3A), similar to the outcome of VX680 treatment (FIG. 3B) (18). In addition, cell proliferations of both acute lymphoblastic leukemia (ALL) line Jurkat and CML line K562 were also inhibited in response to TIFA silencing and VX680 treatment.

Figure 3C:
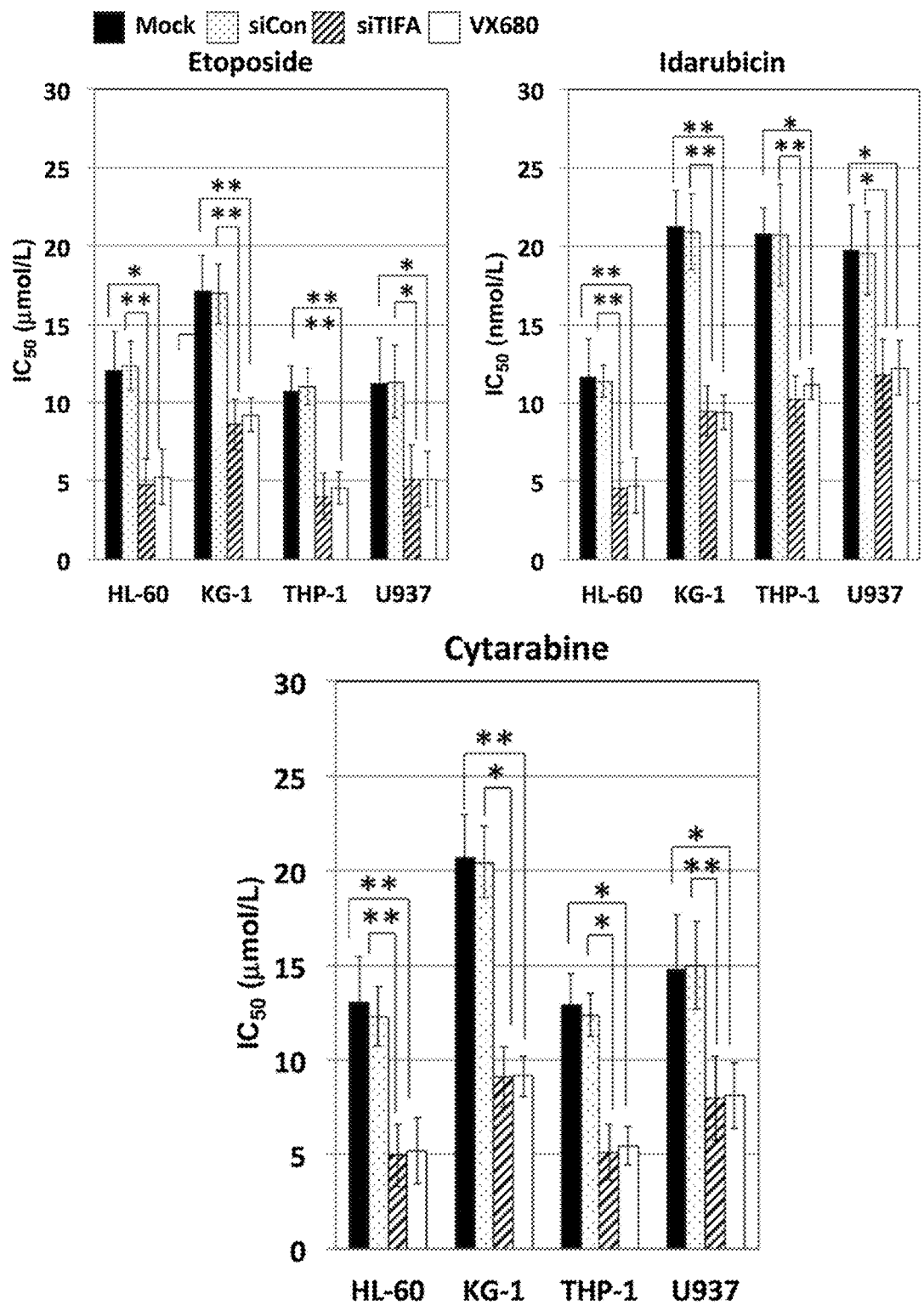

Inhibition of Aurora A kinase can promote leukemic chemosensitivity, which was considered an anticancer strategy (14,37). To test whether targeting TIFA also relieves the aggressiveness and chemoresistance of hematologic malignancy like inhibition of Aurora A, we investigated leukemic cell viability upon various treatments under TIFA silencing. The WST-1 based survival test showed that all four tested AML lines exhibit ca. 50% decrease in IC50, similar to the effect of VX680, toward chemo treatments with etoposide, idarubicin, and cytarabine, the three conventional chemotherapy drugs for AML (FIG. 3C). Similar results were also obtained from silencing of Aurora A, from treatments with atypical drugs, and from ALL and CML lines.

Figure 4A:
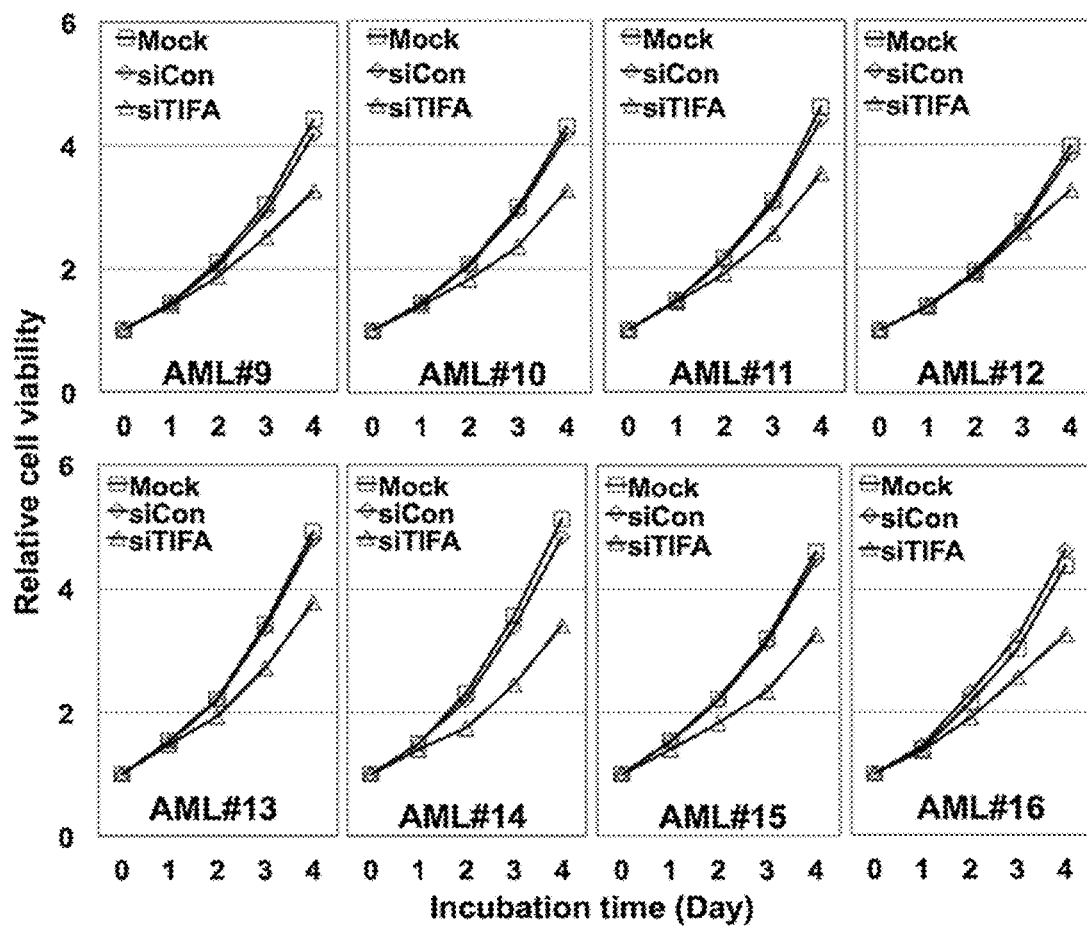
FIGS. 4A, 4b, 4C, 4D and 4E include charts showing that TIFA silencing enhances chemotoxicities to AML PBMCs.
Figure 4B:
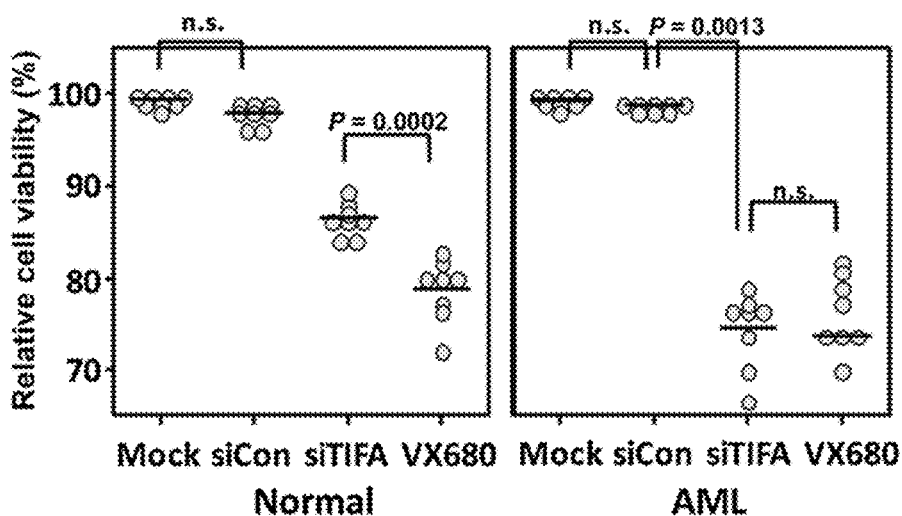
Figure 4C:
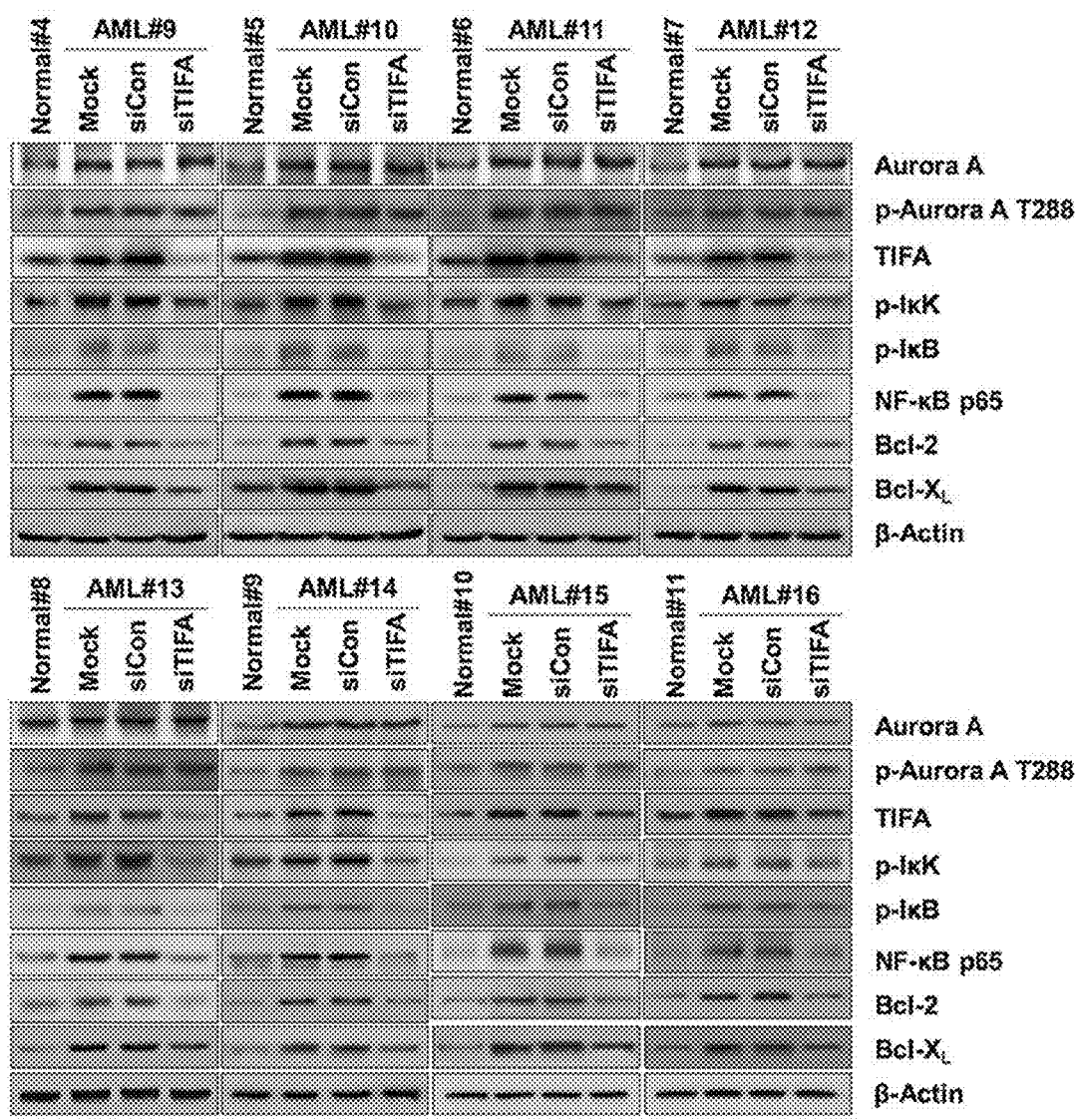
Figure 4D:
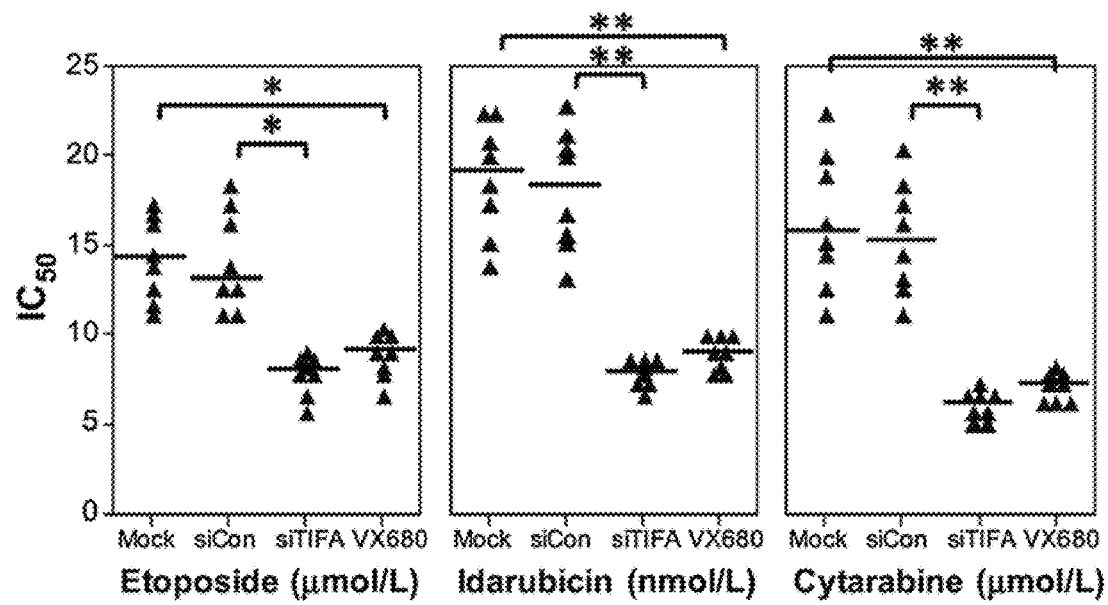

We next examined the effect of TIFA inhibition using freshly isolated AML PBMCs. In addition to growth retardation (FIG. 4A, with calculated results in the right panel of FIG. 4B), a significant retrogression of elevated NF-κB signaling factors was seen from TIFA-depleted AML PBMCs, even under overexpression and activation of Aurora A kinase (FIG. 4C). Interestingly, the effect of TIFA silencing on the viability of normal PBMCs appeared to be less than that of VX680 treatment, in contrast to the comparable chemotoxicity in the AML counterparts (comparison between right and left panels in FIG. 4B), implicating that targeting TIFA may convey less cytotoxicity toward non-leukemic cells. More importantly, silencing of TIFA consistently promoted chemosensitivities of patient-derived PBMCs similar to inhibition of Aurora A by VX680 (FIG. 4D), implicating that TIFA is required for leukemic

TABLE 2

Multivariate Analysis (Cox regression) on the OS and DFS.

| | Overall Survival | | | | Disease-free Survival | | | |
| | | 95% CI | | | | 95% CI | | |
| Variables | RR | Lower | Upper | P | RR | Lower | Upper | P |
|---|---|---|---|---|---|---|---|---|
| Age† | 3.475 | 1.326 | 9.107 | 0.011* | 2.107 | 0.914 | 4.855 | 0.080 |
| WBC§ | 2.452 | 1.116 | 5.385 | 0.026* | 1.404 | 0.661 | 2.981 | 0.377 |
| Karyotypeᴪ | 2.350 | 1.193 | 4.627 | 0.013* | 2.072 | 1.110 | 3.867 | 0.022* |
| NPM1/FLT3-ITDζ | 0.941 | 0.321 | 2.758 | 0.912 | 1.403 | 0.566 | 3.475 | 0.464 |
| Higher TIFA‡ | 2.768 | 1.200 | 6.385 | 0.017* | 1.931 | 0.905 | 4.118 | 0.089 |

Abbreviation:
RR, relative risk;
CI, confidence interval,
*Statistically significant (P < 0.05)
†Age >50 relative to Age ≤50 (the reference)
§WBC greater than 50,000/μL vs. 50,000/μL or less
ζNPM1$^{mut}$/FLT3-ITD$^{neg}$ vs. other subtypes
‡Higher TIFA vs. lower TIFA expression
ᴪunfavorable cytogenetics vs. others These results collectively suggest that TIFA expression is associated with not only Aurora A-dependent NF-κB signaling but also poor prognosis in AML.

2.3 TIFA Silencing Enhances Chemotoxicity to AML and Other Cancer Cell Lines

Figure 4E:
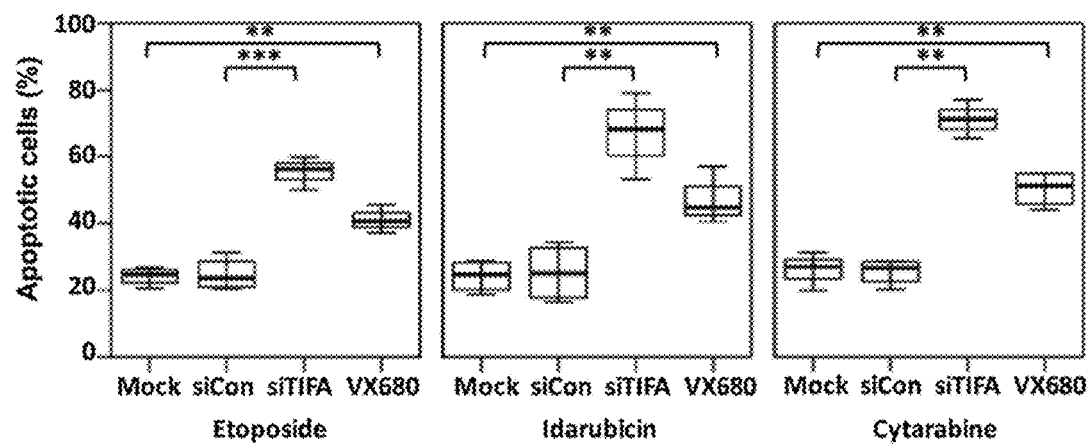

To validate the tumorigenic role of TIFA in relation to Aurora A signaling, we targeted TIFA-dependent signaling through RNA interference and examined the proliferation of AML lines through WST-1 viability assay in a time-dependent manner. The result showed that silencing of TIFA attenuates the growth of AML cell lines HL-60, KG-1, chemoresistance similar to Aurora A (38). These promoted chemosensitivities were most likely caused by enhanced apoptosis (FIG. 4E) and downregulated NF-κB signaling factors (FIG. 4C) upon silencing of TIFA. Our results together suggest that TIFA is required for the maintenance of leukemic cell growth and chemoresistance, and that TIFA can serve as a potential therapeutic target.

The effect of TIFA inhibition to promote cytotoxicity of anti-cancer treatments was also seen from other cancer lines. Various cancer lines were treated with Sorafenib, Cisplatin, Etoposide or X-ray irradiation in the presence or absence of TIFA silencing and subjected to WST-1 assay. Cytotoxicity of cells at the 4$^{th}$ day was normalized to treatment without TIFA silencing and presented. Table 3 summaries fold change of cytotoxicity by TIFA silencing under anti-cancer treatment in different cancer lines.

| Cells | Anti-cancer treatment (fold changes*) | | | |
|---|---|---|---|---|
| | Sorafenib (5 µM) | Cisplatin (5 µM) | Etoposide (10 µM) | IR (5Gy) |
| A549 (lung cancer cells) | 1.31 | 1.38 | 1.77 | 1.35 |
| H446 (lung cancer cells) | 1.17 | 1.29 | 1.27 | 1.25 |
| HeLa (cervical cancer cells) | 1.37 | 1.46 | 1.29 | 1.33 |
| HepG2 (liver cancer cells) | 1.64 | 1.59 | 1.61 | 1.71 |
| J5 (liver cancer cells) | 1.63 | 1.64 | 1.64 | 1.73 |
| Jurkat (leukaemia cells) | 1.69 | 1.73 | 1.79 | 1.73 |
| K562 (leukaemia cells) | 2.00 | 2.25 | 2.28 | 2.05 |
| THP-1 (leukaemia cells) | 1.72 | 1.61 | 1.59 | 1.58 |
| MCF-7 (breast cancer cells) | 1.47 | 1.56 | 1.30 | 1.36 |
| MDA-MB-231 (breast cancer cells) | 1.71 | 1.95 | 1.46 | 1.40 |
| NTera2 (testicular embryonic carcinoma) | 1.34 | 1.31 | 1.15 | 1.06 |
| U2OS (osteosarcoma cells) | 1.50 | 1.53 | 1.48 | 1.30 |

*Cytotoxicity of cells was calculated by (1-% survival), and fold change of cytotoxicity was determined by (cytotoxicity of TIFA silencing/cytotoxicity of non-silencing).

2.4 Targeting TIFA Through Dominant-Negative (DN) Inhibition

Figure 5A:
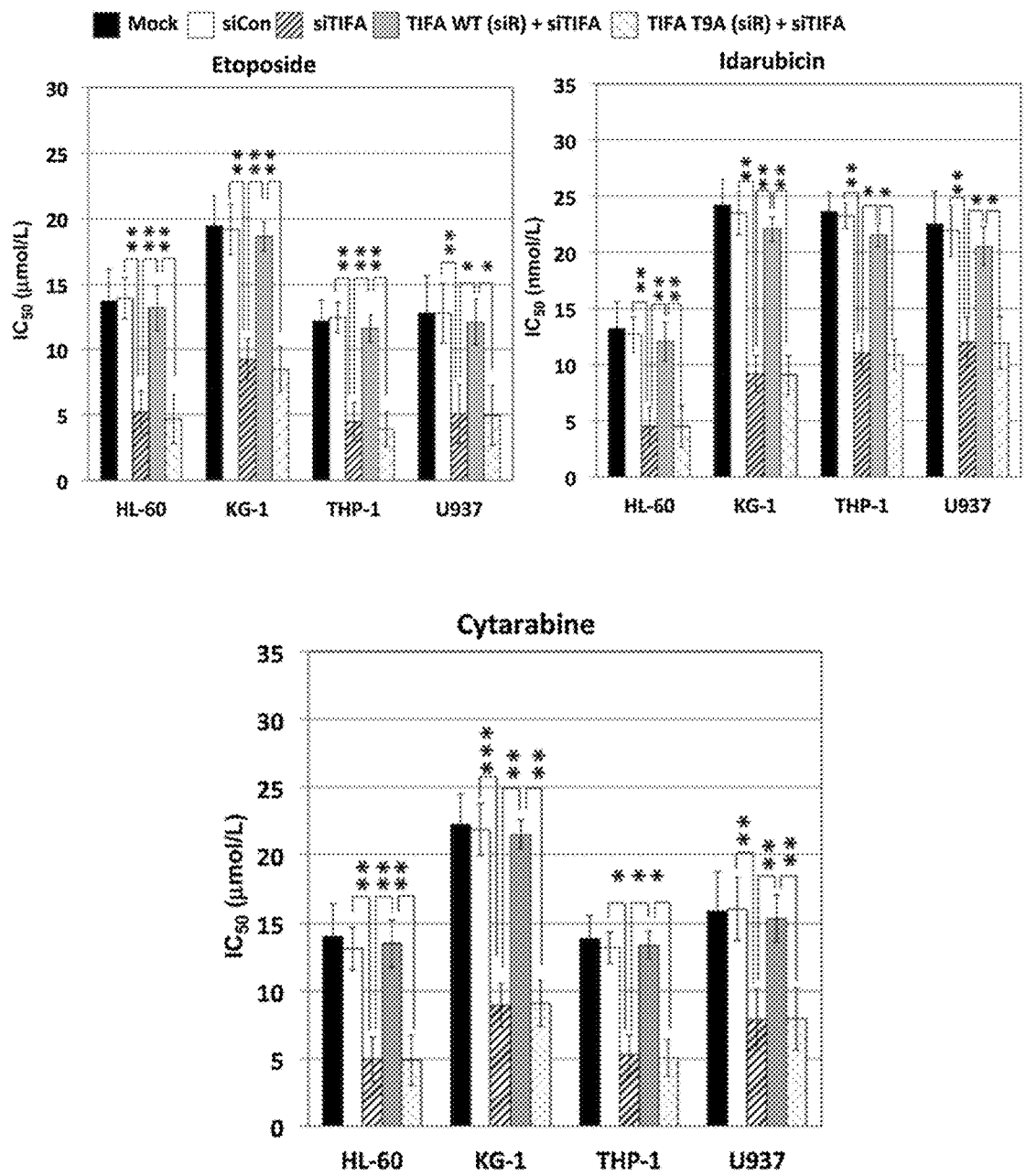
FIGS. 5A, 5B, 5C, 5D, 5E and 5F include charts showing that molecular targeting of TIFA inhibits TIFA-mediated NF-κB activation.

To address the molecular mechanism of targeting TIFA, we phenotypically rescued TIFA-depleted AML lines by wild-type TIFA and T9A mutant following a silencing-complementation strategy (27). The silencing-dependent chemosensitivity was efficiently alleviated upon expression of wild-type TIFA but not the T9A mutant in all tested AML lines (FIG. 5A), suggesting that pThr9-directed TIFA oligomerization is a key step required for the chemoresistance in AML.

Figure 5B:
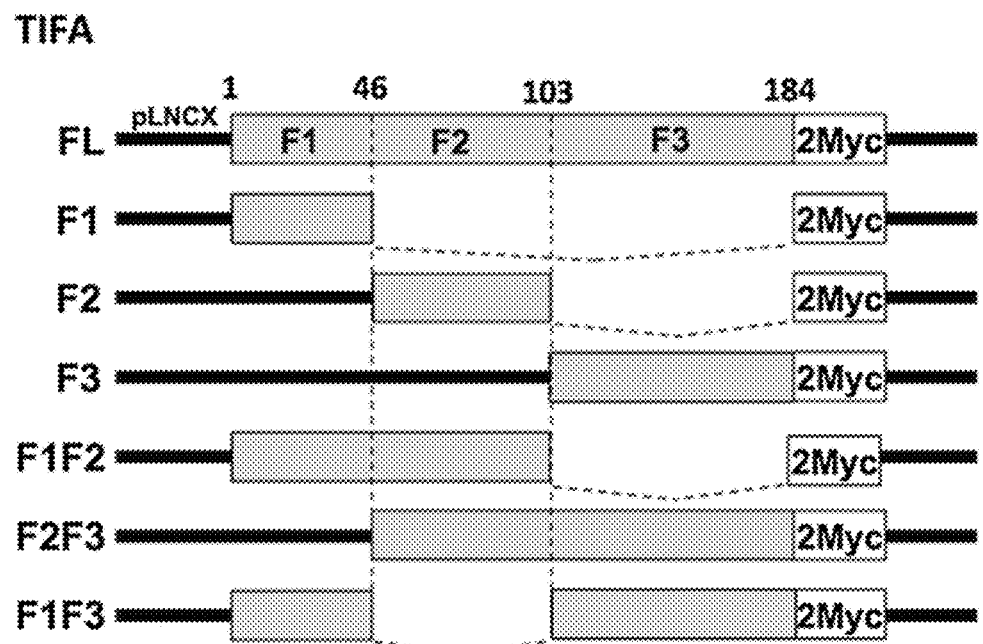
Figure 5C:
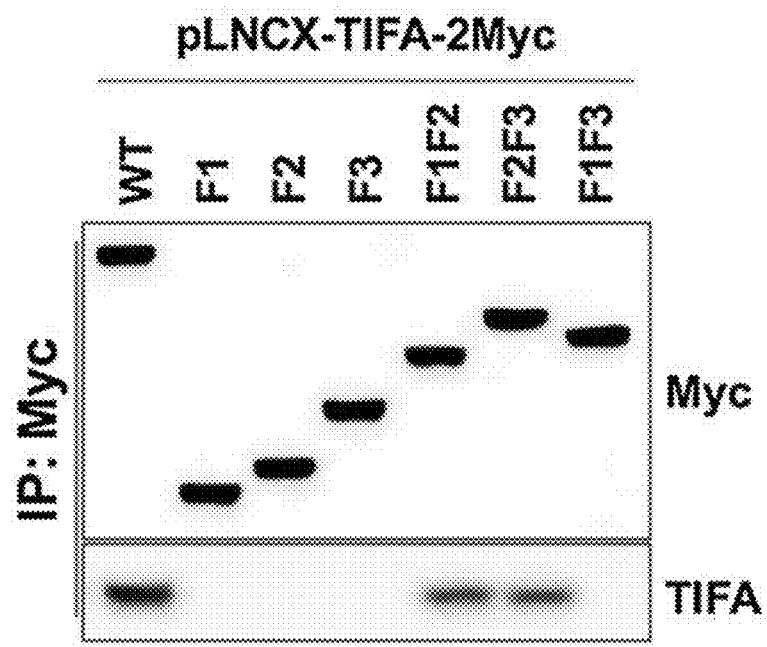
Figure 5D:
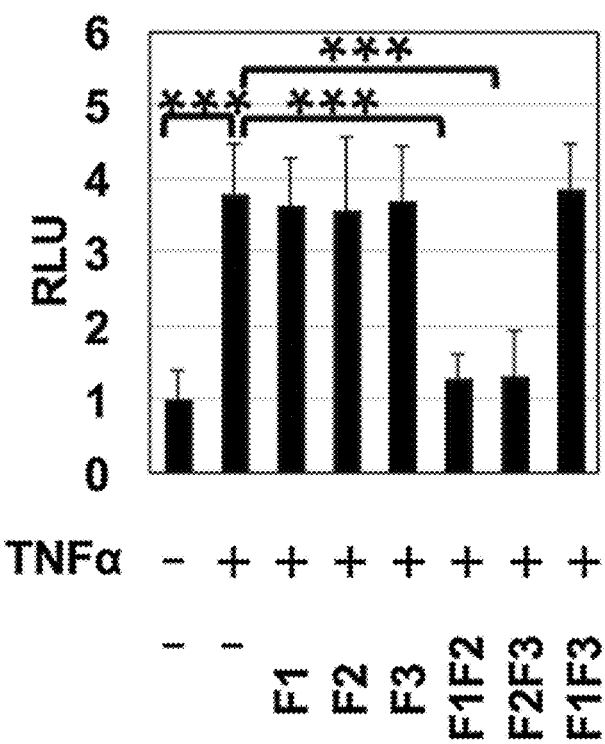
Figure 5E:
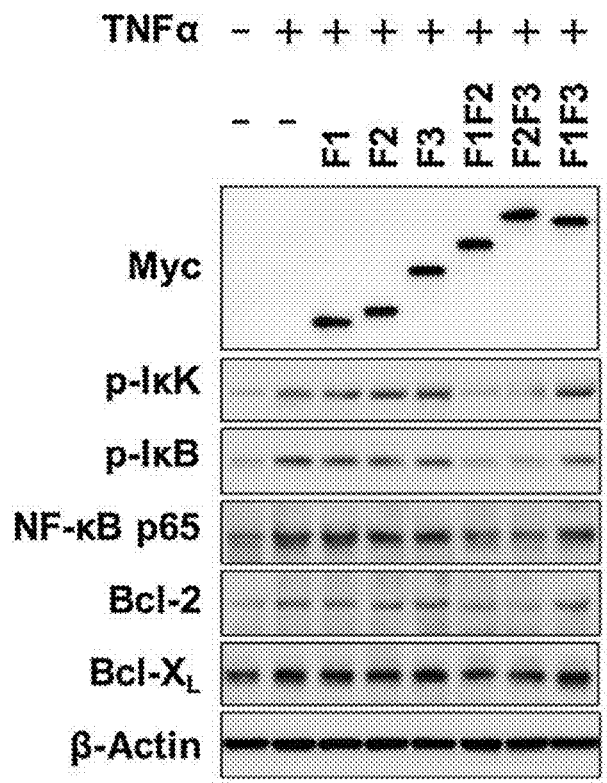
Figure 5F:
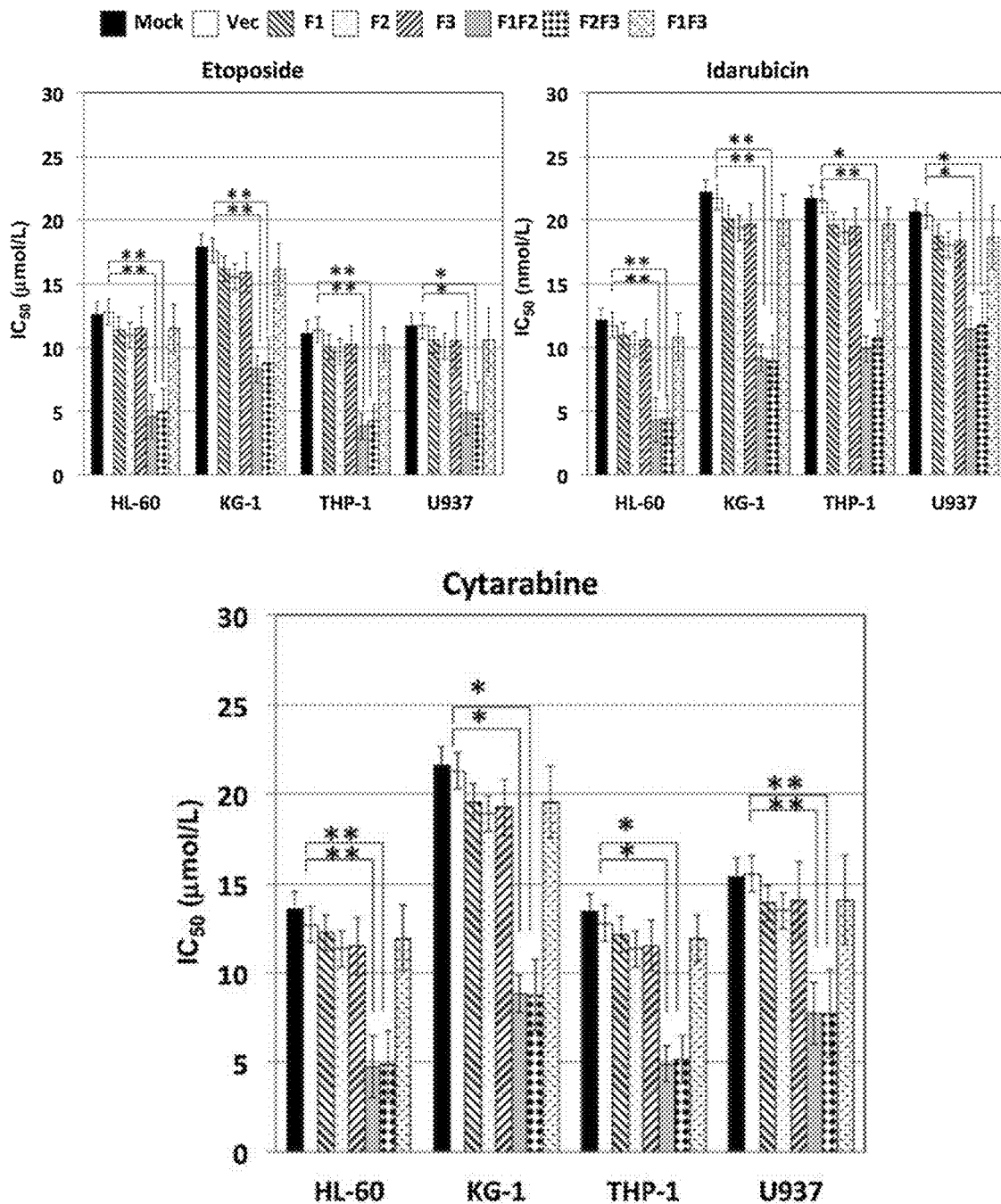

We next attempted to disrupt TIFA oligomerization through ectopic expression of DN fragments of TIFA in AML cells. We designed to fine-map the minimal effective region for molecular targeting of TIFA in AML cells through retroviral transduction (FIG. 5B). The immunoprecipitation of lysates from the transduced U937 cells showed that fragments F1F2 and F2F3, both containing the FHA dimerization-core with additional C- and N-terminal extensions, respectively, were able to pull down endogenous TIFA (FIG. 5C), suggesting that the two fragments are able to interfere with the self-association of endogenous TIFA (20). As a consequence, TNF-α-dependent NF-κB activation and elevations of NF-κB signaling factors were attenuated by F1F2 or F2F3 fragment in U937 cells (FIG. 5D-E). More significantly, the two DN fragments also significantly promoted chemosensitivities of AML lines with more than 50% decrease in IC50 (FIG. 5F). These observations collectively demonstrate the therapeutic potential of molecular targeting of TIFA in AML.

2.5 Targeting TIFA Potentiates the Clearance of Leukemic Myeloblasts

Figure 6A:
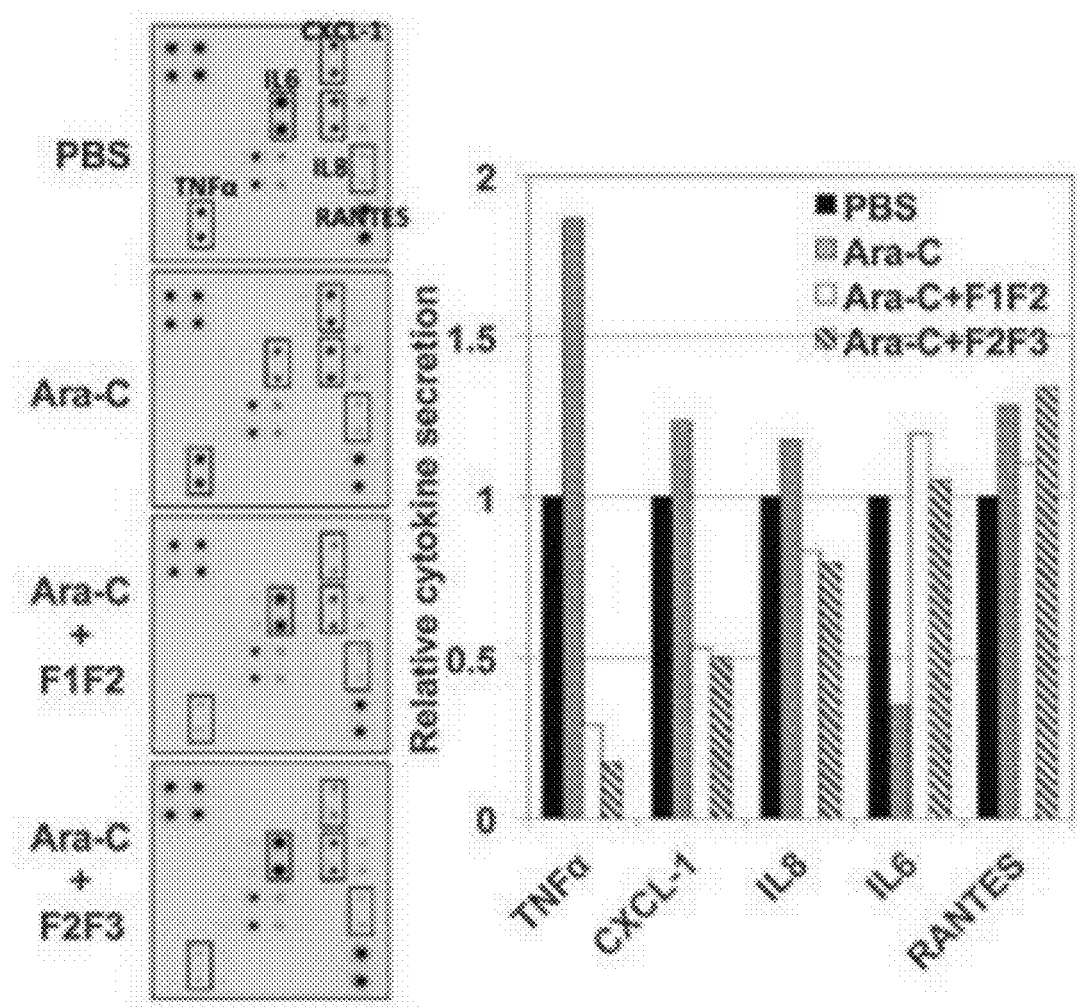
FIGS. 6A, 6B, 6C, 6D, 6E, 6F and 6G include charts showing that targeting TIFA potentiates the clearance of leukemic myeloblasts.
Figure 6B:
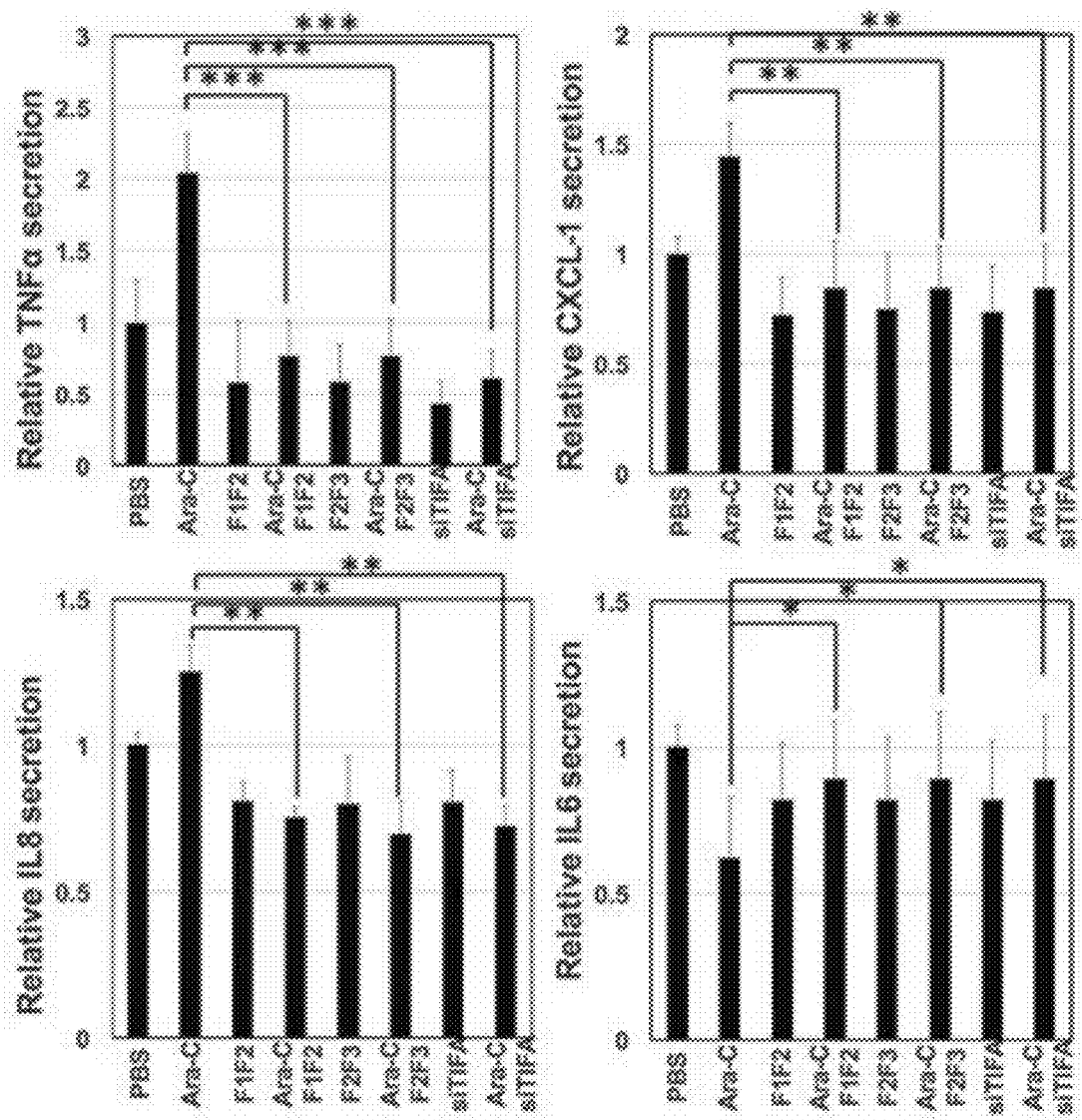
Figure 6C:
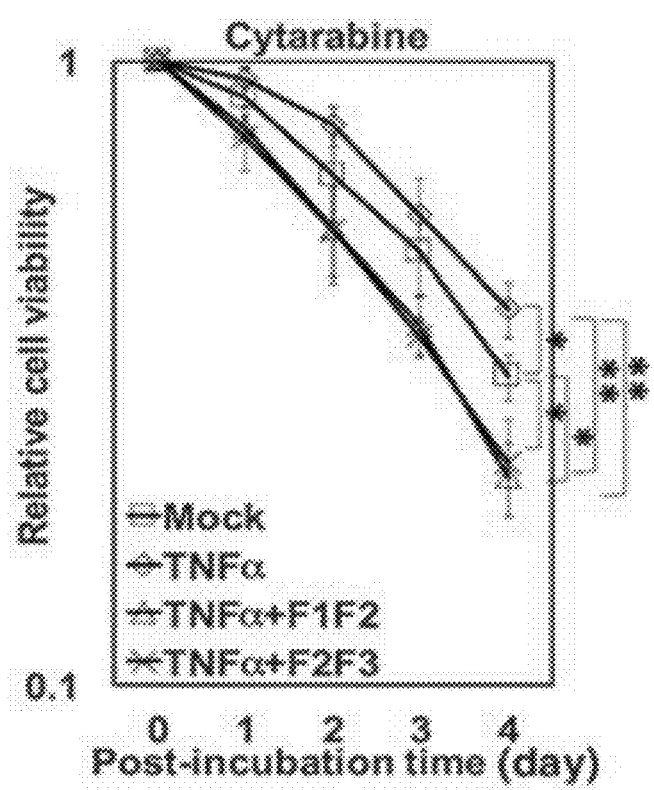
Figure 6D:
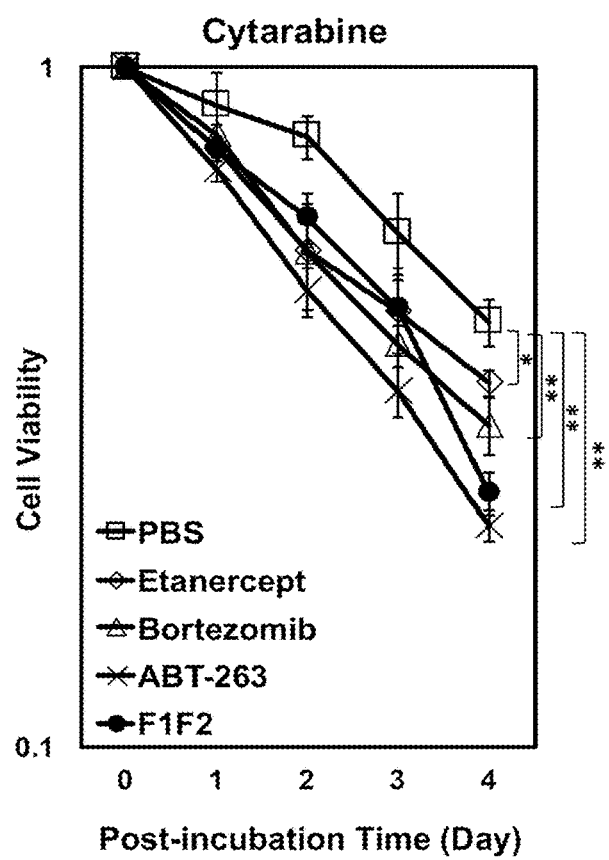

Aberrant secretion of cytokines contributes to pathogenesis of leukemia (39) and is considered a prognostic signature for recurrence of AML (39,40). We asked whether molecular targeting of TIFA can perturb NF-κB-dependent secretion of leukemic cytokines and attain better therapeutic efficacy. We performed cytokine antibody array to profile cytokines secreted by U937 cells. The result showed that cytarabine treatment promoted secretion of TNF-α, CXCL-1, and IL-8 but suppressed that of IL-6, while expression of TIFA DN fragments clearly led to opposite effects (FIG. 6A, with detailed ELISA analysis in FIG. 6B). With respect to promoted TNF-α secretion under cytarabine treatment, supplement of TNF-α was able to enhance the viability of U937 cells in response to cytarabine treatment, while expression of TIFA DN fragments significantly antagonized the effect of TNF-α (FIG. 6C). In support, inhibition of TNF-α and downstream NF-κB survival signaling by etanercept (Enbrel, TNF-α inhibitor), bortezomib (Velcade, NF-κB inhibitor), or ABT-263 (Navitoclax, BCL-2 inhibitor) enhanced the cytotoxicity of cytarabine-treated U937 cells, similar to the effect of TIFA DN fragment (FIG. 6D). These results suggest that TIFA DN fragments could be therapeutically effective to block secretion of inflammatory cytokines, leading to inactivation of NF-κB survival factors in AML.

Figure 6E:
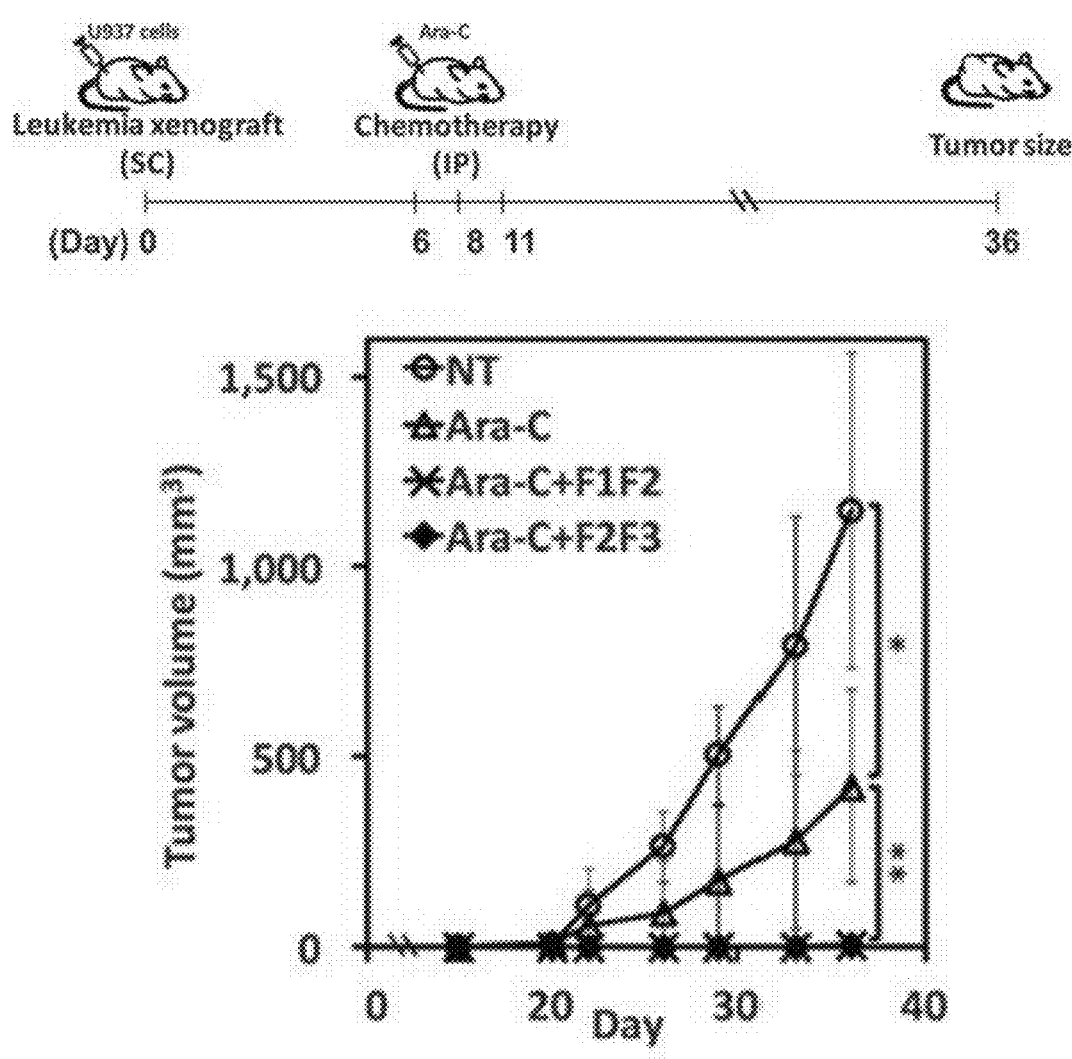
Figure 6F:
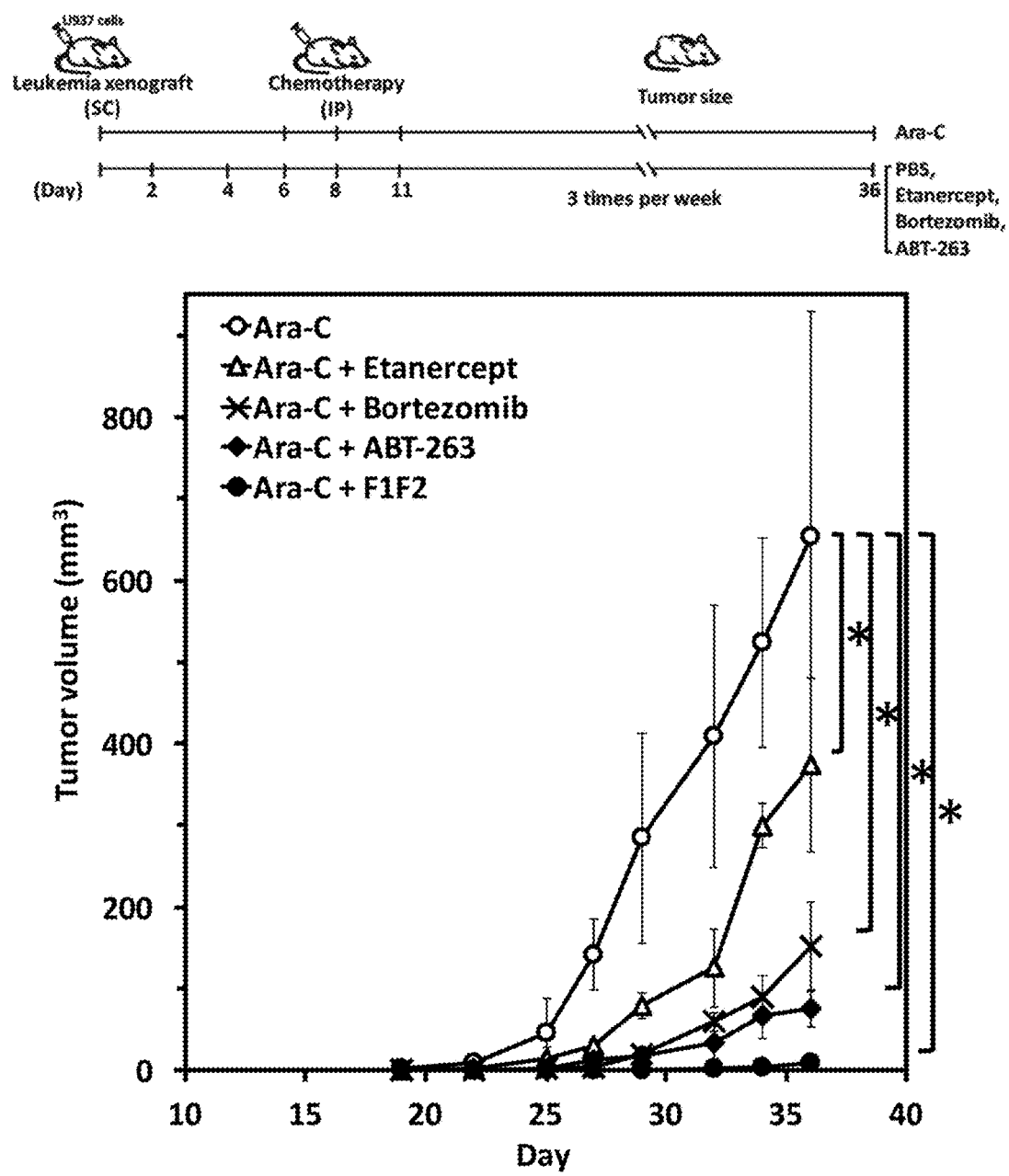
Figure 6G:
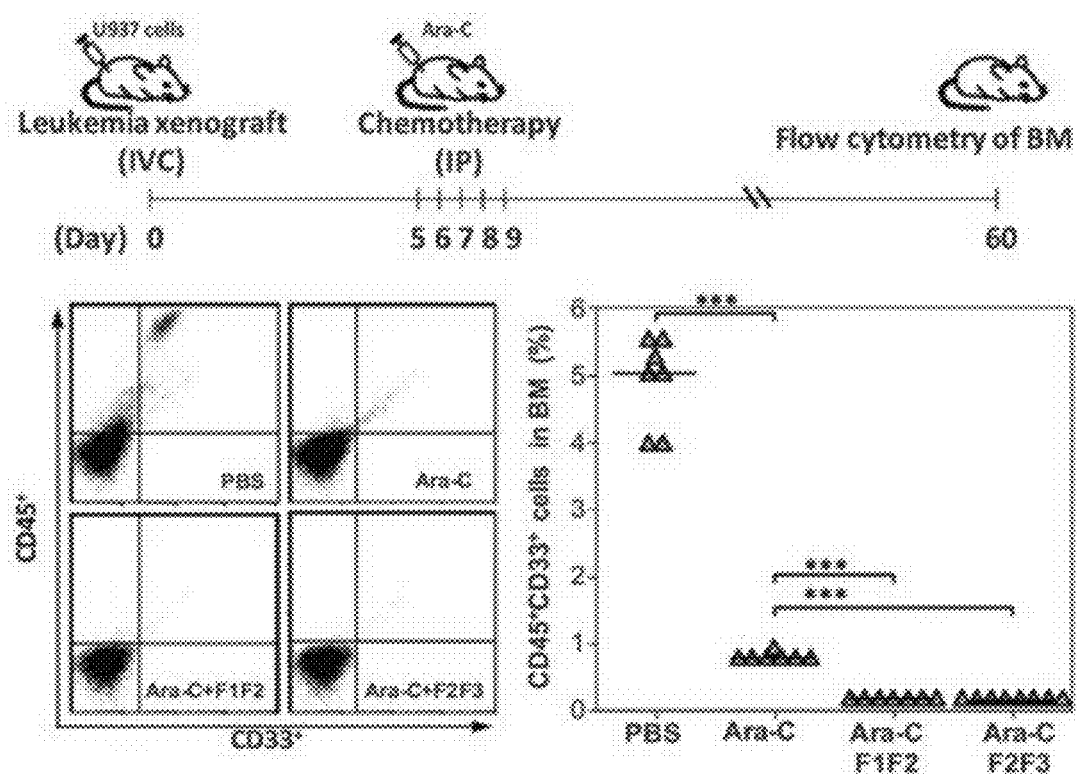

We therefore assessed the therapeutic potential of TIFA DN fragments in vivo. Although transplanted hematopoietic tissues proved difficult to propagate in nude mice compared to NOD-SCID or NSG/NOG mice (41), we chose this more difficult model to examine the effect of targeting TIFA. This is because the intact inflammatory cytokines required for proliferative myeloid progenitors could mimic a microenvironment to support chemoresistance (42). Ectopic xenograft model showed that retroviral transduction of TIFA DN fragments in addition to cytarabine treatment significantly prevented the expansion of myeloid sarcoma relative to cytarabine treatment alone (FIG. 6E,). Such prevention of AML expansion in vivo was also observed from inhibition of TNF-α, NF-κB, or BCL-2 (FIG. 6F), supporting that the enhanced chemotoxicity by targeting TIFA was likely due to blockage of the TNF-α-dependent NF-κB survival pathway. In addition, we also established an orthotopic xenograft model through direct injection of U937 stable cells via IVC in nude mice without immunosuppression by chemical or sub-lethal irradiation. Flow cytometry analysis of BM cells from recipient mice revealed that targeting TIFA significantly promotes the clearance of engrafted human CD45$^+$ CD33$^+$ myeloblasts upon cytarabine treatment (FIG. 6G). The constrained leukemic myeloblasts and fluctuated cytokines collectively suggest that molecular targeting of TIFA is able to perturb the positive-feedback between NF-κB and TNF-α that is required for progression of AML (43).

TIFA is a relatively new player in the NF-κB signaling pathway. Our earlier study uncovered the pivotal role of TIFA oligomerization in the promotion of NF-κB signaling pathway upon TNF-α stimulation, mechanistically through the inter-molecular binding between phosphorylated Thr9 and FHA domain of TIFA dimers (20). A recent study demonstrated that such phosphorylation-dependent oligomerization of TIFA is also triggered by a Gram-negative bacteria derived monosaccharide heptose-1,7-bisphosphate (HBP), leading to activation of innate immunity (23). In a separate paper (44), we further showed that TIFA mediates innate immune response through assembly of NLRP3 inflammasome. In this study we identified TIFA as the functional link between the Aurora A signaling axis and the NF-κB-regulated pro-survival factors in AML. In addition, we demonstrated the therapeutic potential of TIFA targeting in the treatment of AML by showing that TIFA inhibition perturbs leukemic cytokine secretion, significantly enhances chemotoxicity to AML cells, and potentiates the clearance of leukemic myeloblasts in a xenograft model.

Instead of conventional real-time PCR-based detection of prognostic factors at the transcriptional level, we directly assessed the TIFA protein level through western blot analysis of freshly collected patient samples. We observed elevated levels of the TIFA protein in AML patients compared to normal donors, similar to its kinase Aurora A, and demonstrated a tight correlation between TIFA and NF-κB driven pro-survival factors. By using immunocytochemical staining of cryopreserved patient myeloid cells, we also reasoned that the higher protein level of TIFA in BM is an independent factor of poor prognosis for OS in AML patients, irrespective of age, WBC counts, karyotype, and other genetic markers. These observations were corroborated by the finding that AML patients with higher TIFA protein level were more refractory to chemotherapy and had lower CR rates and poorer OS. Based on these findings, the higher TIFA protein level in BM could also serve as a novel biomarker that foresees the clinical outcome of AML patients. In agreement, silencing of TIFA or expression of dominant-negative TIFA fragments both impaired NF-κB activation, resulting in stalled leukemic cell proliferation and enhanced chemotoxicity.

Ectopic expression of DN protein can antagonize signal transduction and elicit therapeutic potential in cancer treatment. In particular, transfection of IκB super-repressor, a DN IκB mutant that ultimately inhibits NF-κB activity, was shown to selectively increase ALL sensitivity to vincristine treatment, through NF-κB-regulated apoptosis (45). We likewise observed an enhanced chemosensitivity in leukemic cells upon ectopic expression of two DN fragments of TIFA. We reasoned that the minimal DN fragment must include FHA dimerization-core plus either the N-terminal Thr9 motif for disruption of endogenous TIFA oligomerization or the C-terminal TRAF6/TRAF2 interacting motif for interruption of signal transduction (20,22). Intriguingly, both transcriptional inhibition (through TIFA siRNA; FIGS. 3 and 4) and molecular inhibition (through DN fragments; FIGS. 5 and 6) display almost identical targeting efficacies against TIFA, implicating the irreplaceable and non-redundant role of TIFA in these cellular processes.

Our results using AML, ALL, and CML lines consistently demonstrated the efficacy of targeting TIFA in both the myeloid and lymphoblastic lineages of leukemia, suggesting that the TIFA-driven NF-κB signaling axis may play a fundamental role during leukemogenesis. In addition, a positive feedback between NF-κB and TNF-α was recently described for leukemia initiation cells (LICs) in the promotion of leukemogenesis (43). LIC-enriched leukemic BM cells exhibit a constitutively activated NF-κB signaling, which is considered the cause of post-remission relapse of AML (43). In agreement, our result in FIG. 6C showed that TNF-α treatment did alleviate cytarabine cytotoxicity to undifferentiated U937 monocytes, while molecular inhibition of TIFA blocked the effect through perturbation of NF-κB-dependent pro-survival signaling (FIG. 5D-E). Leukemic cells were shown to be difficult to propagate in athymic nude mice due to remaining innate immunity (41). We nevertheless observed the homing of these undifferentiated monocytes in femurs of mice that was suppressed by cytarabine treatment (FIG. 6E), and that TIFA inhibition significantly promoted the effect. Although this xenograft model may not represent the true stemness of LICs, it may imply that the maintenance of undifferentiated leukemic cells under chemo drug treatment requires TIFA, and that the long-term expansion and self-renewal capacity of LICs could be impaired through targeting TIFA.

Deregulation of innate immunity and inflammatory signaling may lead to myelodysplastic syndromes (MDS), a group of heterogeneous clonal hematologic malignancies that overpopulates BM and progresses to AML (46). Constitutive NF-κB signalling may pathogenically transactivate inflammatory cytokines and pro-survival factors resulting in deregulated expansion of MDS BM progenitors, while inhibition of NF-κB activity induces apoptosis in normal and MDS BM precursors (47). Consequently, Bcl-2 and Bcl-$X_L$ are considered indicators for chemoresistance in myeloid malignancies including AML (9,12,48,49). Because TIFA regulates NF-κB-driven innate immunity (23), the leukemogenic role of TIFA we observed in AML is more likely through the NF-κB-dependent anti-apoptotic/pro-survival pathways. In agreement, our results using leukemic lines and AML patient-derived PBMCs consistently showed that TIFA is required for cell survival upon chemotherapies. In support, silencing of TIFA in patient PBMCs significantly blocked NF-κB-dependent pro-survival factors in spite of overexpressed Aurora A (FIG. 4C) and chemo drug treatment, suggesting that the loss of chemoresistance abilities we observed in FIGS. 3C, 4D, 5A, and 5F was due to perturbed anti-apoptotic/pro-survival factors Bcl2 and Bcl-$X_L$.

Tumor microenvironments are a milieu of proinflammatory responses coordinated by a great variety of inflammatory factors including cytokines and chemokines, and such tumor-promoting inflammation essentially enables cancer development (50). In agreement, a growing number of inhibitors that target proinflammatory TNF superfamily members have been shown to be therapeutically effective (51). Given the essential role of TIFA underlying the signaling chain between TNF-α and NF-κB, its inhibition should be able to attenuate inflammatory factors that are transcriptionally regulated by NF-κB. We observed attenuation of CXCL-1 and IL-8 secretions upon molecular targeting of TIFA coherent with delayed leukemic cell growth and reduced chemoresistance (FIG. 6A-B), which supports previously suggested tumorigenic function of the two inflammatory factors (52,53).

It has been well established that Aurora A is overexpressed in AML (16,18,54), and its inhibition was proposed as the targeted therapy to treat several hematopoietic malignancies (55-57). Although gene amplification of Aurora A was frequently observed from many types of solid tumors leading to overexpression and tumor progression (58), whether Aurora A is upregulated through this manner in AML remains elusive. We identified that TIFA is linked to TNF-α-dependent NF-κB survival signal through a site-specific phosphorylation that functionally requires the kinase activity of Aurora A, through which a positive feedback loop is sustained to trigger inflammatory responses and support chemoresistance of leukemic cells (40). In support, we observed enhanced chemotoxicity of AML cells under treatments of TNF-α, BCL-2, and Aurora A inhibitors, similar to transcriptional inhibition and molecular targeting of TIFA (FIG. 3, 4, 5, 6C). The translational implication was further strengthened by combined treatment of cytarabine with inhibitor of TNF-α, NF-κB, or BCL-2 in vivo (FIG. 6F).

Overall, our results demonstrate the functional role of TIFA in supporting the Aurora A-dependent NF-κB survival and inflammatory pathways as the molecular basis underlying leukemic cell growth and chemoresistance in AML. As the initial treatment approach using anthracycline or cytarabine has remained unchanged for decades and CR is still poorly achieved due to drug resistance, future AML treatment with TIFA-targeted strategy might provide therapeutic advantages to lower the incidences of chemoresistance, enhance the efficacy of conventional chemotherapies, and improve the long-term clinical outcome.

Sequence Information

TABLE 4

| F1 fragment | SEQ ID NO |
|---|---|
| F1 (Homo sapiens)<br>MTSFEDADTE ETVTCLQMTV YHPGQLQCGI FQSISFN-RE KLPSSE | 23 |
| F1 (Oryctolagus cuniculus)<br>MSSFEDADTE ETVTCLQMTV YHPAQFQSGI FQAIDENKRD KLPSSE | 24 |
| F1 (Canis lupus familiaris)<br>MMSNFEDADTE ETVTCLQITV YHPGQLQNGI FQSIRFYNRE KLPSSE | 25 |
| F1 (Mus Musculus)<br>MSTFEDADTE ETVTCLQMTI YHP-GQQSGI FKSIRFCSKE KFPSIE | 26 |
| F1 (Rattus norvegicus)<br>MSTFEDADTE ETVTCLQMTI YHPGQLQSGI FKSIRFCSKE KFPSIE | 27 |
| F1 (Cricetulus griseus)<br>MSSFEDADTE ETVTCLQLTV YHPGQLQSGI FKSIRFCNKE KFPSIE | 28 |
| F1 (Castor canadensis)<br>MSNFEDADTE ETLTCLHVTV YHSGKSHNGV FQSIEFYNRE KLPSGE | 29 |
| F1 (Cavia porcellus)<br>MSSFEDADTQ ETVTCLQMTV YHPGHVQRGI FRSINFSKRE KLPSSE | 30 |
| F1 (Bos Taurus)<br>MSSFEDADTE EMVTCLQMTL YHPGHQRSGI FRSIKFFNRE KLPTSE | 31 |
| F1 (Capra hircus)<br>MSSFEDVDTE ETVTSLHMTL YHPGHQRSGI FQSIKFCNRE TLPTSE | 32 |
| F1 (Sus scrofa)<br>MSSFEDADTE ETLTCLQMTV YHPGHQQNGI FQSRRFFSRE KLPSSE | 33 |
| F1 (Equus caballus)<br>MSSFEDADTE ETLTCLQMTV YHPGQQPNGI FQSIGFHKRE KLPSRE | 34 |
| F2 fragment | SEQ ID NO |
| F2 (Homo sapiens)<br>VVKF GRNSNICHYT FQDKQVSRVQ FSLQLFKKFN SSVLSFEIKN<br>MSKKTNLIVD SREL | 35 |
| F2 (Oryctolagus cuniculus)<br>VVKF GRNSKVCHYT FQDKQASRVQ FSLQLFKQFN SSVLSFEIKN<br>MSRKTSLIVD SQEL | 36 |
| F2 (Canis lupus familiaris)<br>VVKF GRNSNICRYT FQDKQVSRVQ FSLQLFKKFD SSVLSFEIKN<br>MSKKTNLLVD NKEL | 37 |
| F2 (Mus musculus)<br>VVKF GRNSNMCQYT FQDKQVSRIQ FVLQPFKQFN SSVLSFEIKN<br>MSKKTSLMVD NQEL | 38 |
| F2 (Rattus norvegicus)<br>VVKF GRNSNMCQYT FQDKQVSRVQ FALQPFKQFN SSVLSFEIKN<br>MSKKTSLMVD NQEL | 39 |
| F2 (Cricetulus griseus)<br>EVKF GRNSNICRYT FQDKQVSRVQ FALQPFKQFN SSVLSFEIKN<br>MSKKTSLMVD NQEL | 40 |
| F2 (Castor canadensis)<br>VVKF GRNSSICRYT FQDKQVSRVQ FSLQPFKQFN SSVLSFEIKN<br>MSKKTSLIVD SQEL | 41 |
| F2 (Cavia porcellus)<br>VVKF GRNSSSCHYI FQDKQASRVQ FSLHPFKPFN SSVLSFEIKN<br>LSKKTSLIVD SREL | 42 |

TABLE 4-continued

| | SEQ ID NO |
|---|---|
| F2 (*Bos Taurus*)<br>VVKF GRNSHTCNYI FQDKQVSRVQ FSLQVFKKFN SSVVSFEIHN MSKKTSLLVD NKEL | 43 |
| F2 (*Capra hircus*)<br>VVKF GRNSSTCRYT FQDKQVSRVQ FSLQLFKKFD SSVVSFEIKN MSKKTNLLVD DKEL | 44 |
| F2 (*Sus scrofa*)<br>VVKF GRNSICQYT FQDKHASRVQ FSLHLFKKFD SSVLSFEIKN MSKKTSLIVD NQEL | 45 |
| F2 (*Equus caballus*)<br>EVKF GRSSKVCNYT FQDRQVSRVQ FSLQLFKKFD SSVLSFEIKN MSKRTSLIVD NRTL | 46 |

| F3 fragment | SEQ ID NO |
|---|---|
| F3 (*Homo sapiens*)<br>GYLNKM DLPYRCMVRF GEYQFLMEKE DGESLEFFET QFILSPRSLL QENNWPPHRP IPEYGTYSLC S-SQSSSPTE MDENES | 47 |
| F3 (*Oryctolagus cuniculus*)<br>GYLNKL DLPYKCMVRF SEYQFLMEKE DGEALDSFET QFILSPRPLL QENIWPPHKP IPEYGIYSSC S-AQSTSPTE MDEDEL | 48 |
| F3 (*Canis lupus familiaris*)<br>CYLNKI DLPYKCMVRF GEYQFLIEKE DGESLEFFET QFILSPRSLL QENNWPIQKP IPEYGSYSSC F-TQNTSPTE MDENEL | 49 |
| F3 (*Mus musculus*)<br>GYLNKM DLPYKCMLRF GEYQFLLQKE DGESVESFET QFIMSSRPLL QENNWPTQNP IPEDGMYSSY F-THRSSPSE MDENEL | 50 |
| F3 (*Rattus norvegicus*)<br>GYLNKM DLPYKCMLRF GEYQFLLQKE DGESVESFET QFILSPRPLL QENNWPTQSP IPEDGVYSSY F-THRSSPAE MDENEL | 51 |
| F3 (*Cricetulus griseus*)<br>GYLNKM DLPYKCLLRF GEYQFLLEKE DGESVESFET QFILSPRPLL QENNWPTQSP IPEDGGYSSY F-THRTSPTE MDENEL | 52 |
| F3 (*Castor canadensis*)<br>GYLNKM DLPYRCMVRF GEYQFLLEKE DGESLESFQT HFILSPRPLL QENNWPAQTP IPEDGGYSSY L-TPSTFPTE IDENEL | 53 |
| F3 (*Cavia porcellus*)<br>RYLNKM DLPYRCMVRF GEYQFLLERE DGESLESFET QFVFSPRPLL QENSWPTQSP IPEDGSFSSG Y-TRSSFPME MDENEW | 54 |
| F3 (*Bos Taurus*)<br>GYLNKM DLPDKCMIRF GDYQFLVEKE DGESLEFFEI QFSLSKKPLL QENNWLSQEP IPECGSYSSC L-TQNNSPME VGENEW | 55 |
| F3 (*Capra hircus*)<br>SYLNKM DLPDKCLIRF GDYQFLVEKE DGESLEFFEI QFFLSIRPLL QENKWLPQKP TPECGSCSPC S-TQNNSPME AGENEW | 56 |
| F3 (*Sus scrofa*)<br>GYLNKM DLPPKCMVRF GDYQFLIEKE DGESLEFFEI QFILSTRSLL QENNWLPQKP IPECGNYLSC S-TQGNSPIE MGENEW | 57 |
| F3 (*Equus caballus*)<br>DFLHKV DLPDRCMIRF GDYQILMEKE DGVSLEFFET EFILSPRSLL QKNYWPPQNP IPEYCHSVWS S-SQSTSPME TDENE | 58 |

| C-terminal loop sequence in F3 fragment | SEQ ID NO |
|---|---|
| (*Homo sapiens*)<br>SPRSLL QENNWPPHRP IPEYGTYSLC S-SQSSSPTE MDENES | 59 |
| (*Oryctolagus cuniculus*)<br>SPRPLL QENIWPPHKP IPEYGIYSSC S-AQSTSPTE MDEDEL | 60 |
| (*Canis lupus familiaris*)<br>SPRSLL QENNWPIQKP IPEYGSYSSC F-TQNTSPTE MDENEL | 61 |
| (*Mus musculus*)<br>SSRPLL QENNWPTQNP IPEDGMYSSY F-THRSSPSE MDENEL | 62 |

TABLE 4-continued (Rattus norvegicus) 63
SPRPLL QENNWPTQSP IPEDGVYSSY F-THRSSPAE MDENEL (Cricetulus griseus) 64
SPRPLL QENNWPTQSP IPEDGGYSSY F-THRTSPTE MDENEL (Castor canadensis) 65
SPRPLL QENNWPAQTP IPEDGGYSSY L-TPSTFPTE IDENEL (Cavia porcellus) 66
SPRPLL QENSWPTQSP IPEDGSFSSG Y-TRSSFPME MDENEW (Bos Taurus) 67
SKKPLL QENNWLSQEP IPECGSYSSC L-TQNNSPME VGENEW (Capra hircus) 68
SIRPLL QENKWLPQKP TPECGSCSPC S-TQNNSPME AGENEW (Sus scrofa) 69
STRSLL QENNWLPQKP IPECGNYLSC S-TQGNSPIE MGENEW (Equus caballus) 70
SPRSLL QKNYWPPQNP IPEYCHSVWS S-SQSTSPME TDENE

TABLE 5

| TIFA peptide fragment | SEQ ID NO: | TIFA peptide fragment | SEQ ID NO: |
| --- | --- | --- | --- |
| F1 + F2 (Homo sapiens)<br>MTSFEDADTE ETVTCLQMTV<br>YHPGQLQCGI FQSISFN-RE<br>KLPSSEVVKF GRNSNICHYT<br>FQDKQVSRVQ FSLQLFKKFN<br>SSVLSFEIKN MSKKTNLIVDSREL | 71 | F2 + F3 (Homo sapiens)<br>VVKF GRNSNICHYT FQDKQVSRVQ<br>FSLQLFKKFN SSVLSFEIKN<br>MSKKTNLIVD SRELGYLNKM<br>DLPYRCMVRF GEYQFLMEKE<br>DGESLEFFET QFILSPRSLL<br>QENNWPPHRP IPEYGTYSLC<br>SSQSSSPTE MDENES | 83 |
| F1 + F2 (Oryctolagus cuniculus)<br>MSSFEDADTE ETVTCLQMTV<br>YHPAQFQSGI FQAIDFNKRD<br>KLPSSEVVKF GRNSKVCHYT<br>FQDKQASRVQ FSLQLFKQFN<br>SSVLSFEIKN MSRKTSLIVDSQEL | 72 | F2 + F3 (Oryctolagus cuniculus)<br>VVKF GRNSKVCHYT FQDKQASRVQ<br>FSLQLFKQFN SSVLSFEIKN<br>MSRKTSLIVD SQELGYLNKL<br>DLPYKCMVRF SEYQFLMEKE<br>DGEALDSFET QFILSPRPLL<br>QENIWPPHKP IPEYGIYSSC<br>S-AQSTSPTE MDEDEL | 84 |
| F1 + F2 (Canis lupus familiaris)<br>MMSNFEDADTE ETVTCLQITV<br>YHPGQLQNGI FQSIRFYNRE<br>KLPSSEVVKF GRNSNICRYT<br>FQDKQVSRVQ FSLQLFKKED<br>SSVLSFEIKN MSKKTNLLVDSQEL | 73 | F2 + F3 (Canis lupus familiaris)<br>VVKF GRNSNICRYT FQDKQVSRVQ<br>FSLQLFKKFD SSVLSFEIKN<br>MSKKTNLLVD NKELCYLNKI<br>DLPYKCMVRF GEYQFLIEKE<br>DGESLEFFET QFILSPRSLL<br>QENNWPIQKP IPEYGSYSSC<br>F-TQNTSPTE MDENEL | 85 |
| F1 + F2 (Mus musculus)<br>MSTFEDADTE ETVTCLQMTI<br>YHP-GQQSGI FKSIRFCSKE<br>KFPSIEVVKF GRNSNMCQYT<br>FQDKQVSRIQ FVLQPFKQFN<br>SSVLSFEIKN MSKKTSLMVDNQEL | 74 | F2 + F3 (Mus musculus)<br>VVKF GRNSNMCQYT FQDKQVSRIQ<br>FVLQPFKQFN SSVLSFEIKN<br>MSKKTSLMVD NQELGYLNKM<br>DLPYKCMLRF GEYQFLLQKE<br>DGESVESFET QFIMSSRPLL<br>QENNWPTQNP IPEDGMYSSY<br>F-THRSSPSE MDENEL | 86 |
| F1 + F2 (Rattus norvegicus)<br>MSTFEDADTE ETVTCLQMTI<br>YHPGQLQSGI FKSIRFCSKE<br>KFPSIEVVKF GRNSNMCQYT<br>FQDKQVSRVQ FALQPFKQFN<br>SSVLSFEIKN MSKKTSLMVDNQEL | 75 | F2 + F3 (Rattus norvegicus)<br>VVKF GRNSNMCQYT FQDKQVSRVQ<br>FALQPFKQFN SSVLSFEIKN<br>MSKKTSLMVD NQELGYLNKM<br>DLPYKCMLRF GEYQFLLQKE<br>DGESVESFET QFILSPRPLL<br>QENNWPTQSP IPEDGVYSSY<br>F-THRSSPAE MDENEL | 87 |

TABLE 5-continued

| TIFA peptide fragment | SEQ ID NO: | TIFA peptide fragment | SEQ ID NO: |
|---|---|---|---|
| F1 + F2 (Cricetulus griseus)<br>MSSFEDADTE ETVTCLQLTV<br>YHPGQLQSGI FKSIRFCNKE<br>KFPSIEEVKF GRNSNICRYT<br>FQDKQVSRVQ FALQPFKQFN<br>SSVLSFEIKN MSKKTSLMVDNQEL | 76 | F2 + F3 (Cricetulus griseus)<br>EVKF GRNSNICRYT FQDKQVSRVQ<br>FALQPFKQFN SSVLSFEIKN<br>MSKKTSLMVD NQELGYLNKM<br>DLPYKCLLRF GEYQFLLEKE<br>DGESVESFET QFILSPRPLL<br>QENNWPTQSP IPEDGGYSSY<br>F-THRTSPTE MDENEL | 88 |
| F1 + F2 (Castor canadensis)<br>MSNFEDADTE ETLTCLHVTV<br>YHSGKSHNGV FQSIEFYNRE<br>KLPSGEVVKF GRNSSICRYT<br>FQDKQVSRVQ FSLQPFKQFN<br>SSVLSFEIKN MSKKTSLIVDSQEL | 77 | F2 + F3 (Castor canadensis)<br>VVKF GRNSSICRYT FQDKQVSRVQ<br>FSLQPFKQFN SSVLSFEIKN<br>MSKKTSLIVD SQELGYLNKM<br>DLPYRCMVRF GEYQFLLEKE<br>DGESLESFQT HFILSPRPLL<br>QENNWPAQTP IPEDGGYSSY<br>L-TPSTFPTE IDENEL | 89 |
| F1 + F2 (Cavia porcellus)<br>MSSFEDADTQ ETVTCLQMTV<br>YHPGHVQRGI FRSINFSKRE<br>KLPSSEVVKF GRNSSSCHYI<br>FQDKQASRVQ FSLHPFKPFN<br>SSVLSFEIKN LSKKTSLIVDSREL | 78 | F2 + F3 (Cavia porcellus)<br>VVKF GRNSSSCHYI FQDKQASRVQ<br>FSLHPFKPFN SSVLSFEIKN<br>LSKKTSLIVD SRELRYLNKM<br>DLPYRCMVRF GEYQFLLERE<br>DGESLESFET QFVFSPRPLL<br>QENSWPTQSP IPEDGSFSSG<br>Y-TRSSFPME MDENEW | 90 |
| F1 + F2 (Bos Taurus)<br>MSSFEDADTE EMVTCLQMTL<br>YHPGHQRSGI FRSIKFFNRE<br>KLPTSEVVKF GRNSHTCNYI<br>FQDKQVSRVQ FSLQVFKKFN<br>SSVVSFEIKN MSKKTSLLVDNKEL | 79 | F2 + F3 (Bos Taurus)<br>VVKF GRNSHTCNYI FQDKQVSRVQ<br>FSLQVFKKFN SSVVSFEIKN<br>MSKKTSLLVD NKELGYLNKM<br>DLPDKCMIRF GDYQFLVEKE<br>DGESLEFFEI QFSLSKKPLL<br>QENNWLSQEP IPECGSYSSC<br>L-TQNNSPME VGENEW | 91 |
| F1 + F2 (Capra hircus)<br>MSSFEDVDTE ETVTSLHMTL<br>YHPGHQRSGI FQSIKFCNRE<br>TLPTSEVVKF GRNSSTCRYT<br>FQDKQVSRVQ FSLQLFKKFD<br>SSVVSFEIKN MSKKTNLLVDDKEL | 80 | F2 + F3 (Capra hircus)<br>VVKF GRNSSTCRYT FQDKQVSRVQ<br>FSLQLFKKFD SSVVSFEIKN<br>MSKKTNLLVD DKELSYLNKM<br>DLPDKCLIRF GDYQFLVEKE<br>DGESLEFFEI QFFLSIRPLL<br>QENKWLPQKP TPECGSCSPC<br>S-TQNNSPME AGENEW | 92 |
| F1 + F2 (Sus scrofa)<br>MSSFEDADTE ETLTCLQMTV<br>YHPGHQQNGI FQSRRFFSRE<br>KLPSSEVVKF GRNS-ICQYT<br>FQDKHASRVQ FSLHLFKKFD<br>SSVLSFEIKN MSKKTSLIVDNQEL | 81 | F2 + F3 (Sus scrofa)<br>VVKF GRNS-ICQYT FQDKHASRVQ<br>FSLHLFKKFD SSVLSFEIKN<br>MSNKTSLIVD NQELGYLNKM<br>DLPPKCMVRF GDYQFLIEKE<br>DGESLEFFEI QFILSTRSLL<br>QENNWLPQKP IPECGNYLSC<br>S-TQGNSPIE MGENEW | 93 |
| F1 + F2 (Equus caballus)<br>MSSFEDADTE ETLTCLQMTV<br>YHPGQQPNGI FQSIGFHKRE<br>KLPSREEVKF GRSSKVCNYT<br>FQDRQVSRVQ FSLQLFKKED<br>SSVLSFEIKN MSKRTSLIVDNRTL | 82 | F2 + F3 (Equus caballus)<br>EVKF GRSSKVCNYT FQDRQVSRVQ<br>FSLQLFKKFD SSVLSFEIKN<br>MSKRTSLIVD NRTLDFLHKV<br>DLPDRCMIRF GDYQILMEKE<br>DGVSLEFFET EFILSPRSLL<br>QKNYWPPQNP IPEYCHSVWS<br>S-SQSTSPME TDENEL | 94 |

REFERENCES

1. Estey, E., and Dohner, H. (2006) Acute myeloid leukaemia. *Lancet* 368, 1894-1907
2. Appelbaum, F. R., Gundacker, H., Head, D. R., Slovak, M. L., Willman, C. L., Godwin, J. E., Anderson, J. E., and Petersdorf, S. H. (2006) Age and acute myeloid leukemia. *Blood* 107, 3481-3485
3. Komanduri, K. V., and Levine, R. L. (2016) Diagnosis and Therapy of Acute Myeloid Leukemia in the Era of Molecular Risk Stratification. *Annu Rev Med* 67, 59-72
4. Lai, C., Karp, J. E., and Hourigan, C. S. (2016) Precision medicine for acute myeloid leukemia. *Expert Rev Hematol* 9, 1-3
5. Hayden, M. S., and Ghosh, S. (2012) NF-kappaB, the first quarter-century: remarkable progress and outstanding questions. *Genes & development* 26, 203-234
6. Hoesel, B., and Schmid, J. A. (2013) The complexity of NF-kappaB signaling in inflammation and cancer. *Mol Cancer* 12, 86
7. Chaturvedi, M. M., Sung, B., Yadav, V. R., Kannappan, R., and Aggarwal, B. B. (2011) NF-kappaB addiction and its role in cancer: 'one size does not fit all'. *Oncogene* 30, 1615-1630
8. Tergaonkar, V., Pando, M., Vafa, O., Wahl, G., and Verma, I. (2002) p53 stabilization is decreased upon NFkappaB activation: a role for NFkappaB in acquisition of resistance to chemotherapy. *Cancer cell* 1, 493-503
9. Mehta, S. V., Shukla, S. N., and Vora, H. H. (2013) Overexpression of Bcl2 protein predicts chemoresistance in acute myeloid leukemia: its correlation with FLT3. *Neoplasma* 60, 666-675
10. Zhou, J., Ching, Y. Q., and Chng, W. J. (2015) Aberrant nuclear factor-kappa B activity in acute myeloid leukemia: from molecular pathogenesis to therapeutic target. *Oncotarget* 6, 5490-5500
11. Griessinger, E., Frelin, C., Cuburu, N., Imbert, V., Dageville, C., Hummelsberger, M., Sirvent, N., Dreano, M., and Peyron, J. F. (2008) Preclinical targeting of NF-kappaB and FLT3 pathways in AML cells. *Leukemia* 22, 1466-1469
12. Braun, T., Carvalho, G., Fabre, C., Grosjean, J., Fenaux, P., and Kroemer, G. (2006) Targeting NF-kappaB in hematologic malignancies. *Cell Death Differ* 13, 748-758
13. Carmena, M., and Earnshaw, W. C. (2003) The cellular geography of aurora kinases. *Nature reviews. Molecular cell biology* 4, 842-854
14. Hilton, J. F., and Shapiro, G. I. (2014) Aurora kinase inhibition as an anticancer strategy. *Journal of clinical oncology: official journal of the American Society of Clinical Oncology* 32, 57-59
15. Ye, D., Garcia-Manero, G., Kantarjian, H. M., Xiao, L., Vadhan-Raj, S., Fernandez, M. H., Nguyen, M. H., Medeiros, L. J., and Bueso-Ramos, C. E. (2009) Analysis of Aurora kinase A expression in CD34(+) blast cells isolated from patients with myelodysplastic syndromes and acute myeloid leukemia. *J Hematop* 2, 2-8
16. Yang, J., Ikezoe, T., Nishioka, C., Nobumoto, A., Udaka, K., and Yokoyama, A. (2013) CD34(+)/CD38(−) acute myelogenous leukemia cells aberrantly express Aurora kinase A. *International journal of cancer Journal international du cancer* 3, 2706-2719
17. Briassouli, P., Chan, F., Savage, K., Reis-Filho, J. S., and Linardopoulos, S. (2007) Aurora-A regulation of nuclear factor-kappaB signaling by phosphorylation of IkappaBalpha. *Cancer research* 67, 1689-1695
18. Huang, X. F., Luo, S. K., Xu, J., Li, J., Xu, D. R., Wang, L. H., Yan, M., Wang, X. R., Wan, X. B., Zheng, F. M., Zeng, Y. X., and Liu, Q. (2008) Aurora kinase inhibitory VX-680 increases Bax/Bcl-2 ratio and induces apoptosis in Aurora-A-high acute myeloid leukemia. *Blood* 111, 2854-2865
19. Giles, F. J., Cortes, J., Jones, D., Bergstrom, D., Kantarjian, H., and Freedman, S. J. (2007) MK-0457, a novel kinase inhibitor, is active in patients with chronic myeloid leukemia or acute lymphocytic leukemia with the T315I BCR-ABL mutation. *Blood* 109, 500-502
20. Huang, C. C., Weng, J. H., Wei, T. Y., Wu, P. Y., Hsu, P. H., Chen, Y. H., Wang, S. C., Qin, D., Hung, C. C., Chen, S. T., Wang, A. H., Shyy, J. Y, and Tsai, M. D. (2012) Intermolecular binding between TIFA-FHA and TIFA-pT mediates tumor necrosis factor alpha stimulation and NF-kappaB activation. *Mol Cell Biol* 32, 2664-2673
21. Weng, J. H., Hsieh, Y. C., Huang, C. C., Wei, T. Y., Lim, L. H., Chen, Y H., Ho, M. R., Wang, I., Huang, K. F., Chen, C. J., and Tsai, M. D. (2015) Uncovering the Mechanism of Forkhead-Associated Domain-Mediated TIFA Oligomerization That Plays a Central Role in Immune Responses. *Biochemistry* 54, 6219-6229
22. Ea, C. K., Sun, L., Inoue, J., and Chen, Z. J. (2004) TIFA activates IkappaB kinase (IKK) by promoting oligomerization and ubiquitination of TRAF6. *Proc Natl Acad Sci USA* 101, 15318-15323
23. Gaudet, R. G., Sintsova, A., Buckwalter, C. M., Leung, N., Cochrane, A., Li, J., Cox, A. D., Moffat, J., and Gray-Owen, S. D. (2015) INNATE IMMUNITY. Cytosolic detection of the bacterial metabolite HBP activates TIFA-dependent innate immunity. *Science* 348, 1251-1255
24. Lin, T. Y., Wei, T. W., Li, S., Wang, S. C., He, M., Martin, M., Zhang, J., Shentu, T. P., Xiao, H., Kang, J., Wang, K. C., Chen, Z., Chien, S., Tsai, M. D., and Shyy, J. Y. (2016) TIFA as a crucial mediator for NLRP3 inflammasome. *Proc Natl Acad Sci USA* 113, 15078-15083
25. Mahajan, A., Yuan, C., Lee, H., Chen, E. S., Wu, P. Y., and Tsai, M. D. (2008) Structure and function of the phosphothreonine-specific FHA domain. *Sci Signal* 1, re12
26. Milivojevic, M., Dangeard, A. S., Kasper, C. A., Tschon, T., Emmenlauer, M., Pique, C., Schnupf, P., Guignot, J., and Arrieumerlou, C. (2017) ALPK1 controls TIFA/TRAF6-dependent innate immunity against heptose-1,7-bisphosphate of gram-negative bacteria. *PLoS Pathog,* 13 e1006224
27. Pan, W. A., Tsai, H. Y., Wang, S. C., Hsiao, M., Wu, P. Y., and Tsai, M. D. (2015) The RNA recognition motif of NIFK is required for rRNA maturation during cell cycle progression. *RNA Biol* 12, 255-267
28. Lin, C. R., Wei, T. Y., Tsai, H. Y., Wu, Y. T., Wu, P. Y., and Chen, S. T. (2015) Glycosylation-dependent interaction between CD69 and S100A8/S100A9 complex is required for regulatory T-cell differentiation. *FASEB J* 29, 5006-5017
29. Oke, A., Pearce, D., Wilkinson, R. W., Crafter, C., Odedra, R., Cavenagh, J., Fitzgibbon, J., Lister, A. T., Joel, S., and Bonnet, D. (2009) AZD1152 rapidly and negatively affects the growth and survival of human acute myeloid leukemia cells in vitro and in vivo. *Cancer research* 69, 4150-4158
30. Hou, H. A., Kuo, Y. Y., Liu, C. Y., Chou, W. C., Lee, M. C., Chen, C. Y., Lin, L. I., Tseng, M. H., Huang, C. F., Chiang, Y. C., Lee, F. Y., Liu, M. C., Liu, C. W., Tang, J. L., Yao, M., Huang, S. Y., Ko, B. S., Hsu, S. C., Wu, S.

J., Tsay, W., Chen, Y. C., and Tien, H. F. (2012) DNMT3A mutations in acute myeloid leukemia: stability during disease evolution and clinical implications. *Blood* 119, 559-568
31. Hou, H. A., Lin, C. C., Chou, W. C., Liu, C. Y., Chen, C. Y., Tang, J. L., Lai, Y. J., Tseng, M. H., Huang, C. F., Chiang, Y. C., Lee, F. Y., Kuo, Y. Y., Lee, M. C., Liu, M. C., Liu, C. W., Lin, L. I., Yao, M., Huang, S. Y., Ko, B. S., Hsu, S. C., Wu, S. J., Tsay, W., Chen, Y. C., and Tien, H. F. (2014) Integration of cytogenetic and molecular alterations in risk stratification of 318 patients with de novo non-M3 acute myeloid leukemia. *Leukemia* 28, 50-58
32. Hou, H. A., Chou, W. C., Lin, L. I., Tang, J. L., Tseng, M. H., Huang, C. F., Yao, M., Chen, C. Y., Tsay, W., and Tien, H. F. (2008) Expression of angiopoietins and vascular endothelial growth factors and their clinical significance in acute myeloid leukemia. *Leuk Res* 32, 904-912
33. Vidriales, M. B., Orfao, A., Lopez-Berges, M. C., Gonzalez, M., Lopez-Macedo, A., Garcia, M. A., Galende, J., and San Miguel, J. F. (1995) Light scatter characteristics of blast cells in acute myeloid leukaemia: association with morphology and immunophenotype. *J Clin Pathol* 48, 456-462
34. O'Reilly, M. S., Holmgren, L., Chen, C., and Folkman, J. (1996) Angiostatin induces and sustains dormancy of human primary tumors in mice. *Nat Med* 2, 689-692
35. Katsha, A., Soutto, M., Sehdev, V., Peng, D., Washington, M. K., Piazuelo, M. B., Tantawy, M. N., Manning, H. C., Lu, P., Shyr, Y., Ecsedy, J., Belkhiri, A., and El-Rifai, W. (2013) Aurora kinase A promotes inflammation and tumorigenesis in mice and human gastric neoplasia. *Gastroenterology* 145, 1312-1322 e1311-1318
36. Zeijlemaker, W., Gratama, J. W., and Schuurhuis, G. J. (2014) Tumor heterogeneity makes AML a "moving target" for detection of residual disease. *Cytometry B Clin Cytom* 86, 3-14
37. Goldenson, B., and Crispino, J. D. (2015) The aurora kinases in cell cycle and leukemia. *Oncogene* 34, 537-545
38. Yuan, H., Wang, Z., Zhang, H., Roth, M., Bhatia, R., and Chen, W. Y. (2012) Overcoming CML acquired resistance by specific inhibition of Aurora A kinase in the KCL-22 cell model. *Carcinogenesis* 33, 285-293
39. Van Etten, R. A. (2007) Aberrant cytokine signaling in leukemia. *Oncogene* 26, 6738-6749
40. Kornblau, S. M., McCue, D., Singh, N., Chen, W., Estrov, Z., and Coombes, K. R. (2010) Recurrent expression signatures of cytokines and chemokines are present and are independently prognostic in acute myelogenous leukemia and myelodysplasia. *Blood* 116, 4251-4261
41. McCormack, E., Bruserud, O., and Gjertsen, B. T. (2005) Animal models of acute myelogenous leukaemia-development, application and future perspectives. *Leukemia* 19, 687-706
42. Riether, C., Schurch, C. M., and Ochsenbein, A. F. (2015) Regulation of hematopoietic and leukemic stem cells by the immune system. *Cell Death Differ* 22, 187-198
43. Kagoya, Y., Yoshimi, A., Kataoka, K., Nakagawa, M., Kumano, K., Arai, S., Kobayashi, H., Saito, T., Iwakura, Y., and Kurokawa, M. (2014) Positive feedback between NF-kappaB and TNF-alpha promotes leukemia-initiating cell capacity. *J Clin Invest* 124, 528-542
44. Lin, T. Y., Wei, T. Y., Li, S., Wang, S. C., He, M., Matrin, M., Zhang, J., Shentu, T. P., Xiao, H., Kang, J., Wang, K. C., Chen, Z., Chien, S., Tsai, M. D., and Shyy, J. Y. (2016) TIFA as a crucial mediator for NLRP3 inflammasome. *Proc Natl Acad Sci USA* (under revision)
45. Zhou, M., Gu, L., Zhu, N., Woods, W. G., and Findley, H. W. (2003) Transfection of a dominant-negative mutant NF-κB inhibitor (IkBm) represses p53-dependent apoptosis in acute lymphoblastic leukemia cells: interaction of IkBm and p53. *Oncogene* 22, 8137-8144
46. Corey, S. J., Minden, M. D., Barber, D. L., Kantarjian, H., Wang, J. C., and Schimmer, A. D. (2007) Myelodysplastic syndromes: the complexity of stem-cell diseases. *Nat Rev Cancer* 7, 118-129
47. Fabre, C., Carvalho, G., Tasdemir, E., Braun, T., Ades, L., Grosjean, J., Boehrer, S., Metivier, D., Souquere, S., Pierron, G., Fenaux, P., and Kroemer, G. (2007) NF-kappaB inhibition sensitizes to starvation-induced cell death in high-risk myelodysplastic syndrome and acute myeloid leukemia. *Oncogene* 26, 4071-4083
48. Kornblau, S. M., Thall, P. F., Estrov, Z., Walterscheid, M., Patel, S., Theriault, A., Keating, M. J., Kantarjian, H., Estey, E., and Andreeff, M. (1999) The prognostic impact of BCL2 protein expression in acute myelogenous leukemia varies with cytogenetics. *Clinical cancer research: an official journal of the American Association for Cancer Research* 5, 1758-1766
49. Tu, Y., Renner, S., Xu, F., Fleishman, A., Taylor, J., Weisz, J., Vescio, R., Rettig, M., Berenson, J., Krajewski, S., Reed, J. C., and Lichtenstein, A. (1998) BCL-X expression in multiple myeloma: possible indicator of chemoresistance. *Cancer research* 58, 256-262
50. Crusz, S. M., and Balkwill, F. R. (2015) Inflammation and cancer: advances and new agents. *Nat Rev Clin Oncol*
51. Aggarwal, B. B., Gupta, S. C., and Kim, J. H. (2012) Historical perspectives on tumor necrosis factor and its superfamily: 25 years later, a golden journey. *Blood* 119, 651-665
52. Kuett, A., Rieger, C., Perathoner, D., Herold, T., Wagner, M., Sironi, S., Sotlar, K., Horny, H. P., Deniffel, C., Drolle, H., and Fiegl, M. (2015) IL-8 as mediator in the microenvironment-leukaemia network in acute myeloid leukaemia. *Sci Rep* 5, 18411
53. Dhawan, P., and Richmond, A. (2002) Role of CXCL1 in tumorigenesis of melanoma. *J Leukoc Biol* 72, 9-18
54. Lucena-Araujo, A. R., de Oliveira, F. M., Leite-Cueva, S. D., dos Santos, G. A., Falcao, R. P., and Rego, E. M. (2011) High expression of AURKA and AURKB is associated with unfavorable cytogenetic abnormalities and high white blood cell count in patients with acute myeloid leukemia. *Leuk Res* 35, 260-264
55. Seymour, J. F., Kim, D. W., Rubin, E., Haregewoin, A., Clark, J., Watson, P., Hughes, T., Dufva, I., Jimenez, J. L., Mahon, F. X., Rousselot, P., Cortes, J., Martinelli, G., Papayannidis, C., Nagler, A., and Giles, F. J. (2014) A phase 2 study of MK-0457 in patients with BCR-ABL T315I mutant chronic myelogenous leukemia and philadelphia chromosome-positive acute lymphoblastic leukemia. *Blood Cancer J* 4, e238
56. Giles, F. J., Swords, R. T., Nagler, A., Hochhaus, A., Ottmann, O. G., Rizzieri, D. A., Talpaz, M., Clark, J., Watson, P., Xiao, A., Zhao, B., Bergstrom, D., Le Coutre, P. D., Freedman, S. J., and Cortes, J. E. (2013) MK-0457, an Aurora kinase and BCR-ABL inhibitor, is active in patients with BCR-ABL T315I leukemia. *Leukemia* 27, 113-117
57. Okabe, S., Tauchi, T., and Ohyashiki, K. (2010) Efficacy of MK-0457 and in combination with vorinostat against Philadelphia chromosome positive acute lymphoblastic leukemia cells. *Ann Hematol* 89, 1081-1087
58. Vader, G., and Lens, S. M. (2008) The Aurora kinase family in cell division and cancer. *Biochimica et biophysica acta* 1786, 60-72

What is claimed is:

1. A TIFA inhibitor, which is an isolated TIFA peptide fragment comprising a dimerization-core peptide segment in combination with a Thr9 peptide segment in the N-terminal or in combination with a TRAF6/TRAF2 interacting peptide segment in the C-terminal, wherein
  (i) the Thr9 peptide segment comprises a N-terminal phosphorylation/oligomerization motif of $MX_1X_2FEDX_3DTX_4EX_5X_6T$ as set forth in SEQ ID NO: 13, wherein $X_1$ is serine (S) or threonine (T), $X_2$ is serine (S), threonine (T), asparagine (N), $X_3$ is alanine (A) or valine (V), $X_4$ is glutamate (E) or glutamine (Q), $X_5$ is threonine (T) or methionine (M), and $X_6$ is valine (V) or leucine (L);
  (ii) the dimerization-core peptide segment comprises six β strands, which includes
    (a) a β3 strand having a β3 motif of VKFG;
    (b) a β4 strand having a β4 motif of $YX_1F$, wherein $X_1$ is threonine (T) or isoleucine (I);
    (c) a β5 strand having a β5 motif of $QFX_1LX_2X_3F$, wherein $X_1$ is serine (S), valine (V) or alanine (A), $X_2$ is glutamine (Q) or histidine (H), and $X_3$ is leucine (L), proline (P) or valine (V);
    (d) a β6 strand having a β6 motif of SFEIKN;
    (e) a β7 strand having a β7 motif of LIV; and
    (f) a β8 strand having a β8 motif of $X_1X_2L$, wherein $X_1$ is arginine (R), glutamine (Q) or lysine (K), and $X_2$ is glutamate (E) or threonine (T);
    wherein each of the β3 to β8 strands is connected to the next in sequence from N-terminal to C-terminal by a plurality of internal loop sequences; and
  (iii) the TRAF6/TRAF2 interacting peptide segment comprises four β strands, which includes (a) a β9 strand having a β9 motif of LX$_1$KX$_2$D, wherein X$_1$ is Asparagine (N) or histidine (H), and X$_2$ is methionine (M), leucine (L), valine (V) or isoleucine (I);

(b) a β10 strand having a β10 motif of X$_1$CX$_2$ X$_3$RF, wherein X$_1$ is arginine (R) or lysine (K), X$_2$ is methionine (M) or leucine (L), and X$_3$ is valine (V), leucine (L) or ioleucine (I);

(c) a β11 strand having a β11 motif of YQX$_1$LX$_2$ X$_3$ X$_4$E, wherein X$_1$ is phenylalanine (F) or isoleucine (I), X$_2$ is methionine (M), leucine (L), valine (V) or isoleucine (I), X$_3$ is glutamate (E) or glutamine (Q), and X$_4$ is lysine (K) or arginine (R); and (d) a β12 strand having a β12 motif of X$_1$FX$_2$X$_3$X$_4$ FX$_5$X$_6$, wherein X$_1$ is phenylananine (F) or serine (S), X$_2$ is glutamate (E) or glutamine (Q), X$_3$ is threonine (T) or isoleucine (I), X$_4$ is glutamine (Q), histidine (H) or glutamate (E), X$_5$ is isoleucine (I), valine (V), serine (S) or phenylalanine (F), and X$_6$ is leucine (L), methionine (M) or phenylananine (F);

wherein each of the β9 to β12 strands is connected to the next in sequence from N-terminal to C-terminal by a plurality of internal loop sequences; and a C-terminal loop sequence connected to the C-terminal of β12 strand;

wherein the isolated TIFA peptide fragment does not contain both of the Thr9 peptide segment and the TRAF6/TRAF2 interacting peptide segment.

2. The TIFA inhibitor of claim 1, wherein
the N-terminal Thr9-phorsphorylation motif is located at positions corresponding to positions 1-14 of SEQ ID NO: 1;
the β3 motif is located at positions corresponding to positions 47-50 of SEQ ID NO: 1;
the β4 motif is located at positions corresponding to positions 58-60 of SEQ ID NO: 1;
the β5 motif is located at positions corresponding to positions 69-75 of SEQ ID NO: 1;
the β6 motif is located at positions corresponding to positions 84-89 of SEQ ID NO: 1;
the β7 motif is located at positions corresponding to positions 96-98 of SEQ ID NO: 1;
the β8 motif is located at positions corresponding to positions 101-103 of SEQ ID NO: 1;
the β9 motif is located at positions corresponding to positions 106-110 of SEQ ID NO: 1;
the β10 motif is located at positions corresponding to positions 114-119 of SEQ ID NO: 1;
the β11 motif is located at positions corresponding to positions 122-129 of SEQ ID NO: 1;
the β12 motif is located at positions corresponding to positions 136-143 of SEQ ID NO: 1; and/or
the C-terminal loop sequence is located at positions corresponding to positions 144-184 of SEQ ID NO: 1.

3. The TIFA inhibitor of claim 1, wherein the Thr9 peptide segment further comprises two β strands, which includes (a) a β1 strand having a β1 motif of X$_1$LX$_2$X$_3$T X$_4$ Y, wherein X$_1$ is cysteine (C) or serine (S), X$_2$ is glutamine (Q) or histidine (H), X$_3$ is methionine (M), isoleucine (I), leucine (L) or valine (V), and X$_4$ is valine (V), isoleucine (I) or leucine (L), and (b) a β2 strand having a β2 motif of at positions X$_1$X$_2$X$_3$P, wherein X$_1$ is glutamate (E) or aspirate (D), X$_2$ is lysine (K) or threonine (T), and X$_3$ is leucine (L) or phenylalanine (F), wherein the β1 strand is connected to the β2 strand in sequence from N-terminal to C-terminal by an internal loop sequence.

4. The TIFA inhibitor of claim 3, wherein
the β1 motif is located at positions corresponding to positions 15-21 of SEQ ID NO: 1; and/or
the β2 motif is located at positions corresponding to positions 39-42 of SEQ ID NO: 1.

5. The TIFA inhibitor of claim 1, wherein
the Thr9 peptide segment comprises an amino acid sequence corresponding to positions 1-45 of SEQ ID NO: 1 or an amino acid sequence having at least 70% identity to said sequence;
the dimerization-core peptide segment comprises an amino acid sequence corresponding to positions 46-103 of SEQ ID NO: 1 or an amino acid sequence having at least 70% identity to said sequence; and/or
the TRAF6/TRAF2 interacting peptide segment comprises an amino acid sequence corresponding to positions 104-184 of SEQ ID NO: 1 or an amino acid sequence having at least 70% identity to said sequence.

6. The TIFA inhibitor of claim 1, wherein
the Thr9 peptide segment comprises an amino acid sequence selected from the group consisting of SEQ ID NOs: 23-34;
the dimerization-core peptide segment comprises an amino acid sequence selected from the group consisting of SEQ ID NOs: 35-46; and/or
the TRAF6/TRAF2 interacting peptide segment comprises an amino acid sequence selected from the group consisting of SEQ ID NOs: 47-58.

7. The TIFA inhibitor of claim 1, which is a F1-F2 peptide fragment comprising the Thr9 peptide segment and the dimerization-core peptide segment, wherein the C-terminus of the Thr9 peptide segment is linked to the N-terminal of the dimerization-core peptide segment.

8. The TIFA inhibitor of claim 7, which comprises an amino acid sequence selected from the group consisting of SEQ ID NO:71-82.

9. The TIFA inhibitor of claim 1, which is a F2-F3 peptide fragment comprising the dimerization-core peptide segment and the TRAF 6 interacting peptide segment, wherein the C-terminus of the dimerization-core peptide segment is linked to the N-terminal of the TRAF 6 interacting peptide segment.

10. The TIFA inhibitor of claim 9, which comprises an amino acid sequence selected from the group consisting of SEQ ID NO: 83-94.

11. A recombinant nucleic acid comprising a nucleotide sequence encoding a TIFA peptide fragment of claim 1.

12. The recombinant nucleic acid of claim 11, which is a vector, particularly a viral vector.

13. A composition comprising a TIFA peptide fragment of claim 1 and a physiologically acceptable carrier.

14. A method for treating a disease or condition associated with TIFA activation in a subject in need thereof, comprising administering to the subject an effective amount of a TIFA peptide fragment of claim 1, an encoding nucleic acid thereof or a composition comprising the peptide or the encoding nucleic acid.

15. The method of claim 14, wherein the disease or condition is a cancer or an inflammatory disorder associated with TIFA activation, or a cancer or an inflammatory disorder associated with cytokine-stimulated NF-κB activation.

16. The method of claim 14, wherein the disease or condition is a cancer selected from the group consisting of leukemia, liver cancer, stomach cancer.

17. The method of claim 14, wherein the disease or condition is an inflammatory disease selected from the group consisting of hepatitis, atherosclerosis, atherosclerosis, pulmonary arterial hypertension, cardiomyopathy, rheumatoid arthritis, inflammatory bowel disease and Fabry disease.

18. The method of claim 14, wherein the subject is afflicted with cancer, and the peptide fragment, the encoding nucleic acid and the composition comprising the peptide or the encoding nucleic acid is administered to the subject in combination with an anti-cancer treatment.

19. The method of claim 18, wherein the anti-cancer treatment comprises administration of an anti-cancer agent selected from the group consisting of etoposide, idarubicin, cytarabine, sorafenib, regorafenib, bleomycin, bortezomib, busulfan, and obatoclax, or irradiation.

20. The method of claim 19, wherein the peptide fragment, the encoding nucleic acid or the composition is administered in an amount effective in enhancing cytotoxocity of the anti-cancer treatment.

21. A method for inhibiting cytokine-stimulated NF-κB activation in a subject, comprising administering to the subject an effective amount of a TIFA antagonist.

22. The method of claim 21, wherein the TIFA antagonist is an interfering nucleic acid targeting TIFA or a TIFA dominant negative inhibitor.

23. A method for inhibiting cytokine-stimulated NF-κB activation in a subject, comprising administering to the subject an effective amount of a TIFA dominant negative inhibitor, wherein the TIFA dominant negative inhibitor is the TIFA inhibitor of claim 1.

24. The method of claim 21, wherein the subject is a patient having a disease or condition associated with cytokine-stimulated NF-κB activation.

25. The method of claim 21, wherein the subject is a patient afflicted with an inflammatory disease selected from the group consisting of hepatitis, atherosclerosis, atherosclerosis, pulmonary arterial hypertension, cardiomyopathy, rheumatoid arthritis, inflammatory bowel disease and Fabry disease.

26. The method of claim 21, wherein the subject is a patient afflicted with a cancer.

27. The method of claim 26, wherein the TIFA antagonist is administrated with an anti-cancer treatment to the patient.

28. The method of claim 27, wherein the TIFA antagonist is administrated in an amount effective in increasing cytotoxicity of the anti-cancer treatment to cancer cells as compared with the anti-cancer treatment without the TIFA antagonist.

29. The method of claim 28, wherein the cancer cells are selected from the group consisting of lung cancer cells, liver cancer cells, leukemia cells, breast cancer cells, testicular embryonic carcinoma cells and osteosarcoma cells.

30. The method of claim 27, wherein the patient exhibits resistance to the anti-cancer treatment.

* * * * *

SEQUENCE LISTING

<160> NUMBER OF SEQ ID NOS: 95

<210> SEQ ID NO 1
<211> LENGTH: 184
<212> TYPE: PRT
<213> ORGANISM: Homo sapiens

<400> SEQUENCE: 1

```
Met Thr Ser Phe Glu Asp Ala Asp Thr Glu Glu Thr Val Thr Cys Leu
1               5                   10                  15

Gln Met Thr Val Tyr His Pro Gly Gln Leu Gln Cys Gly Ile Phe Gln
            20                  25                  30

Ser Ile Ser Phe Asn Arg Glu Lys Leu Pro Ser Ser Glu Val Val Lys
        35                  40                  45

Phe Gly Arg Asn Ser Asn Ile Cys His Tyr Thr Phe Gln Asp Lys Gln
    50                  55                  60

Val Ser Arg Val Gln Phe Ser Leu Gln Leu Phe Lys Lys Phe Asn Ser
65                  70                  75                  80

Ser Val Leu Ser Phe Glu Ile Lys Asn Met Ser Lys Lys Thr Asn Leu
                85                  90                  95

Ile Val Asp Ser Arg Glu Leu Gly Tyr Leu Asn Lys Met Asp Leu Pro
            100                 105                 110

Tyr Arg Cys Met Val Arg Phe Gly Glu Tyr Gln Phe Leu Met Glu Lys
        115                 120                 125

Glu Asp Gly Glu Ser Leu Glu Phe Phe Glu Thr Gln Phe Ile Leu Ser
    130                 135                 140

Pro Arg Ser Leu Leu Gln Glu Asn Asn Trp Pro His Arg Pro Ile
145                 150                 155                 160

Pro Glu Tyr Gly Thr Tyr Ser Leu Cys Ser Ser Gln Ser Ser Ser Pro
                165                 170                 175

Thr Glu Met Asp Glu Asn Glu Ser
            180
```

<210> SEQ ID NO 2
<211> LENGTH: 185
<212> TYPE: PRT
<213> ORGANISM: Oryctolagus cuniculus

<400> SEQUENCE: 2

```
Met Ser Ser Phe Glu Asp Ala Asp Thr Glu Glu Thr Val Thr Cys Leu
1               5                   10                  15

Gln Met Thr Val Tyr His Pro Ala Gln Phe Gln Ser Gly Ile Phe Gln
            20                  25                  30

Ala Ile Asp Phe Asn Lys Arg Asp Lys Leu Pro Ser Ser Glu Val Val
        35                  40                  45

Lys Phe Gly Arg Asn Ser Lys Val Cys His Tyr Thr Phe Gln Asp Lys
    50                  55                  60

Gln Ala Ser Arg Val Gln Phe Ser Leu Gln Leu Phe Lys Gln Phe Asn
65                  70                  75                  80

Ser Ser Val Leu Ser Phe Glu Ile Lys Asn Met Ser Arg Lys Thr Ser
                85                  90                  95

Leu Ile Val Asp Ser Gln Glu Leu Gly Tyr Leu Asn Lys Leu Asp Leu
            100                 105                 110

Pro Tyr Lys Cys Met Val Arg Phe Ser Glu Tyr Gln Phe Leu Met Glu
        115                 120                 125

Lys Glu Asp Gly Glu Ala Leu Asp Ser Phe Glu Thr Gln Phe Ile Leu
```

```
              130                 135                 140
Ser Pro Arg Pro Leu Leu Gln Glu Asn Ile Trp Pro His Lys Pro
145                 150                 155                 160

Ile Pro Glu Tyr Gly Ile Tyr Ser Ser Cys Ser Ala Gln Ser Thr Ser
                165                 170                 175

Pro Thr Glu Met Asp Glu Asp Glu Leu
            180                 185
```

<210> SEQ ID NO 3
<211> LENGTH: 186
<212> TYPE: PRT
<213> ORGANISM: Canis lupus familiaris

<400> SEQUENCE: 3

```
Met Met Ser Asn Phe Glu Asp Ala Asp Thr Glu Glu Thr Val Thr Cys
1               5                   10                  15

Leu Gln Ile Thr Val Tyr His Pro Gly Gln Leu Gln Asn Gly Ile Phe
                20                  25                  30

Gln Ser Ile Arg Phe Tyr Asn Arg Glu Lys Leu Pro Ser Ser Glu Val
            35                  40                  45

Val Lys Phe Gly Arg Asn Ser Asn Ile Cys Arg Tyr Thr Phe Gln Asp
50                  55                  60

Lys Gln Val Ser Arg Val Gln Phe Ser Leu Gln Leu Phe Lys Lys Phe
65                  70                  75                  80

Asp Ser Ser Val Leu Ser Phe Glu Ile Lys Asn Met Ser Lys Lys Thr
                85                  90                  95

Asn Leu Leu Val Asp Asn Lys Glu Leu Cys Tyr Leu Asn Lys Ile Asp
                100                 105                 110

Leu Pro Tyr Lys Cys Met Val Arg Phe Gly Glu Tyr Gln Phe Leu Ile
            115                 120                 125

Glu Lys Glu Asp Gly Glu Ser Leu Glu Phe Phe Glu Thr Gln Phe Ile
130                 135                 140

Leu Ser Pro Arg Ser Leu Leu Gln Glu Asn Asn Trp Pro Ile Gln Lys
145                 150                 155                 160

Pro Ile Pro Glu Tyr Gly Ser Tyr Ser Ser Cys Phe Thr Gln Asn Thr
                165                 170                 175

Ser Pro Thr Glu Met Asp Glu Asn Glu Leu
                180                 185
```

<210> SEQ ID NO 4
<211> LENGTH: 184
<212> TYPE: PRT
<213> ORGANISM: Mus musculus

<400> SEQUENCE: 4

```
Met Ser Thr Phe Glu Asp Ala Asp Thr Glu Glu Thr Val Thr Cys Leu
1               5                   10                  15

Gln Met Thr Ile Tyr His Pro Gly Gln Gln Ser Gly Ile Phe Lys Ser
                20                  25                  30

Ile Arg Phe Cys Ser Lys Glu Lys Phe Pro Ser Ile Glu Val Val Lys
            35                  40                  45

Phe Gly Arg Asn Ser Asn Met Cys Gln Tyr Thr Phe Gln Asp Lys Gln
50                  55                  60

Val Ser Arg Ile Gln Phe Val Leu Gln Pro Phe Lys Gln Phe Asn Ser
65                  70                  75                  80

Ser Val Leu Ser Phe Glu Ile Lys Asn Met Ser Lys Lys Thr Ser Leu
```

```
                        85                  90                  95
Met Val Asp Asn Gln Glu Leu Gly Tyr Leu Asn Lys Met Asp Leu Pro
                100                 105                 110

Tyr Lys Cys Met Leu Arg Phe Gly Glu Tyr Gln Phe Leu Leu Gln Lys
            115                 120                 125

Glu Asp Gly Glu Ser Val Glu Ser Phe Glu Thr Gln Phe Ile Met Ser
        130                 135                 140

Ser Arg Pro Leu Leu Gln Glu Asn Asn Trp Pro Thr Gln Asn Pro Ile
145                 150                 155                 160

Pro Glu Asp Gly Met Tyr Ser Ser Tyr Phe Thr His Arg Ser Ser Pro
                165                 170                 175

Ser Glu Met Asp Glu Asn Glu Leu
            180

<210> SEQ ID NO 5
<211> LENGTH: 185
<212> TYPE: PRT
<213> ORGANISM: Rattus norvegicus

<400> SEQUENCE: 5

Met Ser Thr Phe Glu Asp Ala Asp Thr Glu Glu Thr Val Thr Cys Leu
1               5                   10                  15

Gln Met Thr Ile Tyr His Pro Gly Gln Leu Gln Ser Gly Ile Phe Lys
            20                  25                  30

Ser Ile Arg Phe Cys Ser Lys Glu Lys Phe Pro Ser Ile Glu Val Val
        35                  40                  45

Lys Phe Gly Arg Asn Ser Asn Met Cys Gln Tyr Thr Phe Gln Asp Lys
    50                  55                  60

Gln Val Ser Arg Val Gln Phe Ala Leu Gln Pro Phe Lys Gln Phe Asn
65                  70                  75                  80

Ser Ser Val Leu Ser Phe Glu Ile Lys Asn Met Ser Lys Lys Thr Ser
                85                  90                  95

Leu Met Val Asp Asn Gln Glu Leu Gly Tyr Leu Asn Lys Met Asp Leu
                100                 105                 110

Pro Tyr Lys Cys Met Leu Arg Phe Gly Glu Tyr Gln Phe Leu Leu Gln
            115                 120                 125

Lys Glu Asp Gly Glu Ser Val Glu Ser Phe Glu Thr Gln Phe Ile Leu
        130                 135                 140

Ser Pro Arg Pro Leu Leu Gln Glu Asn Asn Trp Pro Thr Gln Ser Pro
145                 150                 155                 160

Ile Pro Glu Asp Gly Val Tyr Ser Ser Tyr Phe Thr His Arg Ser Ser
                165                 170                 175

Pro Ala Glu Met Asp Glu Asn Glu Leu
            180                 185

<210> SEQ ID NO 6
<211> LENGTH: 185
<212> TYPE: PRT
<213> ORGANISM: Cricetulus griseus

<400> SEQUENCE: 6

Met Ser Ser Phe Glu Asp Ala Asp Thr Glu Glu Thr Val Thr Cys Leu
1               5                   10                  15

Gln Leu Thr Val Tyr His Pro Gly Gln Leu Gln Ser Gly Ile Phe Lys
            20                  25                  30

Ser Ile Arg Phe Cys Asn Lys Glu Lys Phe Pro Ser Ile Glu Glu Val
```

```
                    35                  40                  45

Lys Phe Gly Arg Asn Ser Asn Ile Cys Arg Tyr Thr Phe Gln Asp Lys
 50                      55                  60

Gln Val Ser Arg Val Gln Phe Ala Leu Gln Pro Phe Lys Gln Phe Asn
 65                  70                  75                  80

Ser Ser Val Leu Ser Phe Glu Ile Lys Asn Met Ser Lys Lys Thr Ser
                 85                  90                  95

Leu Met Val Asp Asn Gln Glu Leu Gly Tyr Leu Asn Lys Met Asp Leu
                100                 105                 110

Pro Tyr Lys Cys Leu Leu Arg Phe Gly Glu Tyr Gln Phe Leu Leu Glu
            115                 120                 125

Lys Glu Asp Gly Glu Ser Val Glu Ser Phe Glu Thr Gln Phe Ile Leu
130                 135                 140

Ser Pro Arg Pro Leu Leu Gln Glu Asn Asn Trp Pro Thr Gln Ser Pro
145                 150                 155                 160

Ile Pro Glu Asp Gly Gly Tyr Ser Ser Tyr Phe Thr His Arg Thr Ser
                165                 170                 175

Pro Thr Glu Met Asp Glu Asn Glu Leu
            180                 185

<210> SEQ ID NO 7
<211> LENGTH: 185
<212> TYPE: PRT
<213> ORGANISM: Castor canadensis

<400> SEQUENCE: 7

Met Ser Asn Phe Glu Asp Ala Asp Thr Glu Thr Leu Thr Cys Leu
 1               5                  10                  15

His Val Thr Val Tyr His Ser Gly Lys Ser His Asn Gly Val Phe Gln
                 20                  25                  30

Ser Ile Glu Phe Tyr Asn Arg Glu Lys Leu Pro Ser Gly Glu Val Val
             35                  40                  45

Lys Phe Gly Arg Asn Ser Ser Ile Cys Arg Tyr Thr Phe Gln Asp Lys
 50                      55                  60

Gln Val Ser Arg Val Gln Phe Ser Leu Gln Pro Phe Lys Gln Phe Asn
 65                  70                  75                  80

Ser Ser Val Leu Ser Phe Glu Ile Lys Asn Met Ser Lys Lys Thr Ser
                 85                  90                  95

Leu Ile Val Asp Ser Gln Glu Leu Gly Tyr Leu Asn Lys Met Asp Leu
                100                 105                 110

Pro Tyr Arg Cys Met Val Arg Phe Gly Glu Tyr Gln Phe Leu Leu Glu
            115                 120                 125

Lys Glu Asp Gly Glu Ser Leu Glu Ser Phe Gln Thr His Phe Ile Leu
130                 135                 140

Ser Pro Arg Pro Leu Leu Gln Glu Asn Asn Trp Pro Ala Gln Thr Pro
145                 150                 155                 160

Ile Pro Glu Asp Gly Gly Tyr Ser Ser Tyr Leu Thr Pro Ser Thr Phe
                165                 170                 175

Pro Thr Glu Ile Asp Glu Asn Glu Leu
            180                 185

<210> SEQ ID NO 8
<211> LENGTH: 185
<212> TYPE: PRT
<213> ORGANISM: CAVIA PORCELLUS
```

-continued

<400> SEQUENCE: 8

```
Met Ser Ser Phe Glu Asp Ala Asp Thr Gln Glu Thr Val Thr Cys Leu
1               5                   10                  15

Gln Met Thr Val Tyr His Pro Gly His Val Gln Arg Gly Ile Phe Arg
                20                  25                  30

Ser Ile Asn Phe Ser Lys Arg Glu Lys Leu Pro Ser Ser Glu Val Val
                35                  40                  45

Lys Phe Gly Arg Asn Ser Ser Cys His Tyr Ile Phe Gln Asp Lys
            50                  55                  60

Gln Ala Ser Arg Val Gln Phe Ser Leu His Pro Phe Lys Pro Phe Asn
65                  70                  75                  80

Ser Ser Val Leu Ser Phe Glu Ile Lys Asn Leu Ser Lys Lys Thr Ser
                85                  90                  95

Leu Ile Val Asp Ser Arg Glu Leu Arg Tyr Leu Asn Lys Met Asp Leu
                100                 105                 110

Pro Tyr Arg Cys Met Val Arg Phe Gly Glu Tyr Gln Phe Leu Leu Glu
            115                 120                 125

Arg Glu Asp Gly Glu Ser Leu Glu Ser Phe Glu Thr Gln Phe Val Phe
130                 135                 140

Ser Pro Arg Pro Leu Leu Gln Glu Asn Ser Trp Pro Thr Gln Ser Pro
145                 150                 155                 160

Ile Pro Glu Asp Gly Ser Phe Ser Gly Tyr Thr Arg Ser Ser Phe
                165                 170                 175

Pro Met Glu Met Asp Glu Asn Glu Trp
            180                 185
```

<210> SEQ ID NO 9
<211> LENGTH: 185
<212> TYPE: PRT
<213> ORGANISM: Bos taurus

<400> SEQUENCE: 9

```
Met Ser Ser Phe Glu Asp Ala Asp Thr Glu Glu Met Val Thr Cys Leu
1               5                   10                  15

Gln Met Thr Leu Tyr His Pro Gly His Gln Arg Ser Gly Ile Phe Arg
                20                  25                  30

Ser Ile Lys Phe Phe Asn Arg Glu Lys Leu Pro Thr Ser Glu Val Val
                35                  40                  45

Lys Phe Gly Arg Asn Ser His Thr Cys Asn Tyr Ile Phe Gln Asp Lys
            50                  55                  60

Gln Val Ser Arg Val Gln Phe Ser Leu Gln Val Phe Lys Lys Phe Asn
65                  70                  75                  80

Ser Ser Val Val Ser Phe Glu Ile Lys Asn Met Ser Lys Lys Thr Ser
                85                  90                  95

Leu Leu Val Asp Asn Lys Glu Leu Gly Tyr Leu Asn Lys Met Asp Leu
                100                 105                 110

Pro Asp Lys Cys Met Ile Arg Phe Gly Asp Tyr Gln Phe Leu Val Glu
            115                 120                 125

Lys Glu Asp Gly Glu Ser Leu Glu Phe Phe Glu Ile Gln Phe Ser Leu
130                 135                 140

Ser Lys Lys Pro Leu Leu Gln Glu Asn Asn Trp Leu Ser Gln Glu Pro
145                 150                 155                 160

Ile Pro Glu Cys Gly Ser Tyr Ser Cys Leu Thr Gln Asn Asn Ser
                165                 170                 175
```

Pro Met Glu Val Gly Glu Asn Glu Trp
            180                 185

<210> SEQ ID NO 10
<211> LENGTH: 185
<212> TYPE: PRT
<213> ORGANISM: Capra hircus

<400> SEQUENCE: 10

Met Ser Ser Phe Glu Asp Val Asp Thr Glu Thr Val Thr Ser Leu
1               5                   10                  15

His Met Thr Leu Tyr His Pro Gly His Gln Arg Ser Gly Ile Phe Gln
            20                  25                  30

Ser Ile Lys Phe Cys Asn Arg Glu Thr Leu Pro Thr Ser Glu Val Val
            35                  40                  45

Lys Phe Gly Arg Asn Ser Thr Cys Arg Tyr Thr Phe Gln Asp Lys
50                  55                  60

Gln Val Ser Arg Val Gln Phe Ser Leu Gln Leu Phe Lys Lys Phe Asp
65                  70                  75                  80

Ser Ser Val Val Ser Phe Glu Ile Lys Asn Met Ser Lys Lys Thr Asn
                85                  90                  95

Leu Leu Val Asp Asp Lys Glu Leu Ser Tyr Leu Asn Lys Met Asp Leu
            100                 105                 110

Pro Asp Lys Cys Leu Ile Arg Phe Gly Asp Tyr Gln Phe Leu Val Glu
            115                 120                 125

Lys Glu Asp Gly Glu Ser Leu Glu Phe Phe Glu Ile Gln Phe Phe Leu
130                 135                 140

Ser Ile Arg Pro Leu Leu Gln Glu Asn Lys Trp Leu Pro Gln Lys Pro
145                 150                 155                 160

Thr Pro Glu Cys Gly Ser Cys Ser Pro Cys Ser Thr Gln Asn Asn Ser
                165                 170                 175

Pro Met Glu Ala Gly Glu Asn Glu Trp
            180                 185

<210> SEQ ID NO 11
<211> LENGTH: 184
<212> TYPE: PRT
<213> ORGANISM: Sus scrofa

<400> SEQUENCE: 11

Met Ser Ser Phe Glu Asp Ala Asp Thr Glu Thr Leu Thr Cys Leu
1               5                   10                  15

Gln Met Thr Val Tyr His Pro Gly His Gln Gln Asn Gly Ile Phe Gln
            20                  25                  30

Ser Arg Arg Phe Phe Ser Arg Glu Lys Leu Pro Ser Ser Glu Val Val
            35                  40                  45

Lys Phe Gly Arg Asn Ser Ile Cys Gln Tyr Thr Phe Gln Asp Lys His
50                  55                  60

Ala Ser Arg Val Gln Phe Ser Leu His Leu Phe Lys Lys Phe Asp Ser
65                  70                  75                  80

Ser Val Leu Ser Phe Glu Ile Lys Asn Met Ser Lys Lys Thr Ser Leu
                85                  90                  95

Ile Val Asp Asn Gln Glu Leu Gly Tyr Leu Asn Lys Met Asp Leu Pro
            100                 105                 110

Pro Lys Cys Met Val Arg Phe Gly Asp Tyr Gln Phe Leu Ile Glu Lys
            115                 120                 125

```
Glu Asp Gly Glu Ser Leu Glu Phe Phe Glu Ile Gln Phe Ile Leu Ser
            130                 135                 140

Thr Arg Ser Leu Leu Gln Glu Asn Asn Trp Leu Pro Gln Lys Pro Ile
145                 150                 155                 160

Pro Glu Cys Gly Asn Tyr Leu Ser Cys Ser Thr Gln Gly Asn Ser Pro
                165                 170                 175

Ile Glu Met Gly Glu Asn Glu Trp
            180
```

```
<210> SEQ ID NO 12
<211> LENGTH: 185
<212> TYPE: PRT
<213> ORGANISM: Equus caballus

<400> SEQUENCE: 12
```

```
Met Ser Ser Phe Glu Asp Ala Asp Thr Glu Thr Leu Thr Cys Leu
1               5                   10                  15

Gln Met Thr Val Tyr His Pro Gly Gln Pro Asn Gly Ile Phe Gln
            20                  25                  30

Ser Ile Gly Phe His Lys Arg Glu Lys Leu Pro Ser Arg Glu Glu Val
            35                  40                  45

Lys Phe Gly Arg Ser Ser Lys Val Cys Asn Tyr Thr Phe Gln Asp Arg
50                  55                  60

Gln Val Ser Arg Val Gln Phe Ser Leu Gln Leu Phe Lys Lys Phe Asp
65                  70                  75                  80

Ser Ser Val Leu Ser Phe Glu Ile Lys Asn Met Ser Lys Arg Thr Ser
                85                  90                  95

Leu Ile Val Asp Asn Arg Thr Leu Asp Phe Leu His Lys Val Asp Leu
                100                 105                 110

Pro Asp Arg Cys Met Ile Arg Phe Gly Asp Tyr Gln Ile Leu Met Glu
            115                 120                 125

Lys Glu Asp Gly Val Ser Leu Glu Phe Phe Glu Thr Glu Phe Ile Leu
            130                 135                 140

Ser Pro Arg Ser Leu Leu Gln Lys Asn Tyr Trp Pro Pro Gln Asn Pro
145                 150                 155                 160

Ile Pro Glu Tyr Cys His Ser Val Trp Ser Ser Gln Ser Thr Ser
                165                 170                 175

Pro Met Glu Thr Asp Glu Asn Glu Leu
            180                 185
```

```
<210> SEQ ID NO 13
<211> LENGTH: 14
<212> TYPE: PRT
<213> ORGANISM: artificial sequence
<220> FEATURE:
<223> OTHER INFORMATION: N-terminal phosphorylation/oligomerization
      motif (1-14aa)
<220> FEATURE:
<221> NAME/KEY: MISC_FEATURE
<222> LOCATION: (2)..(2)
<223> OTHER INFORMATION: Xaa can be serine (S) or threonine (T)
<220> FEATURE:
<221> NAME/KEY: MISC_FEATURE
<222> LOCATION: (3)..(3)
<223> OTHER INFORMATION: Xaa is serine (S), threonine (T) or asparagine
      (N).
<220> FEATURE:
<221> NAME/KEY: MISC_FEATURE
<222> LOCATION: (7)..(7)
<223> OTHER INFORMATION: Xaa can be alanine (A) or valine (V).
<220> FEATURE:
<221> NAME/KEY: MISC_FEATURE
```

```
<222> LOCATION: (10)..(10)
<223> OTHER INFORMATION: Xaa can be glutamate (E) or glutamine (Q).
<220> FEATURE:
<221> NAME/KEY: MISC_FEATURE
<222> LOCATION: (12)..(12)
<223> OTHER INFORMATION: Xaa can be threonine (T) or methionine (M).
<220> FEATURE:
<221> NAME/KEY: MISC_FEATURE
<222> LOCATION: (13)..(13)
<223> OTHER INFORMATION: Xaa can be valine (V) or leucine (L).

<400> SEQUENCE: 13

Met Xaa Xaa Phe Glu Asp Xaa Asp Thr Xaa Glu Xaa Xaa Thr
1               5                   10

<210> SEQ ID NO 14
<211> LENGTH: 7
<212> TYPE: PRT
<213> ORGANISM: artificial sequence
<220> FEATURE:
<223> OTHER INFORMATION: b1 motif
<220> FEATURE:
<221> NAME/KEY: MISC_FEATURE
<222> LOCATION: (1)..(1)
<223> OTHER INFORMATION: Xaa can be cysteine (C) or serine (S).
<220> FEATURE:
<221> NAME/KEY: MISC_FEATURE
<222> LOCATION: (3)..(3)
<223> OTHER INFORMATION: Xaa can be glutamine (Q) or histidine (H).
<220> FEATURE:
<221> NAME/KEY: MISC_FEATURE
<222> LOCATION: (4)..(4)
<223> OTHER INFORMATION: Xaa can bemethionine (M), isoleucine (I),
      leucine (L) or valine (V).
<220> FEATURE:
<221> NAME/KEY: MISC_FEATURE
<222> LOCATION: (6)..(6)
<223> OTHER INFORMATION: Xaa can be valine (V), isoleucine (I) or
      leucine (L).

<400> SEQUENCE: 14

Xaa Leu Xaa Xaa Thr Xaa Tyr
1               5

<210> SEQ ID NO 15
<211> LENGTH: 4
<212> TYPE: PRT
<213> ORGANISM: artificial sequence
<220> FEATURE:
<223> OTHER INFORMATION: b2 motif
<220> FEATURE:
<221> NAME/KEY: MISC_FEATURE
<222> LOCATION: (1)..(1)
<223> OTHER INFORMATION: Xaa can be glutamate (E) or aspirate (D).
<220> FEATURE:
<221> NAME/KEY: MISC_FEATURE
<222> LOCATION: (2)..(2)
<223> OTHER INFORMATION: Xaa can be lysine (K) or threonine (T).
<220> FEATURE:
<221> NAME/KEY: MISC_FEATURE
<222> LOCATION: (3)..(3)
<223> OTHER INFORMATION: Xaa can be leucine (L) or phenylalanine (F).

<400> SEQUENCE: 15

Xaa Xaa Xaa Pro
1

<210> SEQ ID NO 16
<211> LENGTH: 4
<212> TYPE: PRT
<213> ORGANISM: artificial sequence
<220> FEATURE:
<223> OTHER INFORMATION: b3 motif
```

```
<400> SEQUENCE: 16

Val Lys Phe Gly
1

<210> SEQ ID NO 17
<211> LENGTH: 7
<212> TYPE: PRT
<213> ORGANISM: artificial sequence
<220> FEATURE:
<223> OTHER INFORMATION: b5 motif
<220> FEATURE:
<221> NAME/KEY: MISC_FEATURE
<222> LOCATION: (3)..(3)
<223> OTHER INFORMATION: Xaa can be serine (S),valine (V) or alanine
      (A).
<220> FEATURE:
<221> NAME/KEY: MISC_FEATURE
<222> LOCATION: (5)..(5)
<223> OTHER INFORMATION: Xaa can be glutamine (Q) or histidine (H).
<220> FEATURE:
<221> NAME/KEY: MISC_FEATURE
<222> LOCATION: (6)..(6)
<223> OTHER INFORMATION: Xaa can be leucine (L), proline (P) or valine
      (V).

<400> SEQUENCE: 17

Gln Phe Xaa Leu Xaa Xaa Phe
1               5

<210> SEQ ID NO 18
<211> LENGTH: 6
<212> TYPE: PRT
<213> ORGANISM: artificial sequence
<220> FEATURE:
<223> OTHER INFORMATION: b6 motif

<400> SEQUENCE: 18

Ser Phe Glu Ile Lys Asn
1               5

<210> SEQ ID NO 19
<211> LENGTH: 5
<212> TYPE: PRT
<213> ORGANISM: aartificial sequence
<220> FEATURE:
<221> NAME/KEY: MISC_FEATURE
<222> LOCATION: (2)..(2)
<223> OTHER INFORMATION: Xaa can be Asparagine (N) or histidine (H).
<220> FEATURE:
<221> NAME/KEY: MISC_FEATURE
<222> LOCATION: (4)..(4)
<223> OTHER INFORMATION: Xaa can be methionine (M), leucine (L), valine
      (V) or isoleucine (I).

<400> SEQUENCE: 19

Leu Xaa Lys Xaa Asp
1               5

<210> SEQ ID NO 20
<211> LENGTH: 6
<212> TYPE: PRT
<213> ORGANISM: artificial sequence
<220> FEATURE:
<223> OTHER INFORMATION: b10 motif
<220> FEATURE:
<221> NAME/KEY: MISC_FEATURE
<222> LOCATION: (1)..(1)
<223> OTHER INFORMATION: Xaa can be arginine (R) or lysine (K).
<220> FEATURE:
<221> NAME/KEY: MISC_FEATURE
```

<222> LOCATION: (3)..(3)
<223> OTHER INFORMATION: Xaa can be methionine (M) or leucine (L).
<220> FEATURE:
<221> NAME/KEY: MISC_FEATURE
<222> LOCATION: (4)..(4)
<223> OTHER INFORMATION: Xaa can be valine (V), leucine (L) or ioleucine (I).

<400> SEQUENCE: 20

Xaa Cys Xaa Xaa Arg Phe
1               5

<210> SEQ ID NO 21
<211> LENGTH: 8
<212> TYPE: PRT
<213> ORGANISM: artificial sequence
<220> FEATURE:
<223> OTHER INFORMATION: b11 motif
<220> FEATURE:
<221> NAME/KEY: MISC_FEATURE
<222> LOCATION: (3)..(3)
<223> OTHER INFORMATION: Xaa can be phenylalanine (F) or isoleucine (I).
<220> FEATURE:
<221> NAME/KEY: MISC_FEATURE
<222> LOCATION: (5)..(5)
<223> OTHER INFORMATION: Xaa can be methionine (M), leucine (L), valine (V) or isoleucine (I).
<220> FEATURE:
<221> NAME/KEY: MISC_FEATURE
<222> LOCATION: (6)..(6)
<223> OTHER INFORMATION: Xaa can be glutamate (E) or glutamine (Q).
<220> FEATURE:
<221> NAME/KEY: MISC_FEATURE
<222> LOCATION: (7)..(7)
<223> OTHER INFORMATION: Xaa can be ysine (K) or arginine (R).

<400> SEQUENCE: 21

Tyr Gln Xaa Leu Xaa Xaa Xaa Glu
1               5

<210> SEQ ID NO 22
<211> LENGTH: 8
<212> TYPE: PRT
<213> ORGANISM: artificial sequence
<220> FEATURE:
<223> OTHER INFORMATION: b12 motif
<220> FEATURE:
<221> NAME/KEY: MISC_FEATURE
<222> LOCATION: (1)..(1)
<223> OTHER INFORMATION: Xaa can be phenylananine (F) or serine (S).
<220> FEATURE:
<221> NAME/KEY: MISC_FEATURE
<222> LOCATION: (3)..(3)
<223> OTHER INFORMATION: Xaa can be glutamate (E) or glutamine (Q).
<220> FEATURE:
<221> NAME/KEY: MISC_FEATURE
<222> LOCATION: (4)..(4)
<223> OTHER INFORMATION: Xaa can be threonine (T) or isoleucine (I).
<220> FEATURE:
<221> NAME/KEY: MISC_FEATURE
<222> LOCATION: (5)..(5)
<223> OTHER INFORMATION: Xaa can be glutamine (Q), histidine (H) or glutamate (E).
<220> FEATURE:
<221> NAME/KEY: MISC_FEATURE
<222> LOCATION: (7)..(7)
<223> OTHER INFORMATION: Xaa can be isoleucine (I), valine (V), serine (S) or phenylalanine (F).
<220> FEATURE:
<221> NAME/KEY: MISC_FEATURE
<222> LOCATION: (8)..(8)
<223> OTHER INFORMATION: Xaa can be leucine (L), methionine (M) or phenylananine (F).

<400> SEQUENCE: 22

```
Xaa Phe Xaa Xaa Xaa Phe Xaa Xaa
 1               5

<210> SEQ ID NO 23
<211> LENGTH: 45
<212> TYPE: PRT
<213> ORGANISM: artificial sequence
<220> FEATURE:
<223> OTHER INFORMATION: HS (human) TIFA F1

<400> SEQUENCE: 23

Met Thr Ser Phe Glu Asp Ala Asp Thr Glu Thr Val Thr Cys Leu
 1               5                  10                  15

Gln Met Thr Val Tyr His Pro Gly Gln Leu Gln Cys Gly Ile Phe Gln
                20                  25                  30

Ser Ile Ser Phe Asn Arg Glu Lys Leu Pro Ser Ser Glu
            35                  40                  45

<210> SEQ ID NO 24
<211> LENGTH: 46
<212> TYPE: PRT
<213> ORGANISM: artificial sequence
<220> FEATURE:
<223> OTHER INFORMATION: OC (rabbit) TIFA F1

<400> SEQUENCE: 24

Met Ser Ser Phe Glu Asp Ala Asp Thr Glu Thr Val Thr Cys Leu
 1               5                  10                  15

Gln Met Thr Val Tyr His Pro Ala Gln Phe Gln Ser Gly Ile Phe Gln
                20                  25                  30

Ala Ile Asp Phe Asn Lys Arg Asp Lys Leu Pro Ser Ser Glu
            35                  40                  45

<210> SEQ ID NO 25
<211> LENGTH: 47
<212> TYPE: PRT
<213> ORGANISM: artificial sequence
<220> FEATURE:
<223> OTHER INFORMATION: CL (dog) TIFA F1

<400> SEQUENCE: 25

Met Met Ser Asn Phe Glu Asp Ala Asp Thr Glu Glu Thr Val Thr Cys
 1               5                  10                  15

Leu Gln Ile Thr Val Tyr His Pro Gly Gln Leu Gln Asn Gly Ile Phe
                20                  25                  30

Gln Ser Ile Arg Phe Tyr Asn Arg Glu Lys Leu Pro Ser Ser Glu
            35                  40                  45

<210> SEQ ID NO 26
<211> LENGTH: 45
<212> TYPE: PRT
<213> ORGANISM: artificial sequence
<220> FEATURE:
<223> OTHER INFORMATION: MM (mouse) TIFA F1

<400> SEQUENCE: 26

Met Ser Thr Phe Glu Asp Ala Asp Thr Glu Thr Val Thr Cys Leu
 1               5                  10                  15

Gln Met Thr Ile Tyr His Pro Gly Gln Gln Ser Gly Ile Phe Lys Ser
                20                  25                  30

Ile Arg Phe Cys Ser Lys Glu Lys Phe Pro Ser Ile Glu
            35                  40                  45
```

```
<210> SEQ ID NO 27
<211> LENGTH: 46
<212> TYPE: PRT
<213> ORGANISM: artificial sequence
<220> FEATURE:
<223> OTHER INFORMATION: RN (rat) TIFA F1

<400> SEQUENCE: 27

Met Ser Thr Phe Glu Asp Ala Asp Thr Glu Glu Thr Val Thr Cys Leu
1               5                   10                  15

Gln Met Thr Ile Tyr His Pro Gly Gln Leu Gln Ser Gly Ile Phe Lys
            20                  25                  30

Ser Ile Arg Phe Cys Ser Lys Glu Lys Phe Pro Ser Ile Glu
        35                  40                  45

<210> SEQ ID NO 28
<211> LENGTH: 46
<212> TYPE: PRT
<213> ORGANISM: artificial sequence
<220> FEATURE:
<223> OTHER INFORMATION: CG (hamster) TIFA F1

<400> SEQUENCE: 28

Met Ser Ser Phe Glu Asp Ala Asp Thr Glu Glu Thr Val Thr Cys Leu
1               5                   10                  15

Gln Leu Thr Val Tyr His Pro Gly Gln Leu Gln Ser Gly Ile Phe Lys
            20                  25                  30

Ser Ile Arg Phe Cys Asn Lys Glu Lys Phe Pro Ser Ile Glu
        35                  40                  45

<210> SEQ ID NO 29
<211> LENGTH: 46
<212> TYPE: PRT
<213> ORGANISM: artificial sequence
<220> FEATURE:
<223> OTHER INFORMATION: CC (beaver) TIFA F1

<400> SEQUENCE: 29

Met Ser Asn Phe Glu Asp Ala Asp Thr Glu Glu Thr Leu Thr Cys Leu
1               5                   10                  15

His Val Thr Val Tyr His Ser Gly Lys Ser His Asn Gly Val Phe Gln
            20                  25                  30

Ser Ile Glu Phe Tyr Asn Arg Glu Lys Leu Pro Ser Gly Glu
        35                  40                  45

<210> SEQ ID NO 30
<211> LENGTH: 46
<212> TYPE: PRT
<213> ORGANISM: artificial sequeuce
<220> FEATURE:
<223> OTHER INFORMATION: CP (guinea pig) TIFA F1

<400> SEQUENCE: 30

Met Ser Ser Phe Glu Asp Ala Asp Thr Gln Glu Thr Val Thr Cys Leu
1               5                   10                  15

Gln Met Thr Val Tyr His Pro Gly His Val Gln Arg Gly Ile Phe Arg
            20                  25                  30

Ser Ile Asn Phe Ser Lys Arg Glu Lys Leu Pro Ser Ser Glu
        35                  40                  45

<210> SEQ ID NO 31
```

<211> LENGTH: 46
<212> TYPE: PRT
<213> ORGANISM: artificial sequence
<220> FEATURE:
<223> OTHER INFORMATION: BT (cattle) TIFA F1

<400> SEQUENCE: 31

Met Ser Ser Phe Glu Asp Ala Asp Thr Glu Met Val Thr Cys Leu
1               5                   10                  15

Gln Met Thr Leu Tyr His Pro Gly His Gln Arg Ser Gly Ile Phe Arg
            20                  25                  30

Ser Ile Lys Phe Ph

```
<220> FEATURE:
<223> OTHER INFORMATION: HS (human) F2

<400> SEQUENCE: 35

Val Val Lys Phe Gly Arg Asn Ser Asn Ile Cys His Tyr Thr Phe Gln
1               5                   10                  15

Asp Lys Gln Val Ser Arg Val Gln Phe Ser Leu Gln Leu Phe Lys Lys
            20                  25                  30

Phe Asn Ser Ser Val Leu Ser Phe Glu Ile Lys Asn Met Ser Lys Lys
        35                  40                  45

Thr Asn Leu Ile Val Asp Ser Arg Glu Leu
    50                  55

<210> SEQ ID NO 36
<211> LENGTH: 58
<212> TYPE: PRT
<213> ORGANISM: artificial sequence
<220> FEATURE:
<223> OTHER INFORMATION: OC (rabbit) TIFA F2

<400> SEQUENCE: 36

Val Val Lys Phe Gly Arg Asn Ser Lys Val Cys His Tyr Thr Phe Gln
1               5                   10                  15

Asp Lys Gln Ala Ser Arg Val Gln Phe Ser Leu Gln Leu Phe Lys Gln
            20                  25                  30

Phe Asn Ser Ser Val Leu Ser Phe Glu Ile Lys Asn Met Ser Arg Lys
        35                  40                  45

Thr Ser Leu Ile Val Asp Ser Gln Glu Leu
    50                  55

<210> SEQ ID NO 37
<211> LENGTH: 58
<212> TYPE: PRT
<213> ORGANISM: artificial sequence
<220> FEATURE:
<223> OTHER INFORMATION: CL ( dog) TIFA F2

<400> SEQUENCE: 37

Val Val Lys Phe Gly Arg Asn Ser Asn Ile Cys Arg Tyr Thr Phe Gln
1               5                   10                  15

Asp Lys Gln Val Ser Arg Val Gln Phe Ser Leu Gln Leu Phe Lys Lys
            20                  25                  30

Phe Asp Ser Ser Val Leu Ser Phe Glu Ile Lys Asn Met Ser Lys Lys
        35                  40                  45

Thr Asn Leu Leu Val Asp Asn Lys Glu Leu
    50                  55

<210> SEQ ID NO 38
<211> LENGTH: 58
<212> TYPE: PRT
<213> ORGANISM: artificial sequence
<220> FEATURE:
<223> OTHER INFORMATION: MM (mouse) TIFA F2

<400> SEQUENCE: 38

Val Val Lys Phe Gly Arg Asn Ser Asn Met Cys Gln Tyr Thr Phe Gln
1               5                   10                  15

Asp Lys Gln Val Ser Arg Ile Gln Phe Val Leu Gln Pro Phe Lys Gln
            20                  25                  30

Phe Asn Ser Ser Val Leu Ser Phe Glu Ile Lys Asn Met Ser Lys Lys
        35                  40                  45
```

Thr Ser Leu Met Val Asp Asn Gln Glu Leu
    50                  55

<210> SEQ ID NO 39
<211> LENGTH: 58
<212> TYPE: PRT
<213> ORGANISM: artificial sequence
<220> FEATURE:
<223> OTHER INFORMATION: RN (rat) TIFA F2

<400> SEQUENCE: 39

Val Val Lys Phe Gly Arg Asn Ser Asn Met Cys Gln Tyr Thr Phe Gln
1               5                   10                  15

Asp Lys Gln Val Ser Arg Val Gln Phe Ala Leu Gln Pro Phe Lys Gln
            20                  25                  30

Phe Asn Ser Ser Val Leu Ser Phe Glu Ile Lys Asn Met Ser Lys Lys
        35                  40                  45

Thr Ser Leu Met Val Asp Asn Gln Glu Leu
    50                  55

<210> SEQ ID NO 40
<211> LENGTH: 58
<212> TYPE: PRT
<213> ORGANISM: artificial sequence
<220> FEATURE:
<223> OTHER INFORMATION: CG (hamster) TIFA F2

<400> SEQUENCE: 40

Glu Val Lys Phe Gly Arg Asn Ser Asn Ile Cys Arg Tyr Thr Phe Gln
1               5                   10                  15

Asp Lys Gln Val Ser Arg Val Gln Phe Ala Leu Gln Pro Phe Lys Gln
            20                  25                  30

Phe Asn Ser Ser Val Leu Ser Phe Glu Ile Lys Asn Met Ser Lys Lys
        35                  40                  45

Thr Ser Leu Met Val Asp Asn Gln Glu Leu
    50                  55

<210> SEQ ID NO 41
<211> LENGTH: 58
<212> TYPE: PRT
<213> ORGANISM: artificial sequence
<220> FEATURE:
<223> OTHER INFORMATION: CC (beaver) TIFA F2

<400> SEQUENCE: 41

Val Val Lys Phe Gly Arg Asn Ser Ser Ile Cys Arg Tyr Thr Phe Gln
1               5                   10                  15

Asp Lys Gln Val Ser Arg Val Gln Phe Ser Leu Gln Pro Phe Lys Gln
            20                  25                  30

Phe Asn Ser Ser Val Leu Ser Phe Glu Ile Lys Asn Met Ser Lys Lys
        35                  40                  45

Thr Ser Leu Ile Val Asp Ser Gln Glu Leu
    50                  55

<210> SEQ ID NO 42
<211> LENGTH: 58
<212> TYPE: PRT
<213> ORGANISM: artificial sequence
<220> FEATURE:
<223> OTHER INFORMATION: CP (guinea pig) TIFA F2

<400> SEQUENCE: 42

```
Val Val Lys Phe Gly Arg Asn Ser Ser Cys His Tyr Ile Phe Gln
1               5                   10                  15

Asp Lys Gln Ala Ser Arg Val Gln Phe Ser Leu His Pro Phe Lys Pro
                20                  25                  30

Phe Asn Ser Ser Val Leu Ser Phe Glu Ile Lys Asn Leu Ser Lys Lys
            35                  40                  45

Thr Ser Leu Ile Val Asp Ser Arg Glu Leu
        50                  55
```

<210> SEQ ID NO 43
<211> LENGTH: 58
<212> TYPE: PRT
<213> ORGANISM: artificial sequence
<220> FEATURE:
<223> OTHER INFORMATION: BT (cattle) TIFA F2

<400> SEQUENCE: 43

```
Val Val Lys Phe Gly Arg Asn Ser His Thr Cys Asn Tyr Ile Phe Gln
1               5                   10                  15

Asp Lys Gln Val Ser Arg Val Gln Phe Ser Leu Gln Val Phe Lys Lys
                20                  25                  30

Phe Asn Ser Ser Val Val Ser Phe Glu Ile Lys Asn Met Ser Lys Lys
            35                  40                  45

Thr Ser Leu Leu Val Asp Asn Lys Glu Leu
        50                  55
```

<210> SEQ ID NO 44
<211> LENGTH: 58
<212> TYPE: PRT
<213> ORGANISM: artificial sequence
<220> FEATURE:
<223> OTHER INFORMATION: CH (goat) TIFA F2

<400> SEQUENCE: 44

```
Val Val Lys Phe Gly Arg Asn Ser Ser Thr Cys Arg Tyr Thr Phe Gln
1               5                   10                  15

Asp Lys Gln Val Ser Arg Val Gln Phe Ser Leu Gln Leu Phe Lys Lys
                20                  25                  30

Phe Asp Ser Ser Val Val Ser Phe Glu Ile Lys Asn Met Ser Lys Lys
            35                  40                  45

Thr Asn Leu Leu Val Asp Asp Lys Glu Leu
        50                  55
```

<210> SEQ ID NO 45
<211> LENGTH: 57
<212> TYPE: PRT
<213> ORGANISM: artificial sequence
<220> FEATURE:
<223> OTHER INFORMATION: SS (pig) TIFA F2

<400> SEQUENCE: 45

```
Val Val Lys Phe Gly Arg Asn Ser Ile Cys Gln Tyr Thr Phe Gln Asp
1               5                   10                  15

Lys His Ala Ser Arg Val Gln Phe Ser Leu His Leu Phe Lys Lys Phe
                20                  25                  30

Asp Ser Ser Val Leu Ser Phe Glu Ile Lys Asn Met Ser Lys Lys Thr
            35                  40                  45

Ser Leu Ile Val Asp Asn Gln Glu Leu
        50                  55
```

```
<210> SEQ ID NO 46
<211> LENGTH: 58
<212> TYPE: PRT
<213> ORGANISM: artificial sequence
<220> FEATURE:
<223> OTHER INFORMATION: EC (horse) TIFA F2

<400> SEQUENCE: 46

Glu Val Lys Phe Gly Arg Ser Ser Lys Val Cys Asn Tyr Thr Phe Gln
1               5                   10                  15

Asp Arg Gln Val Ser Arg Val Gln Phe Ser Leu Gln Leu Phe Lys Lys
            20                  25                  30

Phe Asp Ser Ser Val Leu Ser Phe Glu Ile Lys Asn Met Ser Lys Arg
        35                  40                  45

Thr Ser Leu Ile Val Asp Asn Arg Thr Leu
    50                  55

<210> SEQ ID NO 47
<211> LENGTH: 81
<212> TYPE: PRT
<213> ORGANISM: artificial sequence
<220> FEATURE:
<223> OTHER INFORMATION: HS (human) TIFA F3

<400> SEQUENCE: 47

Gly Tyr Leu Asn Lys Met Asp Leu Pro Tyr Arg Cys Met Val Arg Phe
1               5                   10                  15

Gly Glu Tyr Gln Phe Leu Met Glu Lys Glu Asp Gly Glu Ser Leu Glu
            20                  25                  30

Phe Phe Glu Thr Gln Phe Ile Leu Ser Pro Arg Ser Leu Leu Gln Glu
        35                  40                  45

Asn Asn Trp Pro Pro His Arg Pro Ile Pro Glu Tyr Gly Thr Tyr Ser
    50                  55                  60

Leu Cys Ser Ser Gln Ser Ser Ser Pro Thr Glu Met Asp Glu Asn Glu
65                  70                  75                  80

Ser

<210> SEQ ID NO 48
<211> LENGTH: 81
<212> TYPE: PRT
<213> ORGANISM: artificial sequence
<220> FEATURE:
<223> OTHER INFORMATION: OC (rabbit) TIFA F3

<400> SEQUENCE: 48

Gly Tyr Leu Asn Lys Leu Asp Leu Pro Tyr Lys Cys Met Val Arg Phe
1               5                   10                  15

Ser Glu Tyr Gln Phe Leu Met Glu Lys Glu Asp Gly Glu Ala Leu Asp
            20                  25                  30

Ser Phe Glu Thr Gln Phe Ile Leu Ser Pro Arg Pro Leu Leu Gln Glu
        35                  40                  45

Asn Ile Trp Pro Pro His Lys Pro Ile Pro Glu Tyr Gly Ile Tyr Ser
    50                  55                  60

Ser Cys Ser Ala Gln Ser Thr Ser Pro Thr Glu Met Asp Glu Asp Glu
65                  70                  75                  80

Leu

<210> SEQ ID NO 49
<211> LENGTH: 81
```

```
<212> TYPE: PRT
<213> ORGANISM: artificial sequence
<220> FEATURE:
<223> OTHER INFORMATION: CL (dog) TIFA F3

<400> SEQUENCE: 49

Cys Tyr Leu Asn Lys Ile Asp Leu Pro Tyr Lys Cys Met Val Arg Phe
 1               5                  10                  15

Gly Glu Tyr Gln Phe Leu Ile Glu Lys Glu Asp Gly Glu Ser Leu Glu
             20                  25                  30

Phe Phe Glu Thr Gln Phe Ile Leu Ser Pro Arg Ser Leu Leu Gln Glu
         35                  40                  45

Asn Asn Trp Pro Ile Gln Lys Pro Ile Pro Glu Tyr Gly Ser Tyr Ser
     50                  55                  60

Ser Cys Phe Thr Gln Asn Thr Ser Pro Thr Glu Met Asp Glu Asn Glu
 65                  70                  75                  80

Leu

<210> SEQ ID NO 50
<211> LENGTH: 81
<212> TYPE: PRT
<213> ORGANISM: artificial sequence
<220> FEATURE:
<223> OTHER INFORMATION: MM (mouse) TIFA F3

<400> SEQUENCE: 50

Gly Tyr Leu Asn Lys Met Asp Leu Pro Tyr Lys Cys Met Leu Arg Phe
 1               5                  10                  15

Gly Glu Tyr Gln Phe Leu Leu Gln Lys Glu Asp Gly Glu Ser Val Glu
             20                  25                  30

Ser Phe Glu Thr Gln Phe Ile Met Ser Ser Arg Pro Leu Leu Gln Glu
         35                  40                  45

Asn Asn Trp Pro Thr Gln Asn Pro Ile Pro Glu Asp Gly Met Tyr Ser
     50                  55                  60

Ser Tyr Phe Thr His Arg Ser Ser Pro Ser Glu Met Asp Glu Asn Glu
 65                  70                  75                  80

Leu

<210> SEQ ID NO 51
<211> LENGTH: 81
<212> TYPE: PRT
<213> ORGANISM: artificial sequence
<220> FEATURE:
<223> OTHER INFORMATION: RN (rat) TIFA F3

<400> SEQUENCE: 51

Gly Tyr Leu Asn Lys Met Asp Leu Pro Tyr Lys Cys Met Leu Arg Phe
 1               5                  10                  15

Gly Glu Tyr Gln Phe Leu Leu Gln Lys Glu Asp Gly Glu Ser Val Glu
             20                  25                  30

Ser Phe Glu Thr Gln Phe Ile Leu Ser Pro Arg Pro Leu Leu Gln Glu
         35                  40                  45

Asn Asn Trp Pro Thr Gln Ser Pro Ile Pro Glu Asp Gly Val Tyr Ser
     50                  55                  60

Ser Tyr Phe Thr His Arg Ser Ser Pro Ala Glu Met Asp Glu Asn Glu
 65                  70                  75                  80

Leu
```

```
<210> SEQ ID NO 52
<211> LENGTH: 81
<212> TYPE: PRT
<213> ORGANISM: artificial sequence
<220> FEATURE:
<223> OTHER INFORMATION: CG (hamster) TIFA F3

<400> SEQUENCE: 52

Gly Tyr Leu Asn Lys Met Asp Leu Pro Tyr Lys Cys Leu Leu Arg Phe
1               5                   10                  15

Gly Glu Tyr Gln Phe Leu Leu Glu Lys Glu Asp Gly Glu Ser Val Glu
            20                  25                  30

Ser Phe Glu Thr Gln Phe Ile Leu Ser Pro Arg Pro Leu Leu Gln Glu
        35                  40                  45

Asn Asn Trp Pro Thr Gln Ser Pro Ile Pro Glu Asp Gly Gly Tyr Ser
    50                  55                  60

Ser Tyr Phe Thr His Arg Thr Ser Pro Thr Glu Met Asp Glu Asn Glu
65                  70                  75                  80

Leu

<210> SEQ ID NO 53
<211> LENGTH: 81
<212> TYPE: PRT
<213> ORGANISM: artificial sequence
<220> FEATURE:
<223> OTHER INFORMATION: CC (beaver) TIFA F3

<400> SEQUENCE: 53

Gly Tyr Leu Asn Lys Met Asp Leu Pro Tyr Arg Cys Met Val Arg Phe
1               5                   10                  15

Gly Glu Tyr Gln Phe Leu Leu Glu Lys Glu Asp Gly Glu Ser Leu Glu
            20                  25                  30

Ser Phe Gln Thr His Phe Ile Leu Ser Pro Arg Pro Leu Leu Gln Glu
        35                  40                  45

Asn Asn Trp Pro Ala Gln Thr Pro Ile Pro Glu Asp Gly Gly Tyr Ser
    50                  55                  60

Ser Tyr Leu Thr Pro Ser Thr Phe Pro Thr Glu Ile Asp Glu Asn Glu
65                  70                  75                  80

Leu

<210> SEQ ID NO 54
<211> LENGTH: 81
<212> TYPE: PRT
<213> ORGANISM: artificial sequence
<220> FEATURE:
<223> OTHER INFORMATION: CP (guinea pig) TIFA F3

<400> SEQUENCE: 54

Arg Tyr Leu Asn Lys Met Asp Leu Pro Tyr Arg Cys Met Val Arg Phe
1               5                   10                  15

Gly Glu Tyr Gln Phe Leu Leu Glu Arg Glu Asp Gly Glu Ser Leu Glu
            20                  25                  30

Ser Phe Glu Thr Gln Phe Val Phe Ser Pro Arg Pro Leu Leu Gln Glu
        35                  40                  45

Asn Ser Trp Pro Thr Gln Ser Pro Ile Pro Glu Asp Gly Ser Phe Ser
    50                  55                  60

Ser Gly Tyr Thr Arg Ser Ser Phe Pro Met Glu Met Asp Glu Asn Glu
65                  70                  75                  80

Trp
```

<210> SEQ ID NO 55
<211> LENGTH: 81
<212> TYPE: PRT
<213> ORGANISM: artificial sequence
<220> FEATURE:
<223> OTHER INFORMATION: BT (cattle) TIFA F3

<400> SEQUENCE: 55

Gly Tyr Leu Asn Lys Met Asp Leu Pro Asp Lys Cys Met Ile Arg Phe
1               5                   10                  15

Gly Asp Tyr Gln Phe Leu Val Glu Lys Glu Asp Gly Glu Ser Leu Glu
            20                  25                  30

Phe Phe Glu Ile Gln Phe Ser Leu Ser Lys Lys Pro Leu Leu Gln Glu
        35                  40                  45

Asn Asn Trp Leu Ser Gln Glu Pro Ile Pro Glu Cys Gly Ser Tyr Ser
    50                  55                  60

Ser Cys Leu Thr Gln Asn Asn Ser Pro Met Glu Val Gly Glu Asn Glu
65                  70                  75                  80

Trp

<210> SEQ ID NO 56
<211> LENGTH: 81
<212> TYPE: PRT
<213> ORGANISM: artificial sequence
<220> FEATURE:
<223> OTHER INFORMATION: CH (goat) TIFA F3

<400> SEQUENCE: 56

Ser Tyr Leu Asn Lys Met Asp Leu Pro Asp Lys Cys Leu Ile Arg Phe
1               5                   10                  15

Gly Asp Tyr Gln Phe Leu Val Glu Lys Glu Asp Gly Glu Ser Leu Glu
            20                  25                  30

Phe Phe Glu Ile Gln Phe Phe Leu Ser Ile Arg Pro Leu Leu Gln Glu
        35                  40                  45

Asn Lys Trp Leu Pro Gln Lys Pro Thr Pro Glu Cys Gly Ser Cys Ser
    50                  55                  60

Pro Cys Ser Thr Gln Asn Asn Ser Pro Met Glu Ala Gly Glu Asn Glu
65                  70                  75                  80

Trp

<210> SEQ ID NO 57
<211> LENGTH: 81
<212> TYPE: PRT
<213> ORGANISM: artificial sequence
<220> FEATURE:
<223> OTHER INFORMATION: SS (pig) TIFA F3

<400> SEQUENCE: 57

Gly Tyr Leu Asn Lys Met Asp Leu Pro Pro Lys Cys Met Val Arg Phe
1               5                   10                  15

Gly Asp Tyr Gln Phe Leu Ile Glu Lys Glu Asp Gly Glu Ser Leu Glu
            20                  25                  30

Phe Phe Glu Ile Gln Phe Ile Leu Ser Thr Arg Ser Leu Leu Gln Glu
        35                  40                  45

Asn Asn Trp Leu Pro Gln Lys Pro Ile Pro Glu Cys Gly Asn Tyr Leu
    50                  55                  60

Ser Cys Ser Thr Gln Gly Asn Ser Pro Ile Glu Met Gly Glu Asn Glu
65                  70                  75                  80

Trp

<210> SEQ ID NO 58
<211> LENGTH: 81
<212> TYPE: PRT
<213> ORGANISM: artificial sequence
<220> FEATURE:
<223> OTHER INFORMATION: EC (horse) TIFA F3

<400> SEQUENCE: 58

Asp Phe Leu His Lys Val Asp Leu Pro Asp Arg Cys Met Ile Arg Phe
1               5                   10                  15

Gly Asp Tyr Gln Ile Leu Met Glu Lys Glu Asp Gly Val Ser Leu Glu
            20                  25                  30

Phe Phe Glu Thr Glu Phe Ile Leu Ser Pro Arg Ser Leu Leu Gln Lys
        35                  40                  45

Asn Tyr Trp Pro Pro Gln Asn Pro Ile Pro Glu Tyr Cys His Ser Val
    50                  55                  60

Trp Ser Ser Ser Gln Ser Thr Ser Pro Met Glu Thr Asp Glu Asn Glu
65                  70                  75                  80

Leu

<210> SEQ ID NO 59
<211> LENGTH: 41
<212> TYPE: PRT
<213> ORGANISM: artificial sequence
<220> FEATURE:
<223> OTHER INFORMATION: HS (human) TIFA C-terminal loop sequence

<400> SEQUENCE: 59

Ser Pro Arg Ser Leu Leu Gln Glu Asn Asn Trp Pro Pro His Arg Pro
1               5                   10                  15

Ile Pro Glu Tyr Gly Thr Tyr Ser Leu Cys Ser Ser Gln Ser Ser Ser
            20                  25                  30

Pro Thr Glu Met Asp Glu Asn Glu Ser
        35                  40

<210> SEQ ID NO 60
<211> LENGTH: 41
<212> TYPE: PRT
<213> ORGANISM: artificial sequence
<220> FEATURE:
<223> OTHER INFORMATION: OC (rabbit) TIFA C-terminal loop sequence

<400> SEQUENCE: 60

Ser Pro Arg Pro Leu Leu Gln Glu Asn Ile Trp Pro Pro His Lys Pro
1               5                   10                  15

Ile Pro Glu Tyr Gly Ile Tyr Ser Ser Cys Ser Ala Gln Ser Thr Ser
            20                  25                  30

Pro Thr Glu Met Asp Glu Asp Glu Leu
        35                  40

<210> SEQ ID NO 61
<211> LENGTH: 41
<212> TYPE: PRT
<213> ORGANISM: artificial sequence
<220> FEATURE:
<223> OTHER INFORMATION: CL (dog) TIFA C-terminal loop sequence

<400> SEQUENCE: 61

Ser Pro Arg Ser Leu Leu Gln Glu Asn Asn Trp Pro Ile Gln Lys Pro

```
1               5                   10                  15
Ile Pro Glu Tyr Gly Ser Tyr Ser Cys Phe Thr Gln Asn Thr Ser
            20                  25                  30

Pro Thr Glu Met Asp Glu Asn Glu Leu
        35                  40
```

<210> SEQ ID NO 62
<211> LENGTH: 41
<212> TYPE: PRT
<213> ORGANISM: artificial sequence
<220> FEATURE:
<223> OTHER INFORMATION: MM (mouse) TIFA C-terminal loop sequence

<400> SEQUENCE: 62

```
Ser Ser Arg Pro Leu Leu Gln Glu Asn Asn Trp Pro Thr Gln Asn Pro
1               5                   10                  15

Ile Pro Glu Asp Gly Met Tyr Ser Ser Tyr Phe Thr His Arg Ser Ser
            20                  25                  30

Pro Ser Glu Met Asp Glu Asn Glu Leu
        35                  40
```

<210> SEQ ID NO 63
<211> LENGTH: 41
<212> TYPE: PRT
<213> ORGANISM: artificial sequence
<220> FEATURE:
<223> OTHER INFORMATION: RN (rat) TIFA C=terminal loop sequencce

<400> SEQUENCE: 63

```
Ser Pro Arg Pro Leu Leu Gln Glu Asn Asn Trp Pro Thr Gln Ser Pro
1               5                   10                  15

Ile Pro Glu Asp Gly Val Tyr Ser Ser Tyr Phe Thr His Arg Ser Ser
            20                  25                  30

Pro Ala Glu Met Asp Glu Asn Glu Leu
        35                  40
```

<210> SEQ ID NO 64
<211> LENGTH: 41
<212> TYPE: PRT
<213> ORGANISM: artificial sequence
<220> FEATURE:
<223> OTHER INFORMATION: CG (hamster) TIFA C-termimal loop sequence

<400> SEQUENCE: 64

```
Ser Pro Arg Pro Leu Leu Gln Glu Asn Asn Trp Pro Thr Gln Ser Pro
1               5                   10                  15

Ile Pro Glu Asp Gly Gly Tyr Ser Ser Tyr Phe Thr His Arg Thr Ser
            20                  25                  30

Pro Thr Glu Met Asp Glu Asn Glu Leu
        35                  40
```

<210> SEQ ID NO 65
<211> LENGTH: 41
<212> TYPE: PRT
<213> ORGANISM: artificial sequence
<220> FEATURE:
<223> OTHER INFORMATION: CC (beaver) TIFA C-terminal loop sequence

<400> SEQUENCE: 65

```
Ser Pro Arg Pro Leu Leu Gln Glu Asn Asn Trp Pro Ala Gln Thr Pro
1               5                   10                  15

Ile Pro Glu Asp Gly Gly Tyr Ser Ser Tyr Leu Thr Pro Ser Thr Phe
```

```
                20                  25                  30

Pro Thr Glu Ile Asp Glu Asn Glu Leu
        35                  40

<210> SEQ ID NO 66
<211> LENGTH: 41
<212> TYPE: PRT
<213> ORGANISM: artificial sequence
<220> FEATURE:
<223> OTHER INFORMATION: CP (guinea pig) C-terminal loop sequence

<400> SEQUENCE: 66

Ser Pro Arg Pro Leu Leu Gln Glu Asn Ser Trp Pro Thr Gln Ser Pro
1               5                   10                  15

Ile Pro Glu Asp Gly Ser Phe Ser Ser Gly Tyr Thr Arg Ser Ser Phe
            20                  25                  30

Pro Met Glu Met Asp Glu Asn Glu Trp
        35                  40

<210> SEQ ID NO 67
<211> LENGTH: 41
<212> TYPE: PRT
<213> ORGANISM: artificial sequence
<220> FEATURE:
<223> OTHER INFORMATION: BT (cattle) TIFA C-terminal loop sequence

<400> SEQUENCE: 67

Ser Lys Lys Pro Leu Leu Gln Glu Asn Asn Trp Leu Ser Gln Glu Pro
1               5                   10                  15

Ile Pro Glu Cys Gly Ser Tyr Ser Ser Cys Leu Thr Gln Asn Asn Ser
            20                  25                  30

Pro Met Glu Val Gly Glu Asn Glu Trp
        35                  40

<210> SEQ ID NO 68
<211> LENGTH: 41
<212> TYPE: PRT
<213> ORGANISM: artificial sequence
<220> FEATURE:
<223> OTHER INFORMATION: CH (goat) TIFA C-terminal loop sequence

<400> SEQUENCE: 68

Ser Ile Arg Pro Leu Leu Gln Glu Asn Lys Trp Leu Pro Gln Lys Pro
1               5                   10                  15

Thr Pro Glu Cys Gly Ser Cys Ser Pro Cys Ser Thr Gln Asn Asn Ser
            20                  25                  30

Pro Met Glu Ala Gly Glu Asn Glu Trp
        35                  40

<210> SEQ ID NO 69
<211> LENGTH: 41
<212> TYPE: PRT
<213> ORGANISM: artificial sequence
<220> FEATURE:
<223> OTHER INFORMATION: SS (pig) TIFA C-terminal loop sequence

<400> SEQUENCE: 69

Ser Thr Arg Ser Leu Leu Gln Glu Asn Asn Trp Leu Pro Gln Lys Pro
1               5                   10                  15

Ile Pro Glu Cys Gly Asn Tyr Leu Ser Cys Ser Thr Gln Gly Asn Ser
            20                  25                  30

Pro Ile Glu Met Gly Glu Asn Glu Trp
```

```
                35                  40

<210> SEQ ID NO 70
<211> LENGTH: 41
<212> TYPE: PRT
<213> ORGANISM: artificial sequence
<220> FEATURE:
<223> OTHER INFORMATION: EC (horse) TIFA C-terminal loop sequence

<400> SEQUENCE: 70

Ser Pro Arg Ser Leu Leu Gln Lys Asn Tyr Trp Pro Gln Asn Pro
1               5                   10                  15

Ile Pro Glu Tyr Cys His Ser Val Trp Ser Ser Ser Gln Ser Thr Ser
            20                  25                  30

Pro Met Glu Thr Asp Glu Asn Glu Leu
        35                  40

<210> SEQ ID NO 71
<211> LENGTH: 103
<212> TYPE: PRT
<213> ORGANISM: artificial sequence
<220> FEATURE:
<223> OTHER INFORMATION: HS (human) TIFA F1+F2

<400> SEQUENCE: 71

Met Thr Ser Phe Glu Asp Ala Asp Thr Glu Glu Thr Val Thr Cys Leu
1               5                   10                  15

Gln Met Thr Val Tyr His Pro Gly Gln Leu Gln Cys Gly Ile Phe Gln
            20                  25                  30

Ser Ile Ser Phe Asn Arg Glu Lys Leu Pro Ser Ser Glu Val Val Lys
        35                  40                  45

Phe Gly Arg Asn Ser Asn Ile Cys His Tyr Thr Phe Gln Asp Lys Gln
50                  55                  60

Val Ser Arg Val Gln Phe Ser Leu Gln Leu Phe Lys Lys Phe Asn Ser
65                  70                  75                  80

Ser Val Leu Ser Phe Glu Ile Lys Asn Met Ser Lys Lys Thr Asn Leu
                85                  90                  95

Ile Val Asp Ser Arg Glu Leu
            100

<210> SEQ ID NO 72
<211> LENGTH: 104
<212> TYPE: PRT
<213> ORGANISM: artificial sequence
<220> FEATURE:
<223> OTHER INFORMATION: OC (rabbit) TIFA F1+F2

<400> SEQUENCE: 72

Met Ser Ser Phe Glu Asp Ala Asp Thr Glu Glu Thr Val Thr Cys Leu
1               5                   10                  15

Gln Met Thr Val Tyr His Pro Ala Gln Phe Gln Ser Gly Ile Phe Gln
            20                  25                  30

Ala Ile Asp Phe Asn Lys Arg Asp Lys Leu Pro Ser Ser Glu Val Val
        35                  40                  45

Lys Phe Gly Arg Asn Ser Lys Val Cys His Tyr Thr Phe Gln Asp Lys
    50                  55                  60

Gln Ala Ser Arg Val Gln Phe Ser Leu Gln Leu Phe Lys Gln Phe Asn
65                  70                  75                  80

Ser Ser Val Leu Ser Phe Glu Ile Lys Asn Met Ser Arg Lys Thr Ser
                85                  90                  95
```

```
Leu Ile Val Asp Ser Gln Glu Leu
            100

<210> SEQ ID NO 73
<211> LENGTH: 105
<212> TYPE: PRT
<213> ORGANISM: artificial sequence
<220> FEATURE:
<223> OTHER INFORMATION: CL (dog) TIFA F1+F2

<400> SEQUENCE: 73

Met Met Ser Asn Phe Glu Asp Ala Asp Thr Glu Glu Thr Val Thr Cys
1               5                   10                  15

Leu Gln Ile Thr Val Tyr His Pro Gly Gln Leu Gln Asn Gly Ile Phe
            20                  25                  30

Gln Ser Ile Arg Phe Tyr Asn Arg Glu Lys Leu Pro Ser Ser Glu Val
        35                  40                  45

Val Lys Phe Gly Arg Asn Ser Asn Ile Cys Arg Tyr Thr Phe Gln Asp
    50                  55                  60

Lys Gln Val Ser Arg Val Gln Phe Ser Leu Gln Leu Phe Lys Lys Phe
65                  70                  75                  80

Asp Ser Ser Val Leu Ser Phe Glu Ile Lys Asn Met Ser Lys Lys Thr
                85                  90                  95

Asn Leu Leu Val Asp Asn Lys Glu Leu
            100                 105

<210> SEQ ID NO 74
<211> LENGTH: 103
<212> TYPE: PRT
<213> ORGANISM: artificial sequence
<220> FEATURE:
<223> OTHER INFORMATION: MM (mouse) TIFA F1+F2

<400> SEQUENCE: 74

Met Ser Thr Phe Glu Asp Ala Asp Thr Glu Thr Val Thr Cys Leu
1               5                   10                  15

Gln Met Thr Ile Tyr His Pro Gly Gln Gln Ser Gly Ile Phe Lys Ser
            20                  25                  30

Ile Arg Phe Cys Ser Lys Glu Lys Phe Pro Ser Ile Glu Val Val Lys
        35                  40                  45

Phe Gly Arg Asn Ser Asn Met Cys Gln Tyr Thr Phe Gln Asp Lys Gln
    50                  55                  60

Val Ser Arg Ile Gln Phe Val Leu Gln Pro Lys Gln Phe Asn Ser
65                  70                  75                  80

Ser Val Leu Ser Phe Glu Ile Lys Asn Met Ser Lys Lys Thr Ser Leu
                85                  90                  95

Met Val Asp Asn Gln Glu Leu
            100

<210> SEQ ID NO 75
<211> LENGTH: 104
<212> TYPE: PRT
<213> ORGANISM: artificial sequence
<220> FEATURE:
<223> OTHER INFORMATION: RN (rat) TIFA F1+F2

<400> SEQUENCE: 75

Met Ser Thr Phe Glu Asp Ala Asp Thr Glu Glu Thr Val Thr Cys Leu
1               5                   10                  15
```

```
Gln Met Thr Ile Tyr His Pro Gly Gln Leu Gln Ser Gly Ile Phe Lys
            20                  25                  30

Ser Ile Arg Phe Cys Ser Lys Glu Lys Phe Pro Ser Ile Glu Val Val
        35                  40                  45

Lys Phe Gly Arg Asn Ser Asn Met Cys Gln Tyr Thr Phe Gln Asp Lys
50                  55                  60

Gln Val Ser Arg Val Gln Phe Ala Leu Gln Pro Phe Lys Gln Phe Asn
65                  70                  75                  80

Ser Ser Val Leu Ser Phe Glu Ile Lys Asn Met Ser Lys Lys Thr Ser
                85                  90                  95

Leu Met Val Asp Asn Gln Glu Leu
            100

<210> SEQ ID NO 76
<211> LENGTH: 104
<212> TYPE: PRT
<213> ORGANISM: artificial sequence
<220> FEATURE:
<223> OTHER INFORMATION: CG (hamster) TIFA F1+F2

<400> SEQUENCE: 76

Met Ser Ser Phe Glu Asp Ala Asp Thr Glu Glu Thr Val Thr Cys Leu
1               5                   10                  15

Gln Leu Thr Val Tyr His Pro Gly Gln Leu Gln Ser Gly Ile Phe Lys
            20                  25                  30

Ser Ile Arg Phe Cys Asn Lys Glu Lys Phe Pro Ser Ile Glu Glu Val
        35                  40                  45

Lys Phe Gly Arg Asn Ser Asn Ile Cys Arg Tyr Thr Phe Gln Asp Lys
50                  55                  60

Gln Val Ser Arg Val Gln Phe Ala Leu Gln Pro Phe Lys Gln Phe Asn
65                  70                  75                  80

Ser Ser Val Leu Ser Phe Glu Ile Lys Asn Met Ser Lys Lys Thr Ser
                85                  90                  95

Leu Met Val Asp Asn Gln Glu Leu
            100

<210> SEQ ID NO 77
<211> LENGTH: 104
<212> TYPE: PRT
<213> ORGANISM: artificial sequence
<220> FEATURE:
<223> OTHER INFORMATION: CC (beaver) TIFA F1+F2

<400> SEQUENCE: 77

Met Ser Asn Phe Glu Asp Ala Asp Thr Glu Glu Thr Leu Thr Cys Leu
1               5                   10                  15

His Val Thr Val Tyr His Ser Gly Lys Ser His Asn Gly Val Phe Gln
            20                  25                  30

Ser Ile Glu Phe Tyr Asn Arg Glu Lys Leu Pro Ser Gly Glu Val Val
        35                  40                  45

Lys Phe Gly Arg Asn Ser Ser Ile Cys Arg Tyr Thr Phe Gln Asp Lys
50                  55                  60

Gln Val Ser Arg Val Gln Phe Ser Leu Gln Pro Phe Lys Gln Phe Asn
65                  70                  75                  80

Ser Ser Val Leu Ser Phe Glu Ile Lys Asn Met Ser Lys Lys Thr Ser
                85                  90                  95

Leu Ile Val Asp Ser Gln Glu Leu
            100
```

<210> SEQ ID NO 78
<211> LENGTH: 104
<212> TYPE: PRT
<213> ORGANISM: artificial sequence
<220> FEATURE:
<223> OTHER INFORMATION: CP (guinea pig) TIFA F1+F2

<400> SEQUENCE: 78

Met Ser Ser Phe Glu Asp Ala Asp Thr Gln Glu Thr Val Thr Cys Leu
1               5                   10                  15

Gln Met Thr Val Tyr His Pro Gly His Val Gln Arg Gly Ile Phe Arg
            20                  25                  30

Ser Ile Asn Phe Ser Lys Arg Glu Lys Leu Pro Ser Ser Glu Val Val
        35                  40                  45

Lys Phe Gly Arg Asn Ser Ser Cys His Tyr Ile Phe Gln Asp Lys
    50                  55                  60

Gln Ala Ser Arg Val Gln Phe Ser Leu His Pro Phe Lys Pro Phe Asn
65                  70                  75                  80

Ser Ser Val Leu Ser Phe Glu Ile Lys Asn Leu Ser Lys Lys Thr Ser
                85                  90                  95

Leu Ile Val Asp Ser Arg Glu Leu
            100

<210> SEQ ID NO 79
<211> LENGTH: 104
<212> TYPE: PRT
<213> ORGANISM: artificial sequence
<220> FEATURE:
<223> OTHER INFORMATION: BT (cattle) TIFA F1+F2

<400> SEQUENCE: 79

Met Ser Ser Phe Glu Asp Ala Asp Thr Glu Glu Met Val Thr Cys Leu
1               5                   10                  15

Gln Met Thr Leu Tyr His Pro Gly His Gln Arg Ser Gly Ile Phe Arg
            20                  25                  30

Ser Ile Lys Phe Phe Asn Arg Glu Lys Leu Pro Thr Ser Glu Val Val
        35                  40                  45

Lys Phe Gly Arg Asn Ser His Thr Cys Asn Tyr Ile Phe Gln Asp Lys
    50                  55                  60

Gln Val Ser Arg Val Gln Phe Ser Leu Gln Val Phe Lys Lys Phe Asn
65                  70                  75                  80

Ser Ser Val Val Ser Phe Glu Ile Lys Asn Met Ser Lys Lys Thr Ser
                85                  90                  95

Leu Leu Val Asp Asn Lys Glu Leu
            100

<210> SEQ ID NO 80
<211> LENGTH: 104
<212> TYPE: PRT
<213> ORGANISM: artificial sequence
<220> FEATURE:
<223> OTHER INFORMATION: CH (goat) TIFA F1+F2

<400> SEQUENCE: 80

Met Ser Ser Phe Glu Asp Val Asp Thr Glu Glu Thr Val Thr Ser Leu
1               5                   10                  15

His Met Thr Leu Tyr His Pro Gly His Gln Arg Ser Gly Ile Phe Gln
            20                  25                  30

```
Ser Ile Lys Phe Cys Asn Arg Glu Thr Leu Pro Thr Ser Glu Val Val
            35                  40                  45

Lys Phe Gly Arg Asn Ser Thr Cys Arg Tyr Thr Phe Gln Asp Lys
 50                  55                  60

Gln Val Ser Arg Val Gln Phe Ser Leu Gln Leu Phe Lys Lys Phe Asp
 65                  70                  75                  80

Ser Ser Val Val Ser Phe Glu Ile Lys Asn Met Ser Lys Lys Thr Asn
                 85                  90                  95

Leu Leu Val Asp Asp Lys Glu Leu
            100
```

<210> SEQ ID NO 81
<211> LENGTH: 103
<212> TYPE: PRT
<213> ORGANISM: artificial sequence
<220> FEATURE:
<223> OTHER INFORMATION: SS (pig) TIFA F1+F2

<400> SEQUENCE: 81

```
Met Ser Ser Phe Glu Asp Ala Asp Thr Glu Thr Leu Thr Cys Leu
 1               5                  10                  15

Gln Met Thr Val Tyr His Pro Gly His Gln Gln Asn Gly Ile Phe Gln
            20                  25                  30

Ser Arg Arg Phe Phe Ser Arg Glu Lys Leu Pro Ser Ser Glu Val Val
            35                  40                  45

Lys Phe Gly Arg Asn Ser Ile Cys Gln Tyr Thr Phe Gln Asp Lys His
 50                  55                  60

Ala Ser Arg Val Gln Phe Ser Leu His Leu Phe Lys Lys Phe Asp Ser
 65                  70                  75                  80

Ser Val Leu Ser Phe Glu Ile Lys Asn Met Ser Lys Lys Thr Ser Leu
                 85                  90                  95

Ile Val Asp Asn Gln Glu Leu
            100
```

<210> SEQ ID NO 82
<211> LENGTH: 104
<212> TYPE: PRT
<213> ORGANISM: artificial sequence
<220> FEATURE:
<223> OTHER INFORMATION: EC (horse) TIFA F1+F2

<400> SEQUENCE: 82

```
Met Ser Ser Phe Glu Asp Ala Asp Thr Glu Glu Thr Leu Thr Cys Leu
 1               5                  10                  15

Gln Met Thr Val Tyr His Pro Gly Gln Gln Pro Asn Gly Ile Phe Gln
            20                  25                  30

Ser Ile Gly Phe His Lys Arg Glu Lys Leu Pro Ser Arg Glu Glu Val
            35                  40                  45

Lys Phe Gly Arg Ser Ser Lys Val Cys Asn Tyr Thr Phe Gln Asp Arg
 50                  55                  60

Gln Val Ser Arg Val Gln Phe Ser Leu Gln Leu Phe Lys Lys Phe Asp
 65                  70                  75                  80

Ser Ser Val Leu Ser Phe Glu Ile Lys Asn Met Ser Lys Arg Thr Ser
                 85                  90                  95

Leu Ile Val Asp Asn Arg Thr Leu
            100
```

<210> SEQ ID NO 83

```
<211> LENGTH: 139
<212> TYPE: PRT
<213> ORGANISM: artificial sequence
<220> FEATURE:
<223> OTHER INFORMATION: HS (human) TIFA F2+F3

<400> SEQUENCE: 83

Val Val Lys Phe Gly Arg Asn Ser Asn Ile Cys His Tyr Thr Phe Gln
1               5                   10                  15

Asp Lys Gln Val Ser Arg Val Gln Phe Ser Leu Gln Leu Phe Lys Lys
            20                  25                  30

Phe Asn Ser Ser Val Leu Ser Phe Glu Ile Lys Asn Met Ser Lys Lys
        35                  40                  45

Thr Asn Leu Ile Val Asp Ser Arg Glu Leu Gly Tyr Leu Asn Lys Met
    50                  55                  60

Asp Leu Pro Tyr Arg Cys Met Val Arg Phe Gly Glu Tyr Gln Phe Leu
65                  70                  75                  80

Met Glu Lys Glu Asp Gly Glu Ser Leu Glu Phe Phe Glu Thr Gln Phe
                85                  90                  95

Ile Leu Ser Pro Arg Ser Leu Leu Gln Glu Asn Asn Trp Pro Pro His
            100                 105                 110

Arg Pro Ile Pro Glu Tyr Gly Thr Tyr Ser Leu Cys Ser Ser Gln Ser
        115                 120                 125

Ser Ser Pro Thr Glu Met Asp Glu Asn Glu Ser
    130                 135

<210> SEQ ID NO 84
<211> LENGTH: 139
<212> TYPE: PRT
<213> ORGANISM: artificial sequence
<220> FEATURE:
<223> OTHER INFORMATION: OC (rabbit) TIFA F2+F3

<400> SEQUENCE: 84

Val Val Lys Phe Gly Arg Asn Ser Lys Val Cys His Tyr Thr Phe Gln
1               5                   10                  15

Asp Lys Gln Ala Ser Arg Val Gln Phe Ser Leu Gln Leu Phe Lys Gln
            20                  25                  30

Phe Asn Ser Ser Val Leu Ser Phe Glu Ile Lys Asn Met Ser Arg Lys
        35                  40                  45

Thr Ser Leu Ile Val Asp Ser Gln Glu Leu Gly Tyr Leu Asn Lys Leu
    50                  55                  60

Asp Leu Pro Tyr Lys Cys Met Val Arg Phe Ser Glu Tyr Gln Phe Leu
65                  70                  75                  80

Met Glu Lys Glu Asp Gly Glu Ala Leu Asp Ser Phe Glu Thr Gln Phe
                85                  90                  95

Ile Leu Ser Pro Arg Pro Leu Leu Gln Glu Asn Ile Trp Pro Pro His
            100                 105                 110

Lys Pro Ile Pro Glu Tyr Gly Ile Tyr Ser Ser Cys Ser Ala Gln Ser
        115                 120                 125

Thr Ser Pro Thr Glu Met Asp Glu Asp Glu Leu
    130                 135

<210> SEQ ID NO 85
<211> LENGTH: 139
<212> TYPE: PRT
<213> ORGANISM: artificial sequence
<220> FEATURE:
<223> OTHER INFORMATION: CL (dog) TIFA F2+F3
```

<400> SEQUENCE: 85

Val Val Lys Phe Gly Arg Asn Ser Asn Ile Cys Arg Tyr Thr Phe Gln
1               5                   10                  15

Asp Lys Gln Val Ser Arg Val Gln Phe Ser Leu Gln Leu Phe Lys Lys
            20                  25                  30

Phe Asp Ser Ser Val Leu Ser Phe Glu Ile Lys Asn Met Ser Lys Lys
        35                  40                  45

Thr Asn Leu Leu Val Asp Asn Lys Glu Leu Cys Tyr Leu Asn Lys Ile
    50                  55                  60

Asp Leu Pro Tyr Lys Cys Met Val Arg Phe Gly Glu Tyr Gln Phe Leu
65                  70                  75                  80

Ile Glu Lys Glu Asp Gly Glu Ser Leu Glu Phe Phe Glu Thr Gln Phe
                85                  90                  95

Ile Leu Ser Pro Arg Ser Leu Leu Gln Glu Asn Asn Trp Pro Ile Gln
            100                 105                 110

Lys Pro Ile Pro Glu Tyr Gly Ser Tyr Ser Ser Cys Phe Thr Gln Asn
        115                 120                 125

Thr Ser Pro Thr Glu Met Asp Glu Asn Glu Leu
    130                 135

<210> SEQ ID NO 86
<211> LENGTH: 139
<212> TYPE: PRT
<213> ORGANISM: artificial sequence
<220> FEATURE:
<223> OTHER INFORMATION: MM (mouse) TIFA F2+F3

<400> SEQUENCE: 86

Val Val Lys Phe Gly Arg Asn Ser Asn Met Cys Gln Tyr Thr Phe Gln
1               5                   10                  15

Asp Lys Gln Val Ser Arg Ile Gln Phe Val Leu Gln Pro Phe Lys Gln
            20                  25                  30

Phe Asn Ser Ser Val Leu Ser Phe Glu Ile Lys Asn Met Ser Lys Lys
        35                  40                  45

Thr Ser Leu Met Val Asp Asn Gln Glu Leu Gly Tyr Leu Asn Lys Met
    50                  55                  60

Asp Leu Pro Tyr Lys Cys Met Leu Arg Phe Gly Glu Tyr Gln Phe Leu
65                  70                  75                  80

Leu Gln Lys Glu Asp Gly Glu Ser Val Glu Ser Phe Glu Thr Gln Phe
                85                  90                  95

Ile Met Ser Ser Arg Pro Leu Leu Gln Glu Asn Asn Trp Pro Thr Gln
            100                 105                 110

Asn Pro Ile Pro Glu Asp Gly Met Tyr Ser Ser Tyr Phe Thr His Arg
        115                 120                 125

Ser Ser Pro Ser Glu Met Asp Glu Asn Glu Leu
    130                 135

<210> SEQ ID NO 87
<211> LENGTH: 139
<212> TYPE: PRT
<213> ORGANISM: artificial sequence
<220> FEATURE:
<223> OTHER INFORMATION: RN (rat) TIFA F2+F3

<400> SEQUENCE: 87

Val Val Lys Phe Gly Arg Asn Ser Asn Met Cys Gln Tyr Thr Phe Gln
1               5                   10                  15

-continued

Asp Lys Gln Val Ser Arg Val Gln Phe Ala Leu Gln Pro Phe Lys Gln
            20                  25                  30

Phe Asn Ser Ser Val Leu Ser Phe Glu Ile Lys Asn Met Ser Lys Lys
            35                  40                  45

Thr Ser Leu Met Val Asp Asn Gln Glu Leu Gly Tyr Leu Asn Lys Met
    50                  55                  60

Asp Leu Pro Tyr Lys Cys Met Leu Arg Phe Gly Glu Tyr Gln Phe Leu
65                  70                  75                  80

Leu Gln Lys Glu Asp Gly Glu Ser Val Glu Ser Phe Glu Thr Gln Phe
                85                  90                  95

Ile Leu Ser Pro Arg Pro Leu Leu Gln Glu Asn Asn Trp Pro Thr Gln
            100                 105                 110

Ser Pro Ile Pro Glu Asp Gly Val Tyr Ser Ser Tyr Phe Thr His Arg
            115                 120                 125

Ser Ser Pro Ala Glu Met Asp Glu Asn Glu Leu
            130                 135

<210> SEQ ID NO 88
<211> LENGTH: 139
<212> TYPE: PRT
<213> ORGANISM: artificial sequence
<220> FEATURE:
<223> OTHER INFORMATION: CG (hamster) TIFA F2+F3

<400> SEQUENCE: 88

Glu Val Lys Phe Gly Arg Asn Ser Asn Ile Cys Arg Tyr Thr Phe Gln
1               5                   10                  15

Asp Lys Gln Val Ser Arg Val Gln Phe Ala Leu Gln Pro Phe Lys Gln
            20                  25                  30

Phe Asn Ser Ser Val Leu Ser Phe Glu Ile Lys Asn Met Ser Lys Lys
            35                  40                  45

Thr Ser Leu Met Val Asp Asn Gln Glu Leu Gly Tyr Leu Asn Lys Met
    50                  55                  60

Asp Leu Pro Tyr Lys Cys Leu Leu Arg Phe Gly Glu Tyr Gln Phe Leu
65                  70                  75                  80

Leu Glu Lys Glu Asp Gly Glu Ser Val Glu Ser Phe Glu Thr Gln Phe
                85                  90                  95

Ile Leu Ser Pro Arg Pro Leu Leu Gln Glu Asn Asn Trp Pro Thr Gln
            100                 105                 110

Ser Pro Ile Pro Glu Asp Gly Gly Tyr Ser Ser Tyr Phe Thr His Arg
            115                 120                 125

Thr Ser Pro Thr Glu Met Asp Glu Asn Glu Leu
            130                 135

<210> SEQ ID NO 89
<211> LENGTH: 139
<212> TYPE: PRT
<213> ORGANISM: artificial sequence
<220> FEATURE:
<223> OTHER INFORMATION: CC (beaver) TIFA F2+F3

<400> SEQUENCE: 89

Val Val Lys Phe Gly Arg Asn Ser Ser Ile Cys Arg Tyr Thr Phe Gln
1               5                   10                  15

Asp Lys Gln Val Ser Arg Val Gln Phe Ser Leu Gln Pro Phe Lys Gln
            20                  25                  30

Phe Asn Ser Ser Val Leu Ser Phe Glu Ile Lys Asn Met Ser Lys Lys

-continued

```
                  35                  40                  45

Thr Ser Leu Ile Val Asp Ser Gln Glu Leu Gly Tyr Leu Asn Lys Met
 50                  55                  60

Asp Leu Pro Tyr Arg Cys Met Val Arg Phe Gly Glu Tyr Gln Phe Leu
 65                  70                  75                  80

Leu Glu Lys Glu Asp Gly Glu Ser Leu Glu Ser Phe Gln Thr His Phe
                 85                  90                  95

Ile Leu Ser Pro Arg Pro Leu Gln Glu Asn Asn Trp Pro Ala Gln
                100                 105                 110

Thr Pro Ile Pro Glu Asp Gly Gly Tyr Ser Ser Tyr Leu Thr Pro Ser
                115                 120                 125

Thr Phe Pro Thr Glu Ile Asp Glu Asn Glu Leu
            130                 135

<210> SEQ ID NO 90
<211> LENGTH: 139
<212> TYPE: PRT
<213> ORGANISM: artificial sequence
<220> FEATURE:
<223> OTHER INFORMATION: CP (guinea pig) TIFA F2+F3

<400> SEQUENCE: 90

Val Val Lys Phe Gly Arg Asn Ser Ser Cys His Tyr Ile Phe Gln
 1               5                  10                  15

Asp Lys Gln Ala Ser Arg Val Gln Phe Ser Leu His Pro Phe Lys Pro
                 20                  25                  30

Phe Asn Ser Ser Val Leu Ser Phe Glu Ile Lys Asn Leu Ser Lys Lys
             35                  40                  45

Thr Ser Leu Ile Val Asp Ser Arg Glu Leu Arg Tyr Leu Asn Lys Met
 50                  55                  60

Asp Leu Pro Tyr Arg Cys Met Val Arg Phe Gly Glu Tyr Gln Phe Leu
 65                  70                  75                  80

Leu Glu Arg Glu Asp Gly Glu Ser Leu Glu Ser Phe Glu Thr Gln Phe
                 85                  90                  95

Val Phe Ser Pro Arg Pro Leu Gln Glu Asn Ser Trp Pro Thr Gln
                100                 105                 110

Ser Pro Ile Pro Glu Asp Gly Ser Phe Ser Ser Gly Tyr Thr Arg Ser
                115                 120                 125

Ser Phe Pro Met Glu Met Asp Glu Asn Glu Trp
            130                 135

<210> SEQ ID NO 91
<211> LENGTH: 139
<212> TYPE: PRT
<213> ORGANISM: artificial sequence
<220> FEATURE:
<223> OTHER INFORMATION: BT (cattle) TIFA F2+F3

<400> SEQUENCE: 91

Val Val Lys Phe Gly Arg Asn Ser His Thr Cys Asn Tyr Ile Phe Gln
 1               5                  10                  15

Asp Lys Gln Val Ser Arg Val Gln Phe Ser Leu Gln Val Phe Lys Lys
                 20                  25                  30

Phe Asn Ser Ser Val Val Ser Phe Glu Ile Lys Asn Met Ser Lys Lys
             35                  40                  45

Thr Ser Leu Leu Val Asp Asn Lys Glu Leu Gly Tyr Leu Asn Lys Met
 50                  55                  60
```

```
Asp Leu Pro Asp Lys Cys Met Ile Arg Phe Gly Asp Tyr Gln Phe Leu
 65                  70                  75                  80

Val Glu Lys Glu Asp Gly Glu Ser Leu Glu Phe Phe Glu Ile Gln Phe
                 85                  90                  95

Ser Leu Ser Lys Lys Pro Leu Leu Gln Glu Asn Asn Trp Leu Ser Gln
            100                 105                 110

Glu Pro Ile Pro Glu Cys Gly Ser Tyr Ser Cys Leu Thr Gln Asn
        115                 120                 125

Asn Ser Pro Met Glu Val Gly Glu Asn Glu Trp
    130                 135

<210> SEQ ID NO 92
<211> LENGTH: 139
<212> TYPE: PRT
<213> ORGANISM: artificial sequence
<220> FEATURE:
<223> OTHER INFORMATION: CH (goat) TIFA F2+F3

<400> SEQUENCE: 92

Val Val Lys Phe Gly Arg Asn Ser Ser Thr Cys Arg Tyr Thr Phe Gln
 1               5                  10                  15

Asp Lys Gln Val Ser Arg Val Gln Phe Ser Leu Gln Leu Phe Lys Lys
                20                  25                  30

Phe Asp Ser Ser Val Val Ser Phe Glu Ile Lys Asn Met Ser Lys Lys
            35                  40                  45

Thr Asn Leu Leu Val Asp Asp Lys Glu Leu Ser Tyr Leu Asn Lys Met
 50                  55                  60

Asp Leu Pro Asp Lys Cys Leu Ile Arg Phe Gly Asp Tyr Gln Phe Leu
 65                  70                  75                  80

Val Glu Lys Glu Asp Gly Glu Ser Leu Glu Phe Phe Glu Ile Gln Phe
                 85                  90                  95

Phe Leu Ser Ile Arg Pro Leu Leu Gln Glu Asn Lys Trp Leu Pro Gln
            100                 105                 110

Lys Pro Thr Pro Glu Cys Gly Ser Cys Ser Pro Cys Ser Thr Gln Asn
        115                 120                 125

Asn Ser Pro Met Glu Ala Gly Glu Asn Glu Trp
    130                 135

<210> SEQ ID NO 93
<211> LENGTH: 138
<212> TYPE: PRT
<213> ORGANISM: artificial sequence
<220> FEATURE:
<223> OTHER INFORMATION: SS (pog TIFA F2+F3)

<400> SEQUENCE: 93

Val Val Lys Phe Gly Arg Asn Ser Ile Cys Gln Tyr Thr Phe Gln Asp
 1               5                  10                  15

Lys His Ala Ser Arg Val Gln Phe Ser Leu His Leu Phe Lys Lys Phe
                20                  25                  30

Asp Ser Ser Val Leu Ser Phe Glu Ile Lys Asn Met Ser Lys Lys Thr
            35                  40                  45

Ser Leu Ile Val Asp Asn Gln Leu Gly Tyr Leu Asn Lys Met Asp
 50                  55                  60

Leu Pro Pro Lys Cys Met Val Arg Phe Gly Asp Tyr Gln Phe Leu Ile
 65                  70                  75                  80

Glu Lys Glu Asp Gly Glu Ser Leu Glu Phe Phe Glu Ile Gln Phe Ile
                 85                  90                  95
```

```
Leu Ser Thr Arg Ser Leu Leu Gln Glu Asn Asn Trp Leu Pro Gln Lys
            100                 105                 110

Pro Ile Pro Glu Cys Gly Asn Tyr Leu Ser Cys Ser Thr Gln Gly Asn
            115                 120                 125

Ser Pro Ile Glu Met Gly Glu Asn Glu Trp
            130                 135

<210> SEQ ID NO 94
<211> LENGTH: 139
<212> TYPE: PRT
<213> ORGANISM: artificial sequence
<220> FEATURE:
<223> OTHER INFORMATION: EC (horse) TIFA F2+F3

<400> SEQUENCE: 94

Glu Val Lys Phe Gly Arg Ser Ser Lys Val Cys Asn Tyr Thr Phe Gln
1               5                   10                  15

Asp Arg Gln Val Ser Arg Val Gln Phe Ser Leu Gln Leu Phe Lys Lys
            20                  25                  30

Phe Asp Ser Ser Val Leu Ser Phe Glu Ile Lys Asn Met Ser Lys Arg
            35                  40                  45

Thr Ser Leu Ile Val Asp Asn Arg Thr Leu Asp Phe Leu His Lys Val
    50                  55                  60

Asp Leu Pro Asp Arg Cys Met Ile Arg Phe Gly Asp Tyr Gln Ile Leu
65                  70                  75                  80

Met Glu Lys Glu Asp Gly Val Ser Leu Glu Phe Phe Glu Thr Glu Phe
            85                  90                  95

Ile Leu Ser Pro Arg Ser Leu Leu Gln Lys Asn Tyr Trp Pro Pro Gln
            100                 105                 110

Asn Pro Ile Pro Glu Tyr Cys His Ser Val Trp Ser Ser Ser Gln Ser
            115                 120                 125

Thr Ser Pro Met Glu Thr Asp Glu Asn Glu Leu
            130                 135

<210> SEQ ID NO 95
<211> LENGTH: 25
<212> TYPE: RNA
<213> ORGANISM: artificial sequence
<220> FEATURE:
<223> OTHER INFORMATION: siRNA targeting TIFA

<400> SEQUENCE: 95
ucaggacaaa cagguuuccc gaguu                                       25
```